US008652475B2

(12) United States Patent
Holers et al.

(10) Patent No.: US 8,652,475 B2
(45) Date of Patent: *Feb. 18, 2014

(54) INHIBITION OF FACTOR B, THE ALTERNATIVE COMPLEMENT PATHWAY AND METHODS RELATED THERETO

(75) Inventors: Vernon Michael Holers, Denver, CO (US); Joshua M. Thurman, Greenwood Village, CO (US); Christian Taube, Frankfurt (DE); Erwin W. Gelfand, Englewood, CO (US); Gary Steven Gilkeson, Charleston, SC (US)

(73) Assignees: MUSC Foundation for Research Development, Charleston, SC (US); National Jewish Health, Denver, CO (US); The Regents of the University of Colorado, a body corporate, Denver, CO (US)

( * ) Notice: Subject to any disclaimer, the term of this patent is extended or adjusted under 35 U.S.C. 154(b) by 772 days.

This patent is subject to a terminal disclaimer.

(21) Appl. No.: 11/888,997

(22) Filed: Aug. 3, 2007

(65) Prior Publication Data

US 2008/0075720 A1    Mar. 27, 2008

Related U.S. Application Data

(63) Continuation of application No. 11/057,047, filed on Feb. 10, 2005, now Pat. No. 7,999,082, which is a continuation-in-part of application No. PCT/US2004/015040, filed on May 13, 2004.

(60) Provisional application No. 60/543,594, filed on Feb. 10, 2004, provisional application No. 60/636,239, filed on Dec. 14, 2004.

(51) Int. Cl.
*A61K 39/395* (2006.01)
*C07K 16/28* (2006.01)

(52) U.S. Cl.
USPC ............... 424/145.1; 424/141.1; 424/158.1; 424/192.1; 530/387.1; 530/387.3; 530/388.1; 530/388.25

(58) Field of Classification Search
None
See application file for complete search history.

(56) References Cited

U.S. PATENT DOCUMENTS

| 4,845,083 | A | 7/1989 | Fortin et al. |
|---|---|---|---|
| 4,883,784 | A | 11/1989 | Kaneko et al. |
| 5,679,546 | A | 10/1997 | Ko et al. |
| 5,869,615 | A | 2/1999 | Hourcade et al. |
| 5,976,540 | A | 11/1999 | Rittershaus et al. |
| 6,165,463 | A | 12/2000 | Platz et al. |
| 6,248,365 | B1 | 6/2001 | Römisch et al. |
| 6,458,360 | B1 * | 10/2002 | Fearon et al. ............ 424/195.11 |
| 6,521,450 | B1 | 2/2003 | Atkinson et al. |
| 6,820,011 | B2 | 11/2004 | Chen et al. |
| 6,897,290 | B1 | 5/2005 | Atkinson et al. |
| 7,759,304 | B2 | 7/2010 | Gilkeson et al. |
| 7,964,705 | B2 * | 6/2011 | Emlen et al. ............... 530/387.3 |
| 7,999,082 | B2 * | 8/2011 | Holers et al. ............. 530/388.25 |
| 8,007,804 | B2 | 8/2011 | Tomlinson et al. |
| 2002/0015701 | A1 | 2/2002 | Gupta-Bansal et al. |
| 2002/0081293 | A1 | 6/2002 | Fung et al. |
| 2003/0198636 | A1 | 10/2003 | Gupta-Bansal et al. |
| 2003/0235582 | A1 | 12/2003 | Singh et al. |
| 2004/0014782 | A1 | 1/2004 | Krause |
| 2005/0107319 | A1 | 5/2005 | Bansal |
| 2005/0169915 | A1 | 8/2005 | Do Couto et al. |
| 2005/0255552 | A1 | 11/2005 | Flynn et al. |
| 2005/0260198 | A1 | 11/2005 | Holers et al. |
| 2006/0002944 | A1 | 1/2006 | Ashkenazi et al. |
| 2006/0134098 | A1 | 6/2006 | Bebbington et al. |
| 2006/0178308 | A1 | 8/2006 | Schwaeble et al. |
| 2006/0263819 | A1 | 11/2006 | Hageman et al. |
| 2006/0292141 | A1 | 12/2006 | Holers et al. |
| 2007/0020647 | A1 | 1/2007 | Hageman et al. |
| 2007/0065433 | A1 | 3/2007 | Mollnes et al. |
| 2007/0183970 | A1 | 8/2007 | Goldenberg et al. |
| 2008/0075720 | A1 | 3/2008 | Holers et al. |
| 2008/0102040 | A1 | 5/2008 | Holers et al. |
| 2008/0267980 | A1 * | 10/2008 | Tomlinson et al. ........ 424/178.1 |
| 2008/0299114 | A1 | 12/2008 | Emlen et al. |
| 2009/0175847 | A1 | 7/2009 | Barghorn et al. |
| 2012/0171206 | A1 | 7/2012 | Tomlinson et al. |

FOREIGN PATENT DOCUMENTS

| CA | 1340879 C | 1/2000 |
|---|---|---|
| WO | WO-99/42133 A1 | 8/1999 |
| WO | WO-00/21559 A2 | 4/2000 |
| WO | WO-00/21559 A3 | 4/2000 |

(Continued)

OTHER PUBLICATIONS

Bendig, Methods: A Companion to Methods in Enzymology 1995; 8:83-93, 1995.*
Padlan et al., PNAS 86: 5938-5942, 1989.*
Attwood, Science 290: 471-473, 2000.*
Skolnick et al., Trends in Biotech. 18: 34-39, 2000.*
Hourcade et al., Journal of Immunology 162: 2906-2911, 1999.*
Lederman, S. et al. (1991). "A Single Amino Acid Substitution in a Common African Allele of the CD4 Molecule Ablates Binding of the Monoclonal Antibody, OKT4," *Molecular Immunology* 28(11):1171-1181.

(Continued)

*Primary Examiner* — Phillip Gambel
(74) *Attorney, Agent, or Firm* — Clark & Elbing LLP; Kristina Bieker-Brady; Todd Armstrong

(57) ABSTRACT

Disclosed are novel inhibitors of the alternative complement pathway and particularly, novel anti-factor B antibodies. Also disclosed is the use of such inhibitors to reduce or prevent airway hyperresponsiveness and/or airway inflammation by selectively inhibiting the alternative complement pathway, thereby treating diseases in which such conditions play a role. Also disclosed is the use of such inhibitors to reduce or prevent other diseases and conditions, including ischemia-reperfusion injury, by inhibition of the alternative complement pathway.

27 Claims, 17 Drawing Sheets

(56) References Cited

FOREIGN PATENT DOCUMENTS

| WO | WO-01/47963 A2 | 7/2001 |
|---|---|---|
| WO | WO-01/47963 A3 | 7/2001 |
| WO | WO-2004/022096 A1 | 3/2004 |
| WO | WO-2004/031240 A1 | 4/2004 |
| WO | WO-2004/103288 A2 | 12/2004 |
| WO | WO-2004/103288 A3 | 12/2004 |
| WO | WO-2004/106369 A2 | 12/2004 |
| WO | WO-2004/106369 A3 | 12/2004 |
| WO | WO-2005/003159 A1 | 1/2005 |
| WO | WO-2005/023195 A2 | 3/2005 |
| WO | WO-2005/023195 A3 | 3/2005 |
| WO | WO-2005/069970 A2 | 8/2005 |
| WO | WO-2005/077417 A1 | 8/2005 |
| WO | WO-2006/012621 A2 | 2/2006 |
| WO | WO-2006/012621 A3 | 2/2006 |
| WO | WO-2006/055178 A2 | 5/2006 |
| WO | WO-2006/062716 A2 | 6/2006 |
| WO | WO-2006/062716 A3 | 6/2006 |
| WO | WO-2006/083533 A2 | 8/2006 |
| WO | WO-2006/083533 A3 | 8/2006 |
| WO | WO-2006/122257 A2 | 11/2006 |
| WO | WO-2006/122257 A3 | 11/2006 |
| WO | WO-2007/011363 A2 | 1/2007 |
| WO | WO-2007/011363 A3 | 1/2007 |
| WO | WO-2007/029008 A2 | 3/2007 |
| WO | WO-2007/029008 A3 | 3/2007 |
| WO | WO-2007/032876 A2 | 3/2007 |
| WO | WO-2007/032876 A3 | 3/2007 |
| WO | WO-2007/056227 A2 | 5/2007 |
| WO | WO-2007/056227 A3 | 5/2007 |
| WO | WO-2008/140653 A2 | 11/2008 |
| WO | WO-2008/140653 C1 | 11/2008 |
| WO | WO-2011/057158 A1 | 5/2011 |
| WO | WO-2011/143637 A1 | 11/2011 |
| WO | WO-2011/163412 A1 | 12/2011 |

OTHER PUBLICATIONS

Li, C.H. et al. (Jun. 1980). "β-Endorphin Omission Analogs: Dissociation of Immunoreactivity from Other Biological Activities," *Proc. Natl. Acad. Sci USA* 77(6):3211-3214.

Bendayan, M. (1995). "Possibilities of False Immunocytochemical Results Generated by the Use of Monoclonal Antibodies: The Example of the Anti-proinsulin Antibody," *J. Histochem. Cytochem.* 43(9):881-886.

Bost, K.L. et al. (1988). "Antibodies Against a Peptide Sequence Within the HIV Envelope Protein Crossreacts with Human Interleukin-2," *Immunological Investigation* 17(6&7):577-586.

Non-Final Office Action mailed on Apr. 30, 2009, for U.S. Appl. No. 11/057,047, filed Feb. 10, 2005, 12 pages.

Clardy, C.W. et al. (Apr. 1992). "In vitro Inhibition of Complement Activation Using a Monoclonal Antibody (McAb) Directed Against Human Factor B (FB)," *Pediatric Res.* 31(4):331A, Abstract No. 1969.

Clardy, C.W. et al. (Oct. 1994). "Complement Activation by Whole Endotoxin is Blocked by a Monoclonal Antibody to Factor B," *Infect. Immunity* 62(10):4549-4555.

Girardi, G. at al. (Dec. 2003). "Complement C5a Receptors and Neutrophils Mediate Fetal Injury in the Antiphospholipid Syndrome," *J. Clin. Invest.* 112(11):1644-1653.

Girardi, G. et al. (Feb. 2004). "Complement C5a Receptors and Neutrophils Mediate Fetal Injury in the Antiphospholipid Syndrome,"*J. Clin. Invest.* corrigendum 113(4):646.

Glovsky, M.M. et al. (Dec. 2004). "Complement Determinations in Human Disease," *Annals of Allergy, Asthma, and Immunology* 93(6):513-523 & 605.

International Preliminary Report on Patentability mailed on Jul. 7, 2005, for PCT Application No. PCT/US2005/004346, filed on Feb. 10, 2005, 4 pages.

International Search Report mailed on Jul. 7, 2005, for PCT Application No. PCT/US05/04346, filed on Feb. 10, 2005, 2 pages.

Kolb, W.P. et al. (1989). "Ba and Bb Fragments of Factor B Activation: Fragment Production, Biological Activites, Neoepitope Expression and Quantitation in Clinical Samples," *Complement & Inflammation* 6:175-204.

Tanaka, E. et al. (1991). "Murine Monoclonal Anti-Ba Antibody that Enhances Haemolytic Activity of Factor B," *Immunol.* 73:383-387.

Thurman, J.M. et al. (2004). "A Novel Inhibitor of the Alternative Pathway of Complement Protects Mice from Fetal Injury in the Antiphospholipid Syndrome," *Molecular Immunology* 41:318, Abstract No. 254.

Thurman, J.M. et al. (2004). "Complement Activation Through the Alternative Pathway is Necessary for the Development of Airway Hyperresponsiveness (AHR) and Inflammation in a Model of Human Asthma," *Molecular Immunology* 41:319, Abstract No. 256.

Thurman, J.M. et al. (2005, e-pub. Sep. 17, 2004). "A Novel Inhibitor of the Alternative Complement Pathway Prevents Antiphospholipid Antibody-Induced Pregnancy Loss in Mice," *Molecular Immunology* 42:87-97.

Thurman, J.M. et al. (Oct. 2004). "A Novel Inhibitor of the Alternative Pathway of Complement Protects Mice from Ischemic Acute Renal Failure," *American Nephrology Society Meeting*, Abstract, 1 page.

Non-Final Office Action mailed on Oct. 19, 2007, for U.S. Appl. No. 11/057,047, filed Feb. 10, 2005, 4 pages.

Interview Summary mailed on Apr. 16, 2008, for U.S. Appl. No. 11/057,047, filed Feb. 10, 2005, 4 pages.

Declaration of Joshua M. Thurman mailed on Apr. 16, 2008, for U.S. Appl. No. 11/057,047, filed Feb. 10, 2005, 3 pages.

Anonymous. (Date Unknown). "Monoclonal Antibody to Human Factor B (Ba), Catalog No. A225" in *Quidel Corporation Product Catalog*, located at //www.quidel.com/products/product_detail.php?prod=82&group=2>, last visited on Aug. 4, 2008, two pages.

Anonymous. (Date Unknown). "Monoclonal Antibody to Human Factor B (Bb), Catalog No. A227," in *Quidel Corporation Product Catalog*, located at ://www.quidel.com/products/product_detail.php?group=2&prod=83>, last visited on Aug. 4, 2008, two pages.

Holers, V.M. et al. (2004). "The Alternative Pathway of Complement in Disease: Opportunities for Therapeutic Targeting," *Molecular Immunology* 41:147-152.

Hourcade, D.E. et al. (1995). "Analysis of the Short Consensus Repeats of Human Complement Factor B by Site-directed Mutagenesis," *J. Bio. Chem.* 270(34):19716-19722.

Supplementary Partial European Search Report mailed on Jul. 7, 2008, for EP Application No. 05722948, filed on Feb. 10, 2005, 7 pages.

Thurman, J.M. et al. (2003). "Lack of a Functional Alternative Complement Pathway Ameliorates Ischemic Acute Renal Failure in Mice," *J. Immunology* 170(3):1517-1523.

Ueda, A. et al. (Feb. 15, 1987). "Probing Functional Sites on Complement Protein B with Monoclonal Antibodies: Evidence for C3b-Binding Sites on Ba," *J. Immunology* 138(4):1143-1149.

Chardès, T. et al. (1999). "Efficient Amplification and Direct Sequencing of Mouse Variable Regions from any Immunoglobulin Gene Family," *FEBS Lett.* 452(3):386-394.

Choi, W.S. et al. (Sep. 25, 2001). "Inhalation Delivery of Proteins from Ethanol Suspensions," *Proc. Natl. Acad. Sci.* 98(20):11103-11107.

International Preliminary Report on Patentability mailed on Sep. 24, 2009, for PCT Application No. PCT/US2008/003381, filed on Mar. 14, 2008, 9 pages.

International Search Report mailed on Feb. 11, 2009, for PCT Application No. PCT/US2008/003381, filed on Mar. 14, 2008, 6 pages.

Stribling, R. et al. (Dec. 1992). "Aerosol Gene Delivery In Vivo," *Proc. Natl. Acad. Sci. USA* 89:11277-11281.

Tatusova, T.A. et al. (May 15, 1999). "BLAST 2 Sequences, a New Tool for Comparing Protein and Nucleotide Sequences," *FEMS Microbiol. Lett.* 174(2):247-250.

Taube, C. et al. (May 23, 2006). "Factor B of the Alternative Complement Pathway Regulates Development of Airway Hyperresponsiveness and Inflammation," *Proc. Natl. Acad. Sci. USA* 103(21):8084-8089.

(56) References Cited

OTHER PUBLICATIONS

Written Opinion of the International Searching Authority mailed on Feb. 11, 2009, for PCT Application No. PCT/US2008/003381, filed on Mar. 14, 2008, 7 pages.
Abass, A.K. et al. eds. (1991). *Cellular and Molecular Immunology*, W.B. Saunders Company: Philadelphia, PA, pp. 54.
Caldas, C. et al. (2003). "Humanization of the Anti-CD18 Antibody 6.7: An Unexpected Effect of a Framework Residue in Binding to Antigen," *Molecular Immunology* 39:941-952.
Chien, N.C. et al. (Jul. 1989). "Significant Structural and Functional Change of an Antigen-Binding Site by a Distant Amino Acid Substitution: Proposal of a Structural Mechanism," *Proc. Natl. Acad. Sci. USA* 86:5532-5536.
Giusti, A.M. et al. (May 1987). "Somatic Diversification of S107 from an Antiphosphocholine to an Anti-DNA Autoantibody is Due to a Single Base Change in its Heavy Chain Variable Region," *Proc. Natl. Acad. Sci. USA* 84:2926-2930.
Holm, P. et al. (2007). "Functional Mapping and Single Chain Construction of the Anti-Cytokeratin 8 Monoclonal Antibody TS1," *Molecular Immunology* 44:1075-1084.
MacCallum, R. M. (1996). "Antibody-Antigen Interactions: Contact Analysis and Binding Site Topography," *J. Mol. Biol.* 262:732-745.
Mariuzza, R.A. et al. (1987). "The Structural Basis of Antigen-Antibody Recognition," *Annu. Rev. Biophys. Biphys. Chem.* 16:139-159.
Non-Final Office Action mailed on Aug. 16, 2010, for U.S. Appl. No. 12/049,233, filed Mar. 14, 2008, 28 pages.
Rudikoff, S. et al. (Mar. 1982). "Single Amino Acid Substitution Altering Antigen-Binding Specificity," *Proc. Natl. Acad. Sci. USA* 79:1979-1983.
Thurman, J.M. et al. (2006). "Treatment with an Inhibitory Monoclonal Antibody to Mouse Factor B Protects Mice from Induction of Apoptosis and Renal Ischemia/Reperfusion Injury," *J. Am. Soc. Nephrol.* 17:705-715.
Alexander, J.J. et al. (2005). "Complement-Dependent Apoptosis and Inflammatory Gene Changes in Murine Lupus Cerebritis," *J. Immunol.* 175:8312-8319.
Boos, L.A. et al. (2004, e-pub. Jul. 6, 2004). "Murine Complement C4 Is Not Required for Experimental Autoimmune Encephalomyelitis," *Glia* 49:158-160.
Cole, D.S. et al. (2003). "Beyond lysis: How Complement Influences Cell Fate," *Clin. Sci.* 104:455-466.
Daha, M.R. et al. (May 1984). "Stabilization of the Amplification Convertase of Complement by Monoclonal Antibodies Directed Against Human Factor B," *Infect. Immun.* 132(5):2538-2542.
Gilkeson, G.S. (Date Unknown). "NIH Research Portfolio Online Reporting Tools. Project No. 5R0IA1047469-05," located at <http://projectreporter.nih.gov/pr_Prj_info_desc_dtls.cfm?icde=0&aid=6712799&print=yes>, last visited on Apr. 25, 2011, 2 pages.
Hall, R.E. (Sep. 1982). "Cooperative Interaction of Factor B and Other Complement Components with Mononuclear Cells in the Antibody-Independent Lysis of Xenogeneic Erythrocytes," *J. Exp. Med.* 156:834-843.
Holers, V.M. (2000). "Phenotypes of Complement Knockouts," *Immunopharmacology* 49:125-131.
Holers, V.M. (2003). "The Complement System as a Therapeutic Target in Autoimmunity," *Clin. Immunol.* 107:140-151.
Kang, B.H.J. et al. (2000). "A Novel Anti-Human Factor B Monoclonal Antibody Inhibits Factor D-Mediated Associated and Cleavage of Factor B," Abstract No. 191, *Immunopharmacology* 49(1-2):68.
Kurucz, I. et al. (2006). "Current Animal Models of Bronchial Asthma," *Current Pharmaceutical Design* 12(25):3175-3194.
Kuttner-Kondo, L.A. et al. (2001). "Characterization of the Active Sites in Decay-Accelerating Factor," *Journal of Immunology* 167:2164-2171.
Lemanske, R.F. Jr. (2009). "Asthma Therapies Revisited. What Have We Learned?" *Proc. Am. Thorac. Soc.* 6:312-315.

Matsumoto, M. et al. (Aug. 1997). "Abrogation of the Alternative Complement Pathway by Targeted Deletion of Murine Factor B," *Proc. Natl. Acad. Sci. USA* 94:8720-8725.
Maulik, S. et al. (1997). *Molecular Biotechnology: Therapeutic Applications and Strategies*, Wiley-Liss, Inc., pp. v-wiii (Table of Contents Only.)
Morgan, B.P (1999). "Regulation of the Complement Membrane Attack Pathway," *Crit. Rev. Immunol.* 19(3):173-198.
Nataf, S. et al. (1999). "Complement Anaphylatoxin Receptors on Neurons: New Tricks for Old Receptors?" *Trends Neurosci.* 22(9):397-402.
Nataf, S. et al. (2000). "Attenuation of Experimental Autoimmune Demyelination in Complement-Deficient Mice," *J. Immunol.* 165:5867-5873.
Non-Final Office Action mailed on Oct. 7, 2010, for U.S. Appl. No. 11/843,617, filed Aug. 22, 2007, 11 pages.
Non-Final Office Action mailed on Oct. 13, 2010, for U.S. Appl. No. 11/057,047, filed Feb. 10, 2005, 8 pages.
Non-Final Office Action mailed on Jan. 28, 2011, for U.S. Appl. No. 11/441,828, filed May 26, 2006, 12 pages.
Notice of Allowance mailed on Feb. 15, 2011, for U.S. Appl. No. 12/049,233, filed Mar. 14, 2008, 10 pages.
O'Barr, S.A. et al. (2001). "Neuronal Expression of a Functional Receptor for the C5a Complement Activation Fragment," *J. Immunol.* 166:4154-4162.
Peters, M.G. (Oct. 1988). "The Bb Fragment of Complement Factor B Acts as a B Cell Growth Factor," *J. Exp. Med.* 168:1225-1235.
Takahashi, M. (1980). "Solubilization of Antigen-Antibody Complexes: A New Function of Complement as a Regulator of Immune Reactions," *Prog. Allergy* 27:134-166.
Thurman, J.M. et al. (2005). "Acute Tubular Necrosis is Characterized by Activation of the Alternative Pathway of Complement," *Kidney Int.* 67:524-530.
Thurman, J.M. et al. (2006). "The Central Role of the Alternative Complement Pathway in Human Disease," *J. Immunol.* 176:1305-1310.
Watanabe, H. et al. (2000). "Modulation of Renal Disease in MRL/lpr Mice Genetically Deficient in Alternative Complement Pathway Factor B," *J. Immunol.* 164:786-794.
Xu, Y. et al. (1997). "Contribution of the Complement Control Protein Modules of C2 in C4b Binding Assessed by Analysis of C2/Factor B Chimeras," *J. Immunol.* 158:5958-5965.
Brandis, K. (Date Unknown). "Acid-Base Physiology," located at //www.anaesthesiamcq.com/AcidBaseBook/ab4_4.php>, last visited on Sep. 19, 2011, 2 pages.
De Broe, M.E. et al. (1989). "Pathophysiology of Hemodialysis-Associated Hypoxemia," *Adv. Nephrol. Necker Hosp.* 18:297-315, Abstract Only.
Final Office Action mailed on Jun. 21, 2011, for U.S. Appl. No. 11/843,617, filed Aug. 22, 2007, 11 pages.
Final Office Action mailed on Jul. 21, 2011, for U.S. Appl. No. 11/441,828, filed May 26, 2006, 7 pages.
German, J.W. et al. (Jul. 1996). "Systemic Complement Depletion Inhibits Experimental Cerebral Vasospasm," *Neurosurgery* 39(1):141-145, discussion 145-146, Abstract Only.
Jaeschke, H. et al. (2006). "Role of Neutrophils in Acute Inflammatory Liver Injury," *Liver International* 26:912-919.
Kulkarni, A.P. et al. (2004). "Neuroprotection from Complement-Mediated Inflammatory Damage," *Annals of the New York Academy of Sciences* 1035:147-164.
Langlois, P.F. et al. (1988). "Complement Activation Occurs Through Both Classical and Alternative Pathways Prior to Onset and Resolution of Adult Respiratory Distress Syndrome," *Clin. Immunol. Immunopathol.* 47:152-163.
Leinhase, I. et al. (Jul. 14, 2006). "Reduced Neuronal Cell Death After Experimental Brian Injury in Mice Lacking a Functional Alternative Pathway of Complement Activation," *BMC Neuroscience* 7:55, 12 pages.
Non-Final Office Action mailed on Dec. 23, 2011, for U.S. Appl. No. 11/843,617, filed on Aug. 22, 2007, 11 pages.
Notice of Allowance mailed on Apr. 5, 2011, for U.S. Appl. No. 11/057,047, filed on Feb. 10, 2005, 7 pages.

(56) References Cited

OTHER PUBLICATIONS

Rood, P.P. et al. (Jan. 27, 2007). "Reduction of Early Graft Loss After Intraportal Porcine Islet Transplantation in Monkeys," *Transplantation* 83(2):202-210, Abstract Only.

Rounioja, S. et al. (Jun. 2005). "Mechanism of Acute Fetal Cardiovascular Depression After Maternal Inflammatory Challenge in Mouse," *Am. J. Pathol.* 166(6):1585-1592, Abstract Only.

Supplementary European Search Report mailed on Nov. 24, 2011, for EP Application No. 06771303.2, filed on May 26, 2006, 12 pages.

Younger, J.G. et al. (2001). "Detrimental Effects of Complement Activation in Hemorrhagic Shock," *J. Appl. Physiol.* 90:441-446, Corrigenda (2004). *J. Appl. Physiol.* 96:405.

Anderson et al., "Activation of complement pathways after contusion-induced spinal cord injury," *J. Neurotrauma* 21: 1831-1846, 2004.

Barnum, "Inhibition of complement as a therapeutic approach in inflammatory central nervous system (CNS) disease," *Mol. Med.* 5: 569-582, 1999.

Bellander et al., "Activation of the complement cascade and increase of clusterin in the brain following a cortical contusion in the adult rat," *J. Neurosurg.* 85: 468-475, 1996.

Bellander et al., "Complement activation in the human brain after traumatic head injury," *J. Neurotrauma* 18: 1295-1311, 2001.

Casarsa et al., "Intracerebroventricular injection of the terminal complement complex causes inflammatory reaction in the rat brain," *Eur. J. Immunol.* 33: 1260-1270, 2003.

Chen et al., "An experimental model of closed head injury in mice: pathophysiology, histopathology, and cognitive deficits," *J. Neurotrauma* 13: 557-568, 1996.

CRASH trial collaborators, "Effect of intravenous corticosteroids on death within 14 days in 10008 adults with clinically significant head injury (MRC CRASH trial): randomised placebo-controlled trial," *Lancet* 364: 1321-1328, 2004.

Dutton and McCunn, "Traumatic Brain Injury," *Curr. Opin. Crit. Care* 9: 503-509, 2003.

Eldadah and Faden, "Caspase pathways, neuronal apoptosis, and CNS injury," *J. Neurotrauma* 17: 811-829, 2000.

Elf et al., "Prevention of secondary insults in neurointensive care of traumatic brain injury," *Eur. J. of Trauma* 2: 74-80, 2003.

Elward et al., "CD46 plays a key role in tailoring innate immune recognition of apoptotic and necrotic cells," *J. Biol. Chem.* 280: 36342-36354, 2005.

European Patent Office Communication dated Oct. 27, 2010, for European Application No. 08794326.2, filed on Mar. 14, 2008 (7 pages).

Extended European Search Report mailed on Oct. 28, 2010, for European Patent Application No. 10164673.5, filed on Mar. 14, 2008 (10 pages).

Farkas et al., "A neuronal C5a receptor and an associated apoptotic signal transduction pathway," *J. Physiol.* 507: 679-687, 1998.

Felderhoff-Mueser et al., "Pathways leading to apoptotic neurodegeneration following trauma to the developing rat brain," *Neurobiol. Dis.* 11: 231-245, 2002.

Final Office Action dated Aug. 10, 2012 in U.S. Appl. No. 11/843,617 (9 pages).

Friedlander, "Apoptosis and caspases in neurodegenerative diseases," *N. Engl. J. Med.* 348: 1365-1375, 2003.

Gaetz, "The neurophysiology of brain injury," *Clin. Neurophysiology* 115: 4-18, 2004.

Ghajar, "Traumatic brain injury," *Lancet* 356: 923-929, 2000.

Hicks et al., "Vaccinia virus complement control protein enhances functional recovery after traumatic brain injury," *J. Neurotrauma* 19: 705-714, 2002.

International Preliminary Report on Patentability issued on Nov. 30, 2007, for International Application No. PCT/US2006/020460, filed on May 26, 2006 (5 pages).

International Search Report mailed on Aug. 29, 2006, for International Application No. PCT/US2006/020460, filed on May 26, 2006 (3 pages).

Kaczorowski et al., "Effect of soluble complement receptor-1 on neutrophil accumulation after traumatic brain injury in rats," *J. Cerb. Blood Flow Metab.* 15: 860-864, 1995.

Keeling et al., "Local neutrophil influx following lateral fluid-percussion brain injury in rats is associated with accumulation of complement activation fragments of the third component (C3) of the complement system," *J. Neuroimmunol.* 105: 20-30, 2000.

Kossman et al., "Elevated levels of the complement components C3 and factor B in ventricular cerebrospinal fluid of patients with traumatic brain injury," *J. Neuroimmunol.* 73: 63-69, 1997.

Kyrkanides et al., "Enhanced glial activation and expression of specific CNS inflammation-related molecules in aged versus young rats following cortical stab injury," *J. Neuroimmunol.* 119: 269-277, 2001.

Marciano et al., "Neuron-specific mRNA complexity responses during hippocampal apoptosis after traumatic brain injury," *J. Neurosci.* 24: 2866-2876, 2004.

Marshall et al., "A new classification of head injury based on computerized tomography," *J. Neurosurg.* 75: S14-S20, 1991.

McArthur et al., "Moderate and severe traumatic brain injury: epidemiologic, imaging and neuropathologic perspectives," *Brain Pathol.* 14: 185-194, 2004.

Mohamad et al., "Mitochondrial Apoptotic Pathways," *Biocell.* 29: 149-161, 2005.

Morgan and Gasque, "Expression of complement in the brain: role in health and disease," *Immunol. Today* 17: 461-466, 1996.

Non-Final Office Action dated Jan. 13, 2010 in U.S. Appl. No. 11/057,047 (13 pages).

Ohlsson et al., "Complement activation following optic nerve crush in the adult rat," *J. Neurotrauma* 20: 895-904, 2003.

Pillay et al., "Administration of vaccinia virus complement control protein shows significant cognitive improvement in a mild injury model," *Ann. N.Y. Acad. Sci.* 1056: 450-461, 2005.

Qiu et al., "Upregulation of the fas receptor death-inducing signaling complex after traumatic brain injury in mice and humans," *J. Neurosci.* 22: 3504-3511, 2002.

Rader et al., "A phage display approach for a rapid antibody humanization: designed combinatorial V gene libraries," *Proc. Natl. Acad. Sci. USA* 95: 8910-8915, 1998.

Raghupathi et al., "BCL-2 overexpression attenuates cortical cell loss after traumatic brain injury in transgenic mice," *J. Cereb. Blood Flow Metab.* 18: 1259-1269, 1998.

Raghupathi et al., "Mild traumatic brain injury induces apoptotic cell death in the cortex that is preceded by decreases in cellular Bcl-2 immunoreactivity," *Neuroscience* 110: 605-616, 2002.

Raghupathi et al., "Temporal alterations in cellular bax: Bcl-2 ratio following traumatic brain injury in the rat," *J. Neurotrauma* 20: 421-435, 2003.

Raghupathi, "Cell death mechanisms following traumatic brain injury," *Brain Pathol.* 14: 215-222, 2004.

Ramer et al., "Setting the stage for functional repair of spinal cord injuries: a cast of thousands," *Spinal Cord* 43: 134-161, 2005.

Rancan et al., "Central nervous system-targeted complement inhibition mediates neuroprotection after closed head injury in transgenic mice," *J. Cereb. Blood Flow Metab.* 23: 1070-1074, 2003.

Rebhun et al., "Proteins of the complement system and acute phase reactants in sera of patients with spinal cord injury," *Ann. Allergy* 66: 335-338, 1991.

Reply to Non-Final Office Action dated Apr. 16, 2008 in U.S. Appl. No. 11/057,047 (3 pages).

Reply to Non-Final Office Action dated Aug. 31, 2009 in U.S. Appl. No. 11/057,047 (22 pages).

Reply to Non-Final Office Action dated May 13, 2010 in U.S. Appl. No. 11/057,047 (18 pages).

Reply to Non-Final Office Action dated Jan. 13, 2011 in U.S. Appl. No. 11/057,047 (6 pages).

Reply to Non-Final Office Action dated Apr. 7, 2011 in U.S. Appl. No. 11/843,617 (12 pages).

Reply to Final Office Action dated Aug. 22, 2011 in U.S. Appl. No. 11/843,617 (10 pages).

Reply to Final Office Action dated Oct. 10, 2011 in U.S. Appl. No. 11/843,617 (10 pages).

(56) References Cited

OTHER PUBLICATIONS

Reply to Non-Final Office Action dated Mar. 23, 2012 in U.S. Appl. No. 11/843,617 (10 pages).

Reynolds et al., "Vaccinia virus complement control protein reduces inflammation and improves spinal cord integrity following spinal cord injury," *Ann. NY Acad. Sci.* 1035: 165-178, 2004.

Rink et al., "Evidence of apoptotic cell death after experimental traumatic brain injury in the rat," *Am. J. Pathol.* 147: 1575-1583, 1995.

Roof and Hall, "Gender differences in acute CNS trauma and stroke: neuroprotective effects of estrogen and progesterone," *J. Neurotrauma* 17: 367-388, 2000.

Royo et al., "Pharmacology of traumatic brain injury," *Current Opinion in Pharmacology* 3: 27-32, 2003.

Sambrook et al., "Analysis of genomic DNA by Southern hybridization," in *Molecular Cloning: A Laboratory Manual*, Second Edition, Cold Spring Harbor Labs Press: Cold Spring Harbor, NY, pp. 9.21-9.62, 1989.

Sauerland and Maegele, "A CRASH landing in severe head injury," *Lancet* 364: 1291-1292, 2004.

Schmidt et al., "The Role of neuroinflammation in traumatic brain injury," *Eur. J. Trauma* 30: 135-149, 2004.

Schmidt et al., "Closed head injury—an inflammatory disease?" *Brain Res. Rev.* 48: 388-399, 2005.

Sewell et al., "Complement C3 and C5 play critical roles in traumatic brain cryoinjury: blocking effects on neutrophil extravasation by C5a receptor antagonist," *J. Neuroimmunol.* 155: 55-63, 2004.

Shacka and Roth, "Regulation of neuronal cell death and neurodegeneration by members of the Bcl-2 family: therapeutic Implications," *Curr. Drug Targets CNS Nuerol. Disord.* 4: 25-39, 2005.

Singhrao et al., "Spontaneous classical pathway activation and deficiency of membrane regulators render human neurons susceptible to complement lysis," *Am. J. Pathol.* 157: 905-918, 2000.

Stahel et al., "The role of the complement system in traumatic brain injury," *Brain Res. Rev.* 27: 243-256, 1998.

Stahel et al., "Experimental closed head injury: analysis of neurological outcome, blood-brain barrier dysfunction, intracranial neutrophil infiltration, and neuronal cell death in mice deficient in genes for pro-inflammatory cytokines," *J. Cereb. Blood Flow Metab.* 20: 369-380, 2000.

Stahel et al., "Intracerebral complement C5a receptor (CD88) expression is regulated by TNF and lymphotoxin-60 following closed head injury in mice," *J. Neuroimmunol.* 109: 164-172, 2000.

Stahel et al., "Intrathecal levels of complement-derived soluble membrane attack complex (sC5b-9) correlate with blood-brain barrier dysfunction in patients with traumatic brain injury," *J. Neurotrauma* 18: 773-781, 2001.

Strauss et al., "Common patterns of Bcl-2 family gene expression in two traumatic brain injury models," *Neurotox. Res.* 6: 333-342, 2004.

Teasdale and Jennett, "Assessment of coma and impaired consciousness," *Lancet* 2: 81-84, 1974.

Van Beek et al., "Activation of the complement in the central nervous system: Roles in neurodegeneration and neuroprotection," *Ann. N.Y. Acad. Sci.* 992: 56-71, 2003.

Vos et al., "EFNS guideline on mild traumatic brain injury: report on an EFNS task force," *Eur. J. Neurol.* 9: 207-219, 2002.

Williams et al., "In situ DNA fragmentation occurs in white matter up to 12 months after head injury in man," *Acta Neuropathol.* 102: 581-590, 2001.

Wong et al., "Apoptosis and traumatic brain injury," *Neurocrit Care* 3: 177-182, 2005.

Written Opinion of the International Searching Authority mailed on Aug. 29, 2006, for International Application No. PCT/US2006/020460, filed on May 26, 2006 (4 pages).

Xiong et al., "Formation of complement membrane attack complex in mammalian cerebral cortex evokes seizures and neurodegeneration," *J. Neurosci.* 23: 955-960, 2003.

Yakovlev et al., "Activation of CPP32-like caspases contributes to neuronal apoptosis and neurological dysfunction after traumatic brain injury," *J. Neurosci.* 17: 7415-7424, 1997.

Yao et al., "Progesterone differentially regulates pro- and anti-apoptotic gene expression in cerebral cortex following traumatic brain injury in rats," *J. Neurotrauma* 22: 656-668, 2005.

Yatsiv et al., "Elevated intracranial IL-18 in humans and mice after traumatic brain injury and evidence of neuroprotective effects of IL-18-binding protein after experimental closed head injury," *J. Cereb. Blood Flow Metab.* 22: 971-978, 2002.

Yatsiv et al., "Erythropoietin is neuroprotective, improves functional recovery, and reduces neuronal apoptosis and inflammation in a rodent model of experimental closed head injury," *FASEB J.* 19: 1701-1703, 2005.

Zhang et al., "Bench-to-bedside review: apoptosis/programmed cell death triggered by traumatic brain injury," *Crit. Care* 9: 66-75, 2005.

Cole et al., "Complement regulator loss on apoptotic neuronal cells causes increased complement activation and promotes both phagocytosis and cell lysis," *Mol. Immunol.* 43: 1953-1964, 2006.

Leinhase et al., "Pharmacological complement inhibition at the C3 convertase level promotes neuronal survival, neuroprotective intracerebral gene expression, and neurological outcome after traumatic brain injury," *Exp. Neurol.* 199: 454-464, 2006.

Mukherjee and Zhang, "Allergic asthma: influence of genetic and environmental factors," *J. Biol. Chem.* 286: 32883-32889, 2011.

Ohlsson and Havton, "Complement activation after lumbosacral ventral root avulsion injury," *Neurosci. Lett.* 394: 179-183, 2006.

Extended European Search Report dated May 31, 2011, for European Patent Application No. 10188613.3, filed on Feb. 10, 2005 (10 pages).

Clardy "Complement activation by whole endotoxin is blocked by a monoclonal antibody to factor B," Infect Immun. 62(10): 4549-4555 (1994).

Canadian Office Action for Canadian Application No. 2,561,531 mailed Dec. 7, 2012 (4 pages).

Abe et al., "Contribution of anaphylatoxin C5a to late airway responses after repeated exposure of antigen to allergic rats," *J. Immunol.* 167: 4651-4660, 2001.

Abrahamsen et al., "Differential mediator release from basophils of allergic and non-allergic asthmatic patients after stimulation with anti-IgE and C5a," *Clin. Exp. Allergy* 31: 368-378, 2001.

Becherer et al., "Segment spanning residues 727-768 of the complement C3 sequence contains a neoantigenic site and accommodates the binding of CR1, factor H, and factor B," *Biochemistry* 31: 1787-1794, 1992.

Beste et al., "Small antibody-like proteins with prescribed ligand specificities derived from the lipocalin fold," *Proc. Natl. Acad. Sci. U.S.A.* 96: 1898-1903, 1999.

Bjornson et al., "Complement is activated in the upper respiratory tract during influenza virus infection," *Am. Rev. Respir. Dis.* 143: 1062-1066, 1991.

Blease et al., "Chemokines and their role in airway hyper-reactivity," *Respir. Res.* 1: 54-61, 2000.

Casale et al., "Direct evidence of a role for mast cells in the pathogenesis of antigen-induced bronchoconstriction," *J. Clin. Invest.* 80: 1507-1511, 1987.

Chaney, "Corticosteroids and cardiopulmonary bypass: a review of clinical investigations," *Chest* 121: 921-931, 2002.

Cieslewicz et al., "The late, but not early, asthmatic response is dependent on IL-5 and correlates with eosinophil infiltration," *J. Clin Invest.* 104: 301-308, 1999.

Clark, "Antibodies for therapeutic applications," <http://www.path.cam.ac.uk/~mrc7/humanisation/antibodies.html>, printed Jun. 1, 2002 (5 pages).

Clark, "Antibody Humanisation for Therapeutic Applications," <http://www.path.cam.ac.uk/~mrc7/humanization/index.html>, printed Jun. 1, 2002 (4 pages).

Collard et al., "Complement activation following oxidative stress," *Mol. Immunol.* 36: 941-948, 1999.

Czermak et al., "Complement, cytokines, and adhesion molecule expression in inflammatory reactions," *Proc. Assoc. Am. Physicians* 110: 306-312, 1998.

(56) References Cited

OTHER PUBLICATIONS

Desai et al., "Demonstration of C5 cleaving activity in bronchoalveolar fluids and cells: a mechanism of acute and chronic alveolitis," *J. Exp. Pathol.* 1: 201-216, 1984.

Diaz et al., "Leukocytes and mediators in bronchoalveolar lavage during allergen-induced late-phase asthmatic reactions," *Am. Rev. Respir. Dis.* 139: 1383-1389, 1989.

Declaration of Vernon Michael Holers for U.S. Appl. No. 11/057,047, executed Aug. 31, 2009 (68 pages).

Drouin et al., "Expression of the complement anaphylatoxin C3a and C5a receptors on bronchial epithelial and smooth muscle cells in models of sepsis and asthma," *J. Immunol.* 166: 2025-2032, 2001.

Drouin et al., "A protective role for the fifth complement component (C5) in allergic airway disease," *Am. J. Respir. Crit. Care Med.* 173: 852-857, 2006.

Figueroa and Densen, "Infectious diseases associated with complement deficiencies," *Clin. Microbiol. Rev.* 4: 359-395, 1991.

Frank, "Complement: a brief review," *J. Allergy Clin. Immunol.* 84: 411-420, 1989.

Gerard and Gerard, "Complement in allergy and asthma," *Curr. Opin. Immunol.* 14: 705-708, 2002.

Glovsky et al., "Is complement activation a factor in bronchial asthma?" *Int. Arch. Allergy Immunol.* 118: 330-332, 1999.

Gönczi et al., "The severity of clinical symptoms in ragweed-allergic patients is related to the extent of ragweed-induced complement activation in their sera," *Allergy* 52: 1110-1114, 1997.

Hawlisch et al., "The anaphylatoxins bridge innate and adaptive immune responses in allergic asthma," *Mol. Immunol.* 41: 123-131, 2004.

Hogaboam et al., "Mannose-binding lectin deficiency alters the development of fungal asthma: effects on airway response, inflammation, and cytokine profile," *J. Leukoc. Biol.* 75: 805-814, 2004.

Holgate et al., "The bronchial epithelium as a key regulator of airway inflammation and remodelling in asthma," *Clin. Exp. Allergy* 29: 90-95, 1999.

Höpken et al., "The C5a chemoattractant receptor mediates mucosal defence to infection," *Nature* 383: 86-89, 1996.

Humbles et al., "A role for the C3a anaphylatoxin receptor in the effector phase of asthma," *Nature* 406: 998-1001, 2000.

Irvin et al., "Airways hyperreactivity and inflammation produced by aerosolization of human C5A des arg," *Am. Rev. Respir. Dis.* 134: 777-783, 1986.

Jagels et al., "C3a and C5a enhance granulocyte adhesion to endothelial and epithelial cell monolayers: epithelial and endothelial priming is required for C3a-induced eosinophil adhesion," *Immunopharmacology* 46: 209-222, 2000.

Karp et al., "Identification of complement factor 5 as a susceptibility locus for experimental allergic asthma," *Nat. Immunol.* 1: 221-226, 2000.

Kasamatsu et al., "Experimental acute lung injury in guinea pigs after aerosol challenge with sonicated *Pseudomonas aeruginosa* whole cells," *Arerugi* 42: 1616-1622, English Translation of Abstract Only, 1993 (1 page).

Kodani et al., "Intratracheal administration of anaphylatoxin C5a potentiates antigen-induced pulmonary reactions through the prolonged production of cysteinyl-leukotrienes," *Immunopharmacology* 49: 263-274, 2000.

Köhl et al., "A regulatory role for the C5a anaphylatoxin in type 2 immunity in asthma," *J. Clin. Invest.* 116: 783-796, 2006.

Krug et al., "Complement factors C3a and C5a are increased in bronchoalveolar lavage fluid after segmental allergen provocation in subjects with asthma," *Am. J. Respir. Crit. Care Med.* 164: 1841-1843, 2001.

Kulik et al., "Pathogenic natural antibodies recognizing Annexin IV are required to develop intestinal ischaemia-reperfusion injury and are selected during development in a CR2/CD2—dependent manner," Abstract No. O45, *Abstracts/Mol. Immunology* 45: 4110, 2008.

Lambrecht, "An unexpected role for the anaphylatoxin C5a receptor in allergic sensitization," *J. Clin. Invest.* 116: 628-632, 2006.

Larsen et al., "A differential effect of C5a and C5a des Arg in the induction of pulmonary inflammation," *Am. J. Pathol.* 100: 179-192, 1980.

Lukacs et al., "Complement-dependent immune complex-induced bronchial inflammation and hyperreactivity," *Am. J. Physiol. Lung Cell Mol. Physiol.* 280: L512-L518, 2001.

Maruo et al., "Generation of anaphylatoxins through proteolytic processing of C3 and C5 by house dust mite protease," *J. Allergy Clin. Immunol.* 100: 253-260, 1997.

Matis and Rollins, "Complement-specific antibodies: designing novel anti-inflammatories," *Nat. Med.* 1: 839-842, 1995.

Nagata and Glovsky, "Activation of human serum complement with allergens," *J. Allergy Clin. Immunol.* 80: 24-32, 1987.

Nagy et al., "The development of asthma in children infected with *Chlamydia pneumoniae* is dependent on the modifying effect of mannose-binding lectin," *J. Allergy Clin. Immunol.* 112: 729-734, 2003.

Peng et al., "Contribution of complement component C5 in the development of airway inflammation, maintaining airway hyperresponsiveness and sustaining an ongoing asthmatic attack," Abstract No. 200, *Abstracts/Molecular Immunol.* 41: 292, 2004.

Peng et al., "Blocking intrapulmonary activation of complement cascade on the development of airway hyperresponsiveness: utility in sight?" Abstract LB2, presented at *Scientific Sessions AAAAI 62nd Annual Meeting*, Mar. 3-7, p. 720, 2006.

Peng et al., "Role of C5 in the development of airway inflammation, airway hyperresponsiveness, and ongoing airway response," *J. Clin. Invest.* 115: 1590-1600, 2005.

Robbins et al., "Complement activation by cigarette smoke," *Am. J. Physiol.* 260: L254-L259, 1991.

Schreiber et al., "Complement anaphylatoxin C5a and C5a receptor are fundamental to neutrophil activation and glomerulonephritis induces by anti-neutrophil cytoplasmic antibodies," Abstract No. O42, *Abstracts/Molecular Immunol.* 45: 4109, 2008.

Sinha et al., "The receptor for complement anaphylatoxin C5a protects against the development of airway hyperresponsiveness in allergic asthma by inhibiting cysteinyl leukotriene pathway," Abstract No. O43, *Abstracts/Molecular Immunol.* 45: 4109, 2008.

Takafuji et al., "Degranulation from human eosinophils stimulated with C3a and C5a," *Int. Arch. Allergy Immunol.* 104(Suppl 1): 27-29, 1994.

Taube et al., "Inhibition of complement activation decreases airway inflammation and hyperresponsiveness," *Am. J. Respir. Crit. Care Med.* 168: 1333-1341, 2003.

Varsano et al., "Generation of complement C3 and expression of cell membrane complement inhibitory proteins by human bronchial epithelium cell line," *Thorax* 55: 364-369, 2000.

Versey et al., "Activation of complement in relation to disease," *J Clin. Pathol.*, 28, Suppl. (*Assoc. Clin. Pathol*) 6: 38-44, 1975.

Wang et al., "Anti-C5 monoclonal antibody therapy prevents collagen-induced arthritis and ameliorates established disease," *Proc. Natl. Acad. Sci. USA* 92: 8955-8959, 1995.

Winkelstein et al., "The role of C3 as an opsonin in the early stages of infection," *Proc. Soc. Exp. Biol. Med.* 149: 397-401, 1975.

Written Opinion for International Application No. PCT/US05/04346, mailed Jul. 7, 2005 (3 pages).

European Patent Office Communication for European Application No. 10188613.3, dated Oct. 30, 2013 (8 pages).

Leslie, "Complement receptors," Encyclopedia of Life Sciences 1-9 (2001).

* cited by examiner

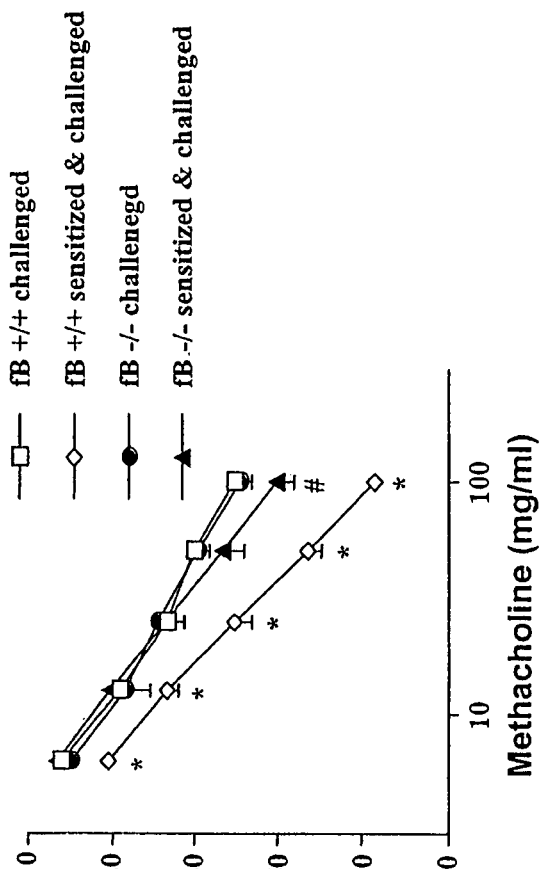
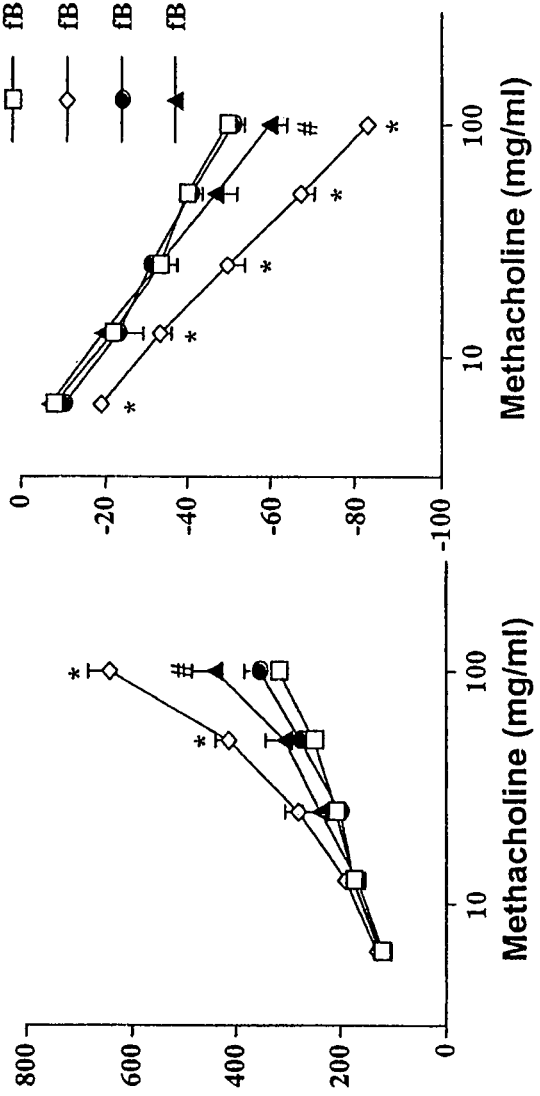
Fig. 4A
Fig. 4B

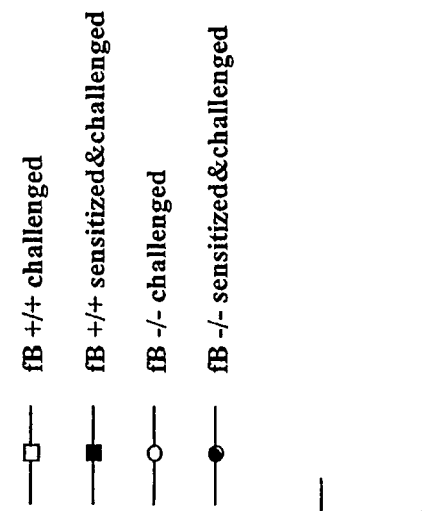
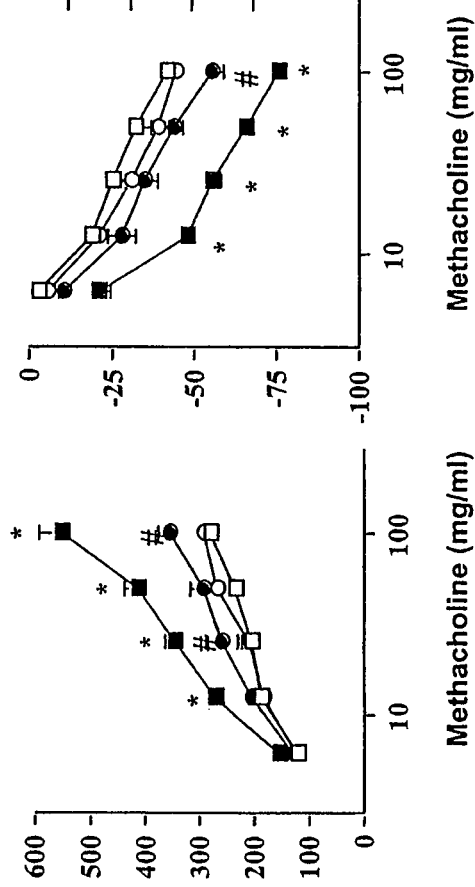
Fig. 6B
Fig. 6A

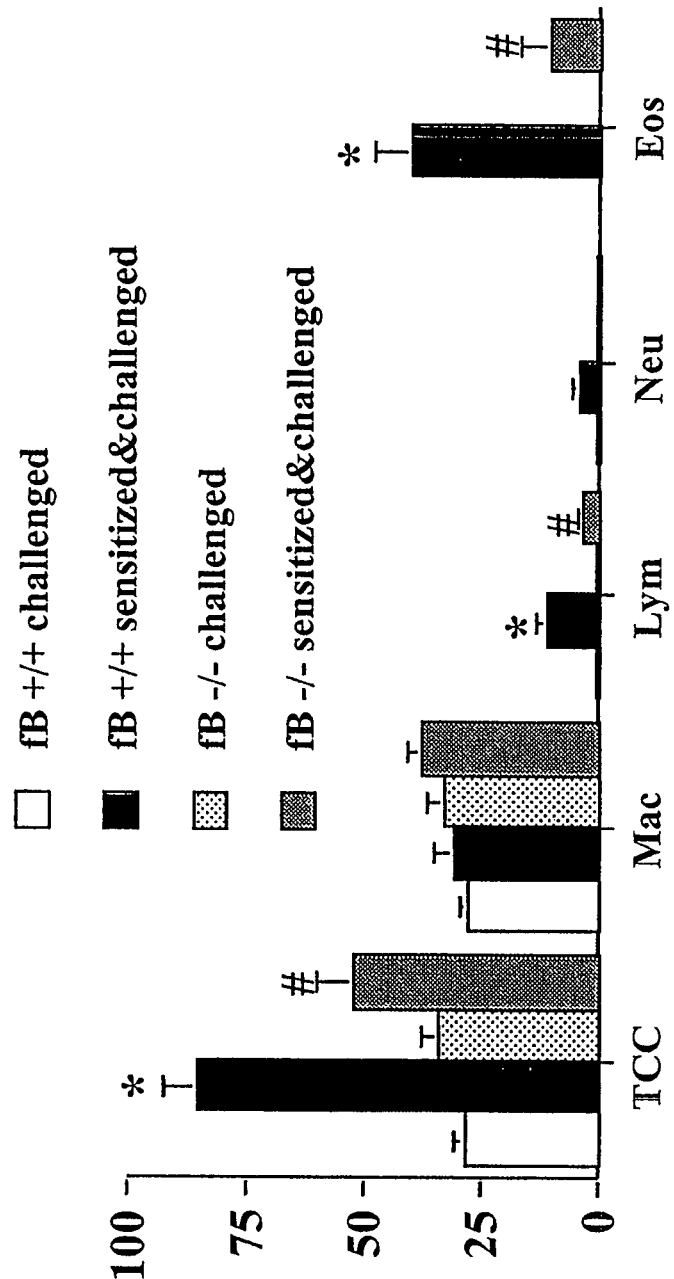

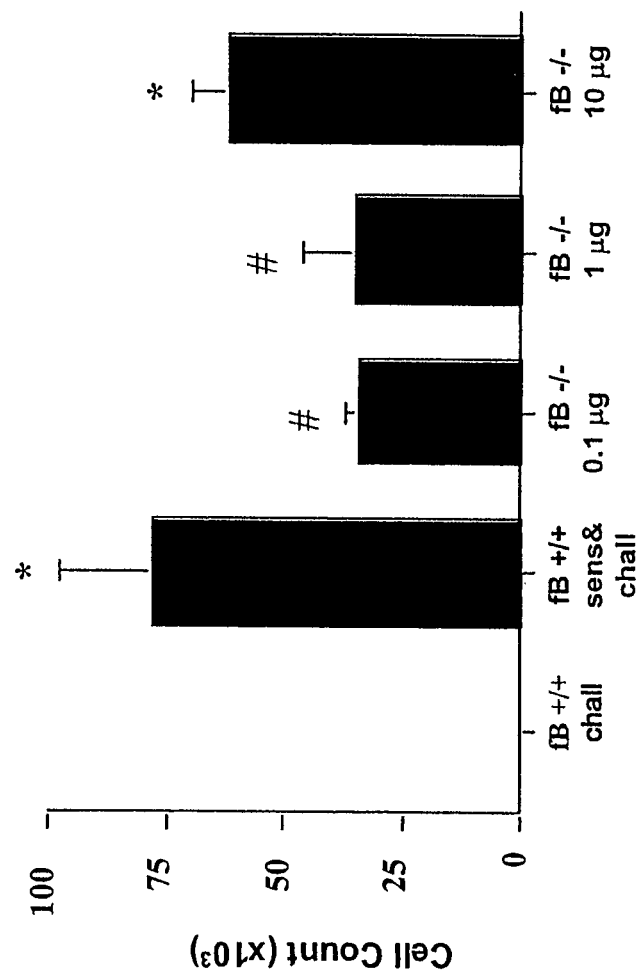

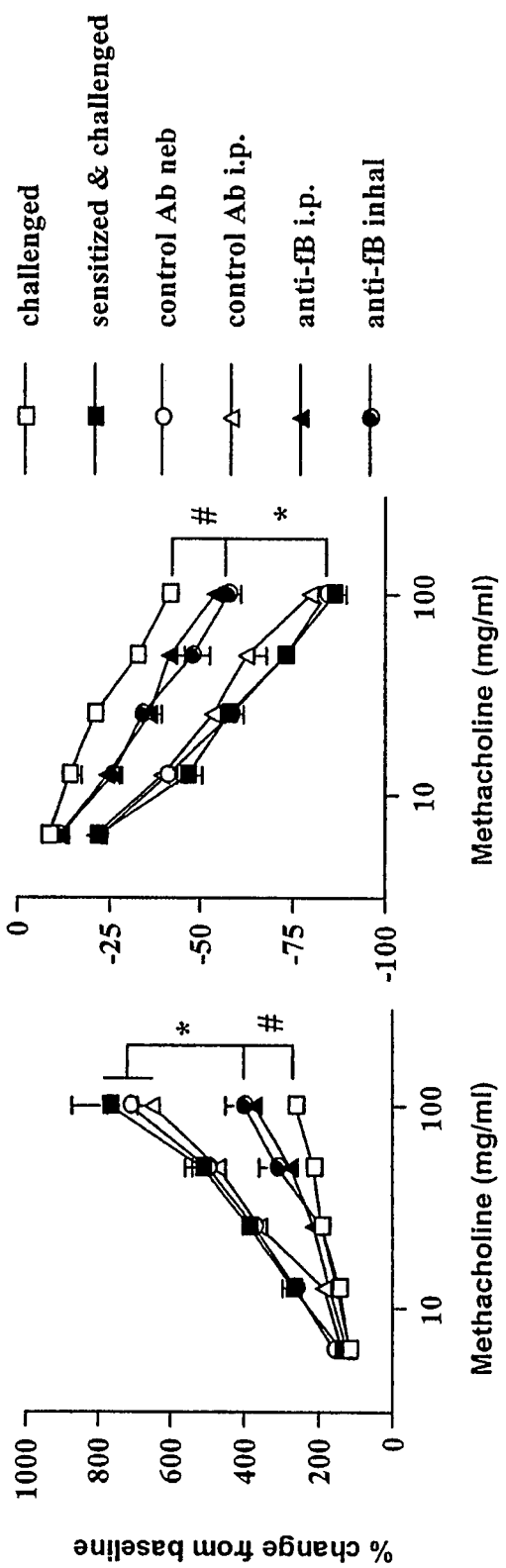

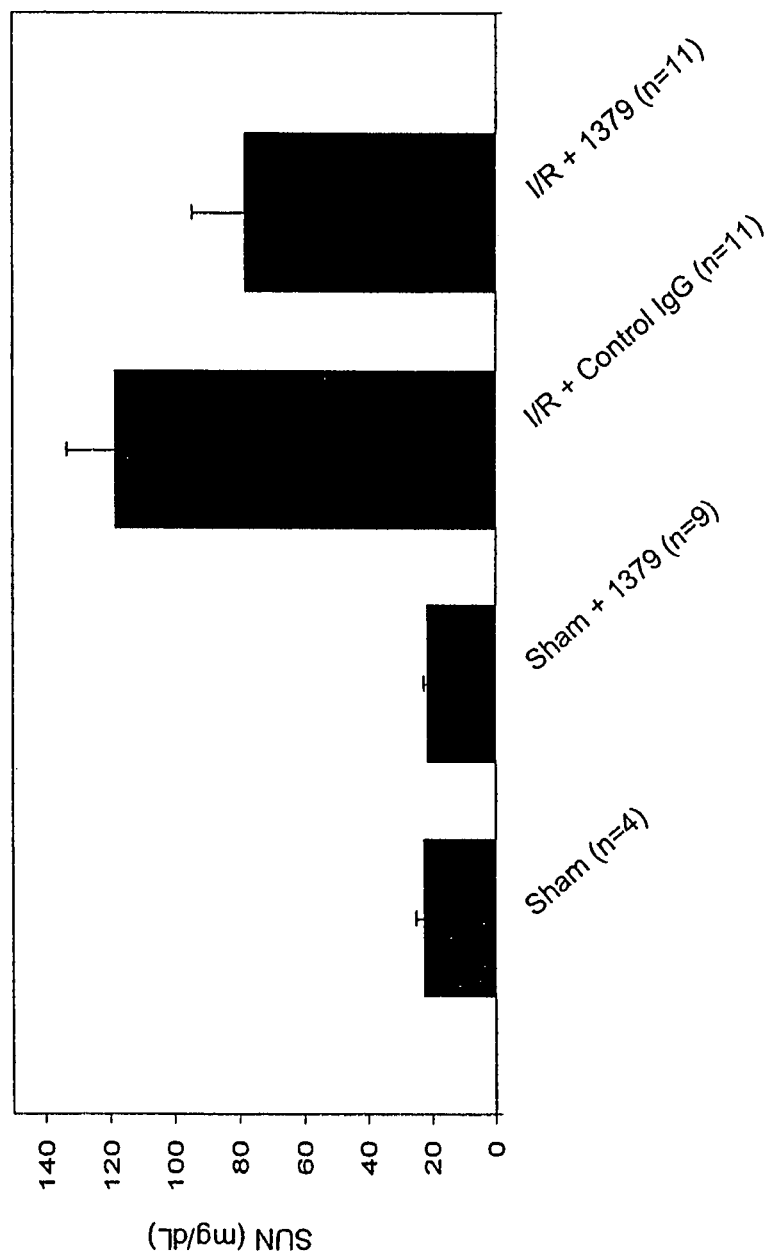

INHIBITION OF FACTOR B, THE ALTERNATIVE COMPLEMENT PATHWAY AND METHODS RELATED THERETO

CROSS-REFERENCE TO RELATED APPLICATIONS

This application is a continuation of U.S. patent application Ser. No. 11/057,047, now U.S. Pat. No. 7,799,082, filed Feb. 10, 2005, which claims priority under 35 U.S.C. §119(e) from U.S. Provisional Application No. 60/543,594, filed Feb. 10, 2004, and from U.S. Provisional Application No. 60/636,239, filed Dec. 14, 2004. U.S. patent application Ser. No. 11/057,047, now U.S. Pat. No. 7,999,082, is a continuation-in-part of PCT Application No. PCT/US2004/015040, filed May 13, 2004, which is published in English and designates United States. The content of each of the above is incorporated herein by reference in their entireties.

GOVERNMENT RIGHTS

This invention was supported, in part, by Grant Nos. AI147469, HL-36577, HL-61005 and AI-31105 each awarded by the National Institutes of Health; and by Grant No. R825702, awarded by the Environmental Protection Agency. The government has certain rights to this invention.

FIELD OF THE INVENTION

This invention generally relates to novel inhibitors of the alternative complement pathway and particularly, novel anti-factor B antibodies. The invention also generally relates to the use of such inhibitors to reduce or prevent airway hyperresponsiveness and airway inflammation and thereby treat diseases in which such conditions play a role.

BACKGROUND OF THE INVENTION

Complement activation occurs primarily by three pathways: the so-called classical pathway, the lectin pathway and the alternative pathway. The key proteins involved in the activation of the alternative pathway are factor B (fB) and factor D (fD). These proteins work in concert to initiate and/or to amplify the activation of C3, which then leads to the initiation of a number of inflammatory events. A third protein, properdin, stabilizes the complex of C3 and factor B but is not absolutely required for the alternative pathway to function. Factor B also helps solubilize immune complexes, has been reported to act as a B cell growth factor and can activate monocytes (Takahashi, 1980; Hall, 1982; Peters, 1988). Factor B-deficient mice (fB−/− mice) have been generated and IgG1 antibody response to T-cell dependent antigens and sensitivity to endotoxic shock appear normal in these mice (Matsumoto, 1997).

The alternative complement pathway is usually initiated by bacteria, parasites, viruses or fungi, although IgA Abs and certain Ig L chains have also been reported to activate this pathway. Alternative pathway activation is initiated when circulating factor B binds to activated C3 (either C3b or $C3H_2O$). This complex is then cleaved by circulating factor D to yield an enzymatically active fragment, C3Bb. C3Bb cleaves C3 generating C3b, which drives inflammation and also further amplify the activation process, generating a positive feedback loop. Both components (factor B and factor D) are required to enable activation of the alternative pathway.

Recent studies have shown that the alternative pathway of complement plays an important role in the pathogenesis of several animal models of disease. Complement activation within the kidney after I/R is mediated almost exclusively by the alternative pathway (Thurman) and the alternative pathway plays a critical role in the development of arthritis. Perhaps most surprisingly, mice deficient in the alternative pathway have been demonstrated to be protected from nephritis in the MRL/lpr model of lupus nephritis (Watanabe) and from anti-phospholipid mediated fetal loss (Girardi), models that would traditionally have been assumed to be mediated by the classical complement pathway.

Several inhibitors have already been developed to inhibit the complement system at various stages of activation (Holers), although specific inhibitors of the alternative pathway have not been widely reported prior to the present invention. PCT Publication WO 01/47963, published Jul. 4, 2001, describes polypeptides from ectoparasitic leeches that inhibit the alternative pathway of complement activation in vitro and have substantially no effect on the complement activation by the classical route. These peptides were shown to bind to factor D; however, no in vivo application of these polypeptides was demonstrated. A reagent with the ability to specifically inhibit the alternative pathway in vivo would theoretically have several advantages compared with existing inhibitors of the complement cascade. First, for models such as renal I/R and antiphospholipid mediated fetal loss, that are primarily mediated by the alternative pathway, such an inhibitor should be equally effective as a pan-complement inhibitor yet should have fewer immunosuppressive side-effects. Although only one human patient with congenital deficiency of factor B has been reported (Densen), studies of gene targeted factor B deficient mice (fB−/−) have not yet demonstrated an immune-modulating effect for this factor (Densen; Matsumoto). Patients with congenital deficiencies of classical pathway components, in contrast, appear to have an increased risk of infection (most commonly *Staphylococcus* and *Streptococcus*). Inhibition of classical pathway components or C3 (common to all of the complement pathways) might also be associated with the autoimmunity (Figueroa), perhaps explaining why factor B deficiency protects MRL/lpr mice from developing glomerulonephritis, but C3 deficiency does not (Watanabe). Thus, inhibition of the alternative pathway may be better tolerated and in some cases more effective than classical pathway complement inhibition.

Allergic asthma is a common syndrome associated with airway inflammation and airway hyperresponsiveness (AHR) (Busse). In patients with allergic asthma exposure to inhaled allergen leads to increase in AHR and airway inflammation and studies have shown increased levels of biologically active fragments derived from the complement C3, C4 and C5 family of proteins, especially C3a (Humbles) and C5a (Krug) in bronchoalveolar lavage (BAL) fluid. This suggests that in these patients, following allergen exposure, activation of the complement pathway through an allergen-induced mechanism occurs in the lung. Animal models have provided further insight in the role of complement for the development of allergic airway disease. Animals deficient in C3 or C3a receptor animals appear protected from the development of allergen induced airway disease (Humbles, Drouin; Bautsch; Walters).

Several different possibilities have been proposed to induce complement activation following allergen exposure. For example, allergen-IgG immune-complexes could trigger activation of the classical pathway and certain antigens may directly activate C3 via the alternative pathway (Kohl). In addition, neutral tryptase released from mast cells or pulmonary macrophages may directly (proteolytically) cleave either C3 or C5 (Schwartz; Mulligan). The three pathways of complement activation (classical, alternative, and lectin) converge at the central complement component C3. Therefore inhibition of C3 activation prevents cleavage into active C3 fragments but also largely reduces the downstream activation of C5 and the release of C5-derived activated fragments (Sahu). Recent studies have shown that inhibition of complement activation during allergen exposure of sensitized animals by using C3 convertase inhibitors, and therefore inhibiting all three activation pathways, reduces the late airway response (Abe) as well as the development of AHR and airway inflammation (Taube). PCT Publication No. WO 2004/022096, published Mar. 18, 2004, describes the inhibition of the complement pathway, preferably through the terminal complement components of C5-C9 that are shared by all pathways, and most preferably through inhibition of C5a.

Currently, therapy for treatment of inflammatory diseases involving AHR, such as moderate to severe asthma and chronic obstructive pulmonary disease, predominantly involves the use of glucocorticosteroids and other anti-inflammatory agents. These agents, however, have the potential of serious side effect, including, but not limited to, increased susceptibility to infection, liver toxicity, drug-induced lung disease, and bone marrow suppression. Thus, such drugs are limited in their clinical use for the treatment of lung diseases associated with airway hyperresponsiveness. The use of anti-inflammatory and symptomatic relief reagents is a serious problem because of their side effects or their failure to attack the underlying cause of an inflammatory response. There is a continuing requirement for less harmful and more effective reagents for treating inflammation. Thus, there remains a need for processes using reagents with lower side effect profiles, less toxicity and more specificity for the underlying cause of allergic airway diseases such as asthma and the condition known as AHR.

SUMMARY OF THE INVENTION

One embodiment of the present invention relates to an isolated antibody or antigen-binding fragment thereof that selectively binds to factor B within the third short consensus repeat (SCR) domain, wherein the antibody prevents formation of a C3bBb complex. In one aspect, the antibody or antigen-binding fragment thereof binds to factor B and prevents or inhibits cleavage of factor B by factor D. In another aspect, the antibody or antigen-binding fragment binds to the third short consensus repeat (SCR) domain of human factor B. In another aspect, the antibody or antigen-binding fragment binds to an epitope in the third SCR domain of factor B selected from: (a) an epitope of factor B that includes at least a portion of human factor B (SEQ ID NO:2) comprising from about position Tyr139 to about position Ser185, or equivalent positions thereto in a non-human factor B sequence; (b) an epitope of factor B that includes at least a portion of human factor B (SEQ ID NO:2) comprising from about position Tyr139 to about position Ser141, or equivalent positions thereto in a non-human factor B sequence; (c) an epitope of factor B that includes at least a portion of human factor B (SEQ ID NO:2) comprising from about position Glu182 to about position Ser185, or equivalent positions thereto in a non-human factor B sequence; or (d) an epitope of factor B that includes at least a portion of human factor B (SEQ ID NO:2) comprising any one or more of the following positions or their equivalent positions in a non-human factor B sequence: Tyr139, Cys 140, Ser141, Glu182, Gly184, or Ser185. In yet another aspect, the antibody or antigen binding fragment thereof selectively binds to an epitope in the third SCR domain of factor B (SEQ ID NO:2) comprising one or more of the following amino acid positions or their equivalent positions in a non-human factor B sequence: Ala137, Tyr139, Ser141, Glu182, Ser185, Thr189, Glu190, and Ser192. In another aspect, the antibody or antigen binding fragment thereof selectively binds to an epitope in the third SCR domain of factor B (SEQ ID NO:2) comprising the following amino acid positions or their equivalent positions in a non-human factor B sequence: Ala137, Tyr139, Ser141, Glu182, Ser185, Thr189, Glu190, and Ser192. In yet another aspect, the antibody or antigen binding fragment thereof selectively binds to an epitope in the third SCR domain of factor B (SEQ ID NO:2) consisting of the following amino acid positions or their equivalent positions in a non-human factor B sequence: Ala137, Tyr139, Ser141, Glu182, Ser185, Thr189, Glu190, and Ser192. The antibody or antigen-binding fragment can binds to a non-linear epitope within the three-dimensional structure of a portion of the third SCR domain of factor B, wherein the portion is defined by at least amino acid positions Ala137-Ser192 of SEQ ID NO:2 or equivalent positions in a non-human factor B sequence. In another aspect, the antibody or antigen binding fragment thereof selectively binds to factor B from multiple mammalian species (e.g., human and an animal selected from the group consisting of non-human primate, mouse, rat, pig, horse and rabbit). The antibody or antigen-binding fragment can be of a non-complement activating isotype or subclass, can be a monoclonal antibody, a humanized antibody, a bispecific antibody, or a monovalent antibody. The antigen binding fragment can include an Fab fragment. In a preferred embodiment, the antibody is the monoclonal antibody 1379 (produced by ATCC Deposit No. PTA-6230).

Another embodiment of the present invention relates to an isolated antibody or antigen-binding fragment thereof that selectively binds to factor B from multiple mammalian species, wherein the antibody prevents formation of a C3bBb complex. In one aspect, the antibody or antigen binding fragment thereof selectively binds to factor B from human and an animal selected from the group consisting of non-human primate, mouse, rat, pig, horse and rabbit. In one aspect, the antibody is of a non-complement activating isotype or subclass. In another aspect, the antibody is a monoclonal antibody. In another aspect, the antigen binding fragment is an Fab fragment.

Yet another embodiment of the present invention relates to antigen binding polypeptide that selectively binds to factor B within the third short consensus repeat (SCR) domain, wherein the antigen binding polypeptide prevents formation of a C3bBb complex, or an antigen binding polypeptide that selectively binds to factor B from multiple mammalian species, wherein the antigen binding polypeptide prevents formation of a C3bBb complex.

Another embodiment of the present invention relates to an isolated antibody or antigen binding fragment thereof that selectively binds to factor B, wherein the antibody or fragment thereof competitively inhibits the specific binding of the monoclonal antibody 1379 (produced by ATCC Deposit No. PTA-6230) to human factor B, and wherein, when the antibody or antigen binding fragment thereof binds to human factor B, the ability of monoclonal antibody 1379 to inhibit the alternative complement pathway is inhibited. In one aspect, the antibody or antigen binding fragment thereof competitively inhibits the binding of monoclonal antibody 1379 to human factor B, where comparative binding specificity is determined by antibody-antibody competition assay in the presence of human factor B.

Another embodiment of the present invention relates to an isolated antibody or fragment thereof that selectively binds to human factor B, wherein the isolated antibody or fragment thereof competitively inhibits the specific binding of a second antibody or antigen binding fragment thereof to human factor B, and wherein the second antibody or antigen binding fragment thereof binds to the third SCR domain of human factor B.

Also included in the present invention are compositions comprising any of the above-described antibodies, antigen binding fragments, or antigen binding polypeptides.

Yet another embodiment of the present invention relates to a method to reduce or prevent airway hyperresponsiveness (AHR) or airway inflammation in an animal. The method includes the step of administering an antibody or antigen binding fragment thereof as described above to an animal that has, or is at risk of developing, airway hyperresponsiveness associated with inflammation or airway inflammation. In one aspect, the antibody or antigen binding fragment is administered by a route selected from the group consisting of oral, nasal, topical, inhaled, intratracheal, transdermal, rectal and parenteral routes. In another aspect, the antibody or antigen binding fragment is administered to the animal in an amount effective to measurably reduce airway hyperresponsiveness in the animal as compared to prior to administration of the antibody or antigen binding fragment. In another aspect, the antibody or antigen binding fragment is administered to the animal in an amount effective to measurably reduce airway hyperresponsiveness in the animal as compared to a level of airway hyperresponsiveness in a population of animals having inflammation wherein the antibody or antigen binding fragment was not administered. In one aspect, administration of the antibody or antigen binding fragment decreases the animal's responsiveness to methacholine or to histamine. In another aspect, the antibody or antigen binding fragment is administered with a pharmaceutically acceptable carrier selected from the group consisting of: a dry, dispersible powder; anhydrous ethanol; small capsules; liposomes; a nebulized spray; and an injectable excipient. In another aspect, the antibody or antigen binding fragment is administered in a carrier or device selected from the group consisting of: anhydrous ethanol; a dry powder inhalation system; ultrasonic inhalation system; a pressurized metered dose inhaler; and a metered solution device. In yet another aspect, the antibody or antigen binding fragment is administered to said mammal in conjunction with an agent selected from the group consisting of: corticosteroids, β-agonists (long or short acting), leukotriene modifiers, antihistamines, phosphodiesterase inhibitors, sodium cromoglycate, Nedocromil, theophylline, cytokine antagonists, cytokine receptor antagonists, anti-IgE, and inhibitors of T cell function. In yet another aspect, the airway hyperresponsiveness or airway inflammation is associated with a disease selected from the group consisting of asthma, chronic obstructive pulmonary disease (COPD), allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus (RSV) infection, parainfluenza virus (PIV) infection, rhinovirus (RV) infection and adenovirus infection. In one aspect, the airway hyperresponsiveness is associated with allergic inflammation. The method of the present invention can be administered, in a preferred embodiment, to mammals, and more preferably, to humans.

Another embodiment of the present invention relates to a method to reduce or prevent airway hyperresponsiveness (AHR) or airway inflammation in an animal. The method includes the step of administering a reagent that selectively inhibits the alternative complement pathway to an animal that has, or is at risk of developing, airway hyperresponsiveness associated with inflammation or airway inflammation.

BRIEF DESCRIPTION OF THE FIGURES

The patent or application file contains at least one drawing executed in color. Copies of this patent or patent application with color drawing will be provided by the Office upon request and payment of the necessary fee.

FIG. 4A is a line graph for airway resistance ($R_L$) that shows that allergen-sensitized and challenged fB+/+ mice showed increased responsiveness to methacholine as compared to challenged only fB+/+ mice, whereas fB−/− mice demonstrated a significantly lower response to methacholine.

FIG. 4B is a line graph for dynamic compliance (Cdyn) showing that allergen-sensitized and challenged fB+/+ mice showed increased responsiveness to methacholine as compared to challenged only fB+/+ mice, whereas fB−/− mice demonstrated a significantly lower response to methacholine.

FIG. 6A is a line graph for airway resistance ($R_L$) showing that ragweed sensitized and challenged fB−/− mice showed a decrease in responsiveness to methacholine, whereas fB+/+ developed a strong response to methacholine.

FIG. 6B is a line graph for dynamic compliance (Cdyn) showing that ragweed sensitized and challenged fB−/− mice showed a decrease in responsiveness to methacholine, whereas fB+/+ developed a strong response to methacholine.

FIG. 6C is a bar graph characterizing BAL fluid and lung tissue and showing that airway inflammation in BAL fluid was reduced in ragweed sensitized and challenged fB−/− mice compared to fB+/+ mice.

FIG. 7B is a bar graph showing that administration of factor B reconstitutes the ability to develop AHR and airway inflammation in fB−/− mice.

FIG. 8A is a line graph for airway resistance ($R_L$) that shows that both systemic and nebulized administration of a factor B-neutralizing antibody inhibits the development of AHR in sensitized and challenged mice.

FIG. 8B is a line graph for dynamic compliance (Cdyn) that shows that both systemic and nebulized administration of an factor B-neutralizing antibody inhibits the development of AHR in sensitized and challenged mice.

FIG. 13 is a bar graph showing that mice that were pretreated with 1379 demonstrated milder increases in serum urea nitrogen after 24 hours of reperfusion when compared to wild-type controls.

DETAILED DESCRIPTION OF THE INVENTION

Figure 1:
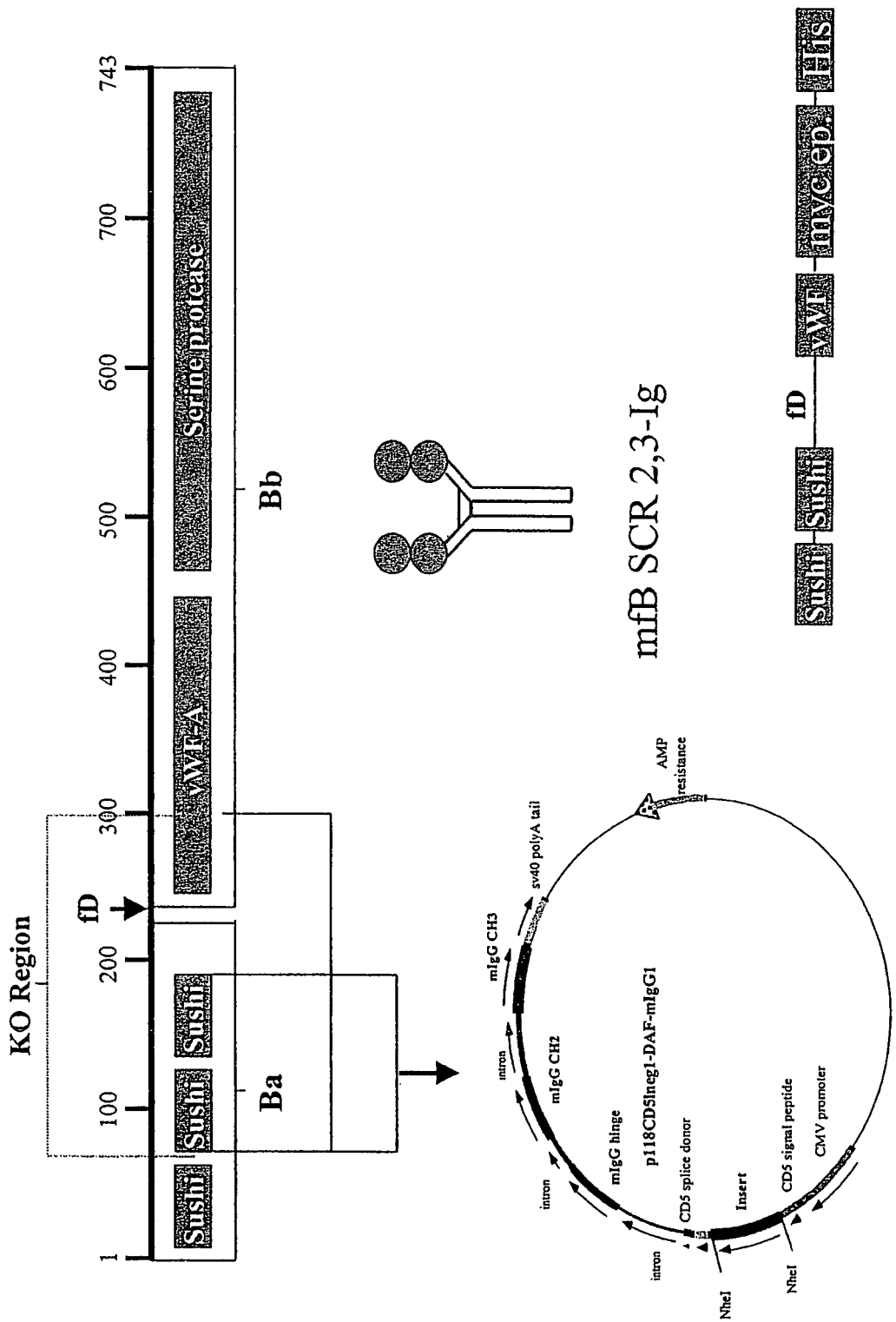
FIG. 1 is a schematic diagram showing the construction of a factor B-Ig fusion protein.

One embodiment of the present invention relates to the provision of novel factor B antibodies that selectively block the alternative complement pathway, and the use of such antibodies to inhibit the alternative complement pathway in any condition or disease where such inhibition is desired, useful or anticipated to be useful. Specifically, given the great potential therapeutic benefit of an inhibitor specific for the alternative complement pathway for use in methods of treatment for many diseases, the present inventors have developed several novel, inhibitory monoclonal antibodies directed against factor B. Several of these antibodies have been characterized, and one of these antibodies has been characterized in great detail. This antibody has been tested in vitro as well as in vivo in both a well-accepted model of allergic inflammation and asthma, and in a model of renal ischemia-reperfusion injury, which is generally applicable to ischemia-reperfusion injury. To produce such antibodies, gene-targeted factor B deficient mice (fB−/−) were injected with a fusion protein comprised of the second and third short consensus repeat (SCR) domains of factor B linked to an immunoglobulin. Mice were screened for an immune response to factor B, and spleen cells from one of the injected mice were fused to myeloma cells. One of the resulting hybridomas, named 1379, produces an $IgG_1$ antibody that inhibits alternative complement pathway activation in vitro and in vivo, although the present inventors have produced and characterized multiple monoclonal antibodies with the ability to inhibit the alternative complement pathway (see Table 4). The 1379 antibody (also referred to herein as mAb1379) inhibits alternative pathway activation in serum from multiple animal species including, mice, rats, humans, baboons, rhesus monkeys, cyno monkeys, pigs, rabbits, and horses. Fab fragments made from this antibody also resulted in complete inhibition of the alternative pathway. The inventors have also shown that the antibody can completely inhibit the lysis of erythrocytes by human serum, thus confirming the ability of this reagent to completely block alternative complement pathway activation. Epitope mapping was used to demonstrate that this antibody binds to factor B within the third short consensus repeat (SCR) domain, and the antibody prevented formation of the C3bBb complex. A detailed description of the epitope recognized by this antibody is provided below. Therefore, one embodiment of the present invention is directed to selective inhibitors of the alternative complement pathway, and particularly these novel factor B antibodies, that have broad species reactivity, demonstrated in vitro and in vivo efficacy, and are highly effective therapeutic tools for use in any of a variety of conditions and diseases wherein selective inhibition of the complement pathway is be useful, necessary and/or preferred (e.g., conditions associated with airway hyperresponsiveness and airway inflammation (see below), ischemia-reperfusion injury, etc.). These antibodies can also be humanized or otherwise manipulated to reduce potential side effects from the immune system and are therefore a valuable new therapeutic reagent.

The antibodies that have been produced by the present inventors recognize a site on factor B that is shared among several mammalian species (including humans) in which preclinical proof-of-principle experiments are performed, thus allowing discoveries in models of human disease to be readily translated into human therapies. Prior to the present invention, the inventors are not aware of any other antibody against factor B that exhibits the broad species inhibition of the protein as the does the antibody of the present invention. Therefore, the present inventors have also identified a unique site on factor B against which new inhibitory reagents can be developed. Identification of factor B and the other proteins in the alternative complement pathway as specific therapeutic targets provides both a rational therapeutic strategy as well as lead compounds that can be pursued to treat inflammatory diseases of the airways and other diseases. There are advantages in selectively blocking the alternative pathway. For example, C4−/− mice (mice lacking the C4 complement component that is generic to the classical, alternative and lectin complement pathways), but not fB−/− (factor B deficient) mice, appear more susceptible to experimental bacterial infection, suggesting that by leaving the classical pathway intact, an inhibitor of the alternative pathway poses less risk for serious infection. Blockade of the classical pathway may also result in autoimmunity and patients with congenital deficiencies of classical pathway components have an increased risk of infection and autoimmunity. Selective inhibition of the alternative pathway prevents generation of C3-derived ligands for the C3a receptor as well as for complement receptors 1-4 and C5a. The effects of blocking of the alternative pathway may in fact be more direct, due to as yet poorly characterized receptors for the Ba or Bb activation products of factor B that are generated during the activation process.

Another embodiment of the present invention relates to a surprising discovery by the present inventors that activation of the complement cascade through the alternative pathway is critical, and in fact necessary and sufficient, for the development of airway hyperresponsiveness and airway inflammation. More particularly, the present inventors disclose herein the discovery that inhibition of the alternative pathway, but not the classical complement pathway, prevents airway hyperresponsiveness and reduces airway inflammation. The inventors demonstrate this discovery using mice deficient in factor B (i.e., via knock out technology) and by inhibition of factor B with monoclonal antibodies (delivered both systemically and by aerosol). The inventors therefore disclose herein the selective inhibition of the alternative complement pathway by this or by any other means (e.g., by a deficiency or inhibition of factor D or properdin), to inhibit airway hyperresponsiveness and airway inflammation. The present inventors have demonstrated that factor B is necessary for the induction of experimental asthma. Importantly, factor B is essential to the challenge (or effector) phase of this model, and inhalation of a monoclonal antibody that selectively binds to factor B into the lung or administered systemically blocks the development of airway hyperresponsiveness (AHR) and airway inflammation associated with allergic inflammatory disease, as exemplified in an experimental asthma model. Moreover, the present inventors have discovered that this inhibition is specifically achieved via the inhibition of the alternative complement pathway, since additional results showed that C4 knockout (C4−/−) mice were not protected from AHR, whereas factor B knockout (fB−/−) mice were protected from AHR in this model system. Therefore, the present inventors have discovered that inhibition of the alternative complement pathway (by any means) is necessary and sufficient to inhibit AHR and airway inflammation and thereby treat or prevent conditions and diseases related thereto. Furthermore, the inventors show that inhibition of the classical complement pathway is not required for inhibition of AHR or airway inflammation and therefore, as discussed above, undesirable consequences associated with inhibition of the classical complement pathway can be avoided following the teachings of the present invention.

Factor B Antibodies

Accordingly, a first embodiment of the present invention relates to an antibody or an antigen binding fragment thereof that selectively inhibits the alternative complement pathway and particularly, a factor B antibody. Similarly, an antigen binding polypeptide with the same specificity is also particularly preferred for use in the present invention. In one aspect, the antibody selectively binds to the protein of the alternative complement pathway in a manner such that the protein is inhibited or prevented from binding to another protein with which it normally (under natural or physiological conditions) interacts. In another aspect, the antibody selectively binds to the protein in a manner such that the protein is inhibited or prevented from activating another protein with which it normally interacts, even though the protein may at least partially bind to the other protein. Particularly preferred antibodies and antigen binding fragments thereof for use in selective inhibition of the alternative complement pathway include the factor B antibodies described herein, and particularly, the mAb1379 antibody described in detail herein.

Antibodies (and antigen binding fragments thereof) that selectively bind to factor B and inhibit the alternative complement pathway according to the invention are described and exemplified in detail herein. In one embodiment, the antibody or antigen binding fragment thereof binds to a conserved binding surface or epitope of such a protein (e.g., factor B) that is conserved among animal species, and particularly mammalian, species (i.e., the antibody is cross-reactive with the protein from two or more different mammalian species). In particular, the present invention includes an antibody that binds to factor B from at least two, and preferably, several different mammalian species, including, but not limited to, human, non-human primate, mouse, rat, pig, horse and rabbit. Preferably, the present invention includes an antibody that binds to factor B from human and at least one additional animal species, and preferably, at least one additional mammalian species, including, but not limited to, non-human primate, mouse, rat, pig, horse and rabbit. In one embodiment, the antibody or antigen binding fragment thereof binds to the third short consensus repeat (SCR) of factor B. In one embodiment, the antibody or antigen binding fragment thereof binds to a region of factor B that prevents the cleavage of factor B by factor D. In one embodiment, the antibody is a monoclonal antibody. In one embodiment, the antibody is the antibody referred to herein as 1379 (i.e., the antibody produced by the hybridoma cell line of the same number, also having ATCC Deposit Designation PTA-6230), or an antigen binding fragment thereof.

The hybridoma described herein as 1379 (or mAb 1379) was deposited on Sep. 21, 2004, with the American Type Culture Collection (ATCC, located at 10801 University Blvd, Manassas, Va. 20110-2209), under the terms of the Budapest Treaty on the International Recognition of The Deposit of Microorganisms For the Purposes of Patent Procedure, and has received ATCC Deposit Designation PTA-6230.

According to the present invention, the minimum size of a protein, portion of a protein (e.g. a fragment, portion, domain, etc.), or region or epitope of a protein, is a size sufficient to serve as an epitope or conserved binding surface for the generation of an antibody or as a target in an in vitro assay. In one embodiment, a protein of the present invention is at least about 4, 5, 6, 7 or 8 amino acids in length (e.g., suitable for an antibody epitope or as a detectable peptide in an assay), or at least about 25 amino acids in length, or at least about 50 amino acids in length, or at least about 100 amino acids in length, or at least about 150 amino acids in length, and so on, in any length between 4 amino acids and up to the full length of a protein or portion thereof or longer, in whole integers (e.g., 8, 9, 10, . . . 25, 26, . . . 500, 501, . . . ).

The nucleotide sequence for the gene and coding region encoding human factor B and other complement proteins, as well as the amino acid sequence of such proteins, are well known in the art. For example, the gene encoding human factor B and other complement proteins is found in NCBI Database Accession No. NG_000013. The coding sequence for factor B is found in NCBI Database Accession No. NM_001710 and the amino acid sequence for factor B preproprotein is found in NCBI Database Accession No. NP_001701 or P00751. The amino acid sequence for NCBI Database Accession No. P00751, which is a human preproprotein factor B sequence, is represented herein by SEQ ID NO:1. Sequences from other animal species are also known in the art. By way of comparison, in the mouse factor B sequence (e.g., see NCBI Database Accession No. P04186, represented herein by SEQ ID NO:6), the third SCR domain is located at positions 160-217 of this 761 amino acid preprotein, and the mature murine factor B protein spans positions 23-761 of SEQ ID NO:6.

The human factor B preprotein represented by SEQ ID NO:1 is a 764 amino acid protein with a signal peptide spanning from amino acid positions 1-25. The mature chain of factor B corresponds to positions 26-764 of SEQ ID NO:1 and is represented herein by SEQ ID NO:2. The three SCR regions of human factor B are represented herein by SEQ ID NO:3 (SCR1, also known as Sushi 1, spanning from about position 35 to about position 100 of SEQ ID NO:1 or from about position 5 to about position 75 of SEQ ID NO:2), SEQ ID NO:4 (SCR2, also known as Sushi 2, spanning from about position 101 to about position 160 of SEQ ID NO:1 or from about position 76 to about position 135 of SEQ ID NO:2), and SEQ ID NO:5 (SCR3, also known as Sushi 3, spanning from about position 163 to about position 220 of SEQ ID NO:1 or from about position 138 to about position 195 of SEQ ID NO:2).

Based on the epitope mapping of an exemplary antibody of the invention using the fragments described by Hourcade, 1995, *J. Biol. Chem.* (see Examples), in one preferred embodiment, an anti-factor B antibody of the present invention preferably binds to an epitope or conserved binding surface within or containing a part of the third SCR domain, and more preferably, to an epitope of human factor B that includes at least a portion of the sequence comprising from about position Tyr139 to about position Ser185 with respect to the mature factor B protein (SEQ ID NO:2), to an epitope of human factor B that includes at least a portion of the sequence comprising from about position Tyr139 to about position Ser141 with respect to the mature factor B protein (SEQ ID NO:2), to an epitope of human factor B that includes at least a portion of the sequence comprising from about position Glu 182 to about position Ser185 with respect to the mature factor B protein (SEQ ID NO:2), to an epitope of factor B that includes at least a portion of human factor B (SEQ ID NO:2) comprising any one or more of the following positions or their equivalent positions in a non-human factor B sequence: Tyr139, Cys 140, Ser141, Glu182, Gly184, or Ser185, or to an epitope of factor B that includes at least a portion of the equivalent positions with respect to non-human animal species. One of skill in the art can readily align the sequence of human factor B with the sequence of factor B from another animal species and determine the positions of the SCR regions and the specific portions of the third SCR regions corresponding to the amino acid positions above. For example, two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174:247-250, incorporated herein by reference in its entirety.

Based on additional epitope modeling and mapping of an exemplary antibody of the invention, in another preferred embodiment, an anti-factor B antibody of the present invention preferably binds to an epitope (conserved binding surface) within or containing a part or portion of the third SCR domain of factor B that includes at least one or more of the following amino acid positions, with respect to SEQ ID NO:2, or their equivalent positions in a non-human factor B sequence: A137, Y139, S141, E182, S185, T189, E190, and S192. In one aspect of the invention, the epitope is within or containing a part of portion of the third SCR domain of factor B that includes all or substantially all of (at least five, six, or seven of) the following amino acid positions of SEQ ID NO:2, or their equivalent positions in a non-human factor B sequence: Ala137, Tyr139, Ser141, Glu182, Ser185, Thr189, Glu190, and Ser192. In yet another aspect, the epitope recognized by an anti-factor B antibody of the present invention is within or contains a part or portion of the third SCR domain of factor B consisting of the following amino acid positions of SEQ ID NO:2, or their equivalent positions in a non-human factor B sequence: Ala137, Tyr139, Ser141, Glu182, Ser185, Thr189, Glu190, and Ser192.

Figure 11:
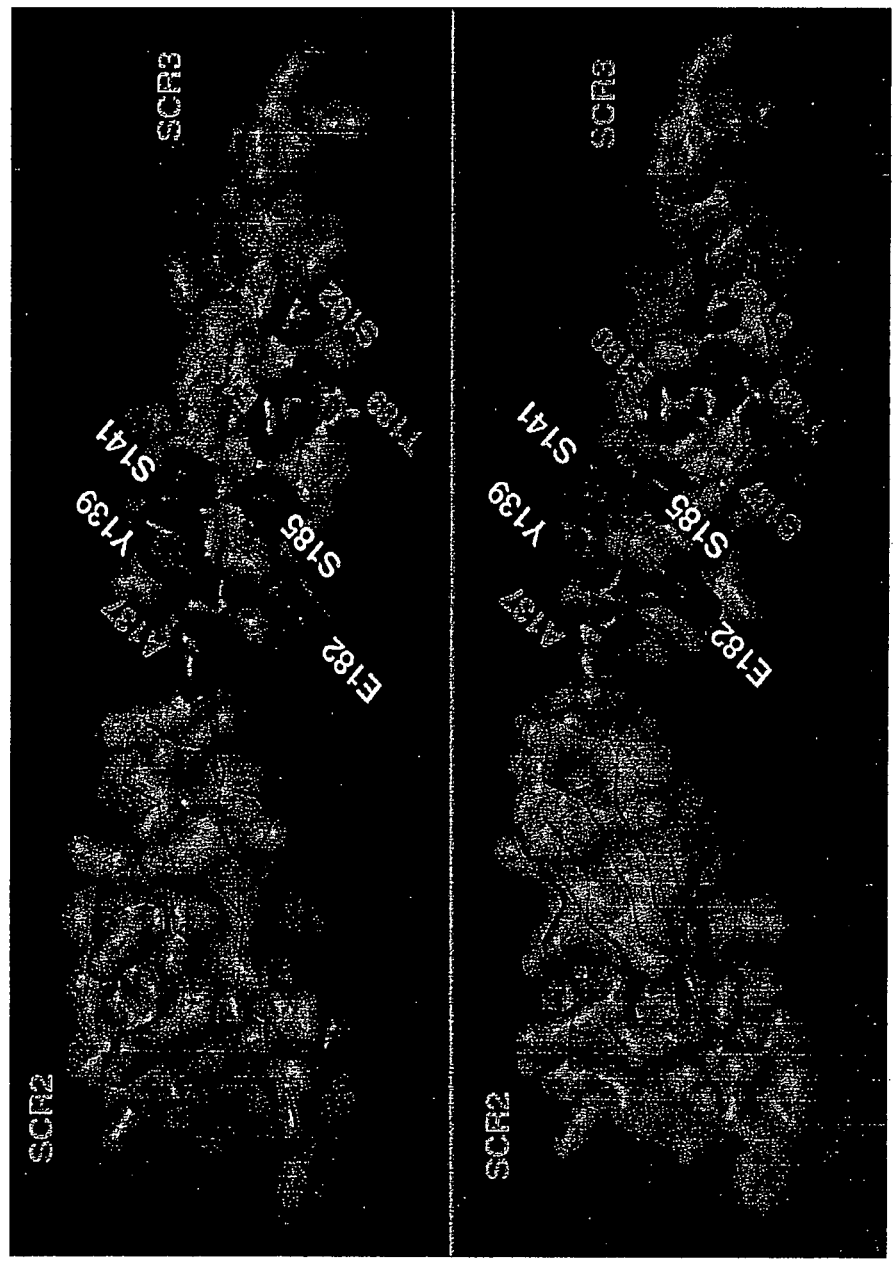
FIG. 11 is a schematic drawing showing a model of the epitope mapping for mAb1379 on the human factor B surface.
Figure 12:
FIG. 12 is a schematic drawing showing a modeled complex of mAB1379 (one Fab fragment) binding to factor B, with the antigen binding sides of the Fab having been modeled to cover the entire mapped epitope region.

In one embodiment, the epitope recognized by a factor B antibody of the invention can also be defined more particularly as being non-linear epitope located within the three-dimensional structure of a portion of the third SCR domain of factor B. The portion that contains the epitope is the three-dimensional structure of factor B that is defined by at substantially all of (e.g., at least about 90% of) amino acid positions Ala137-Ser192 of SEQ ID NO:2, or equivalent positions in a non-human factor B sequence, when such sequence is conformationally arranged as it occurs in the natural full-length factor B sequence. A model of the three-dimensional structure of factor B, which illustrates an epitope for mAb1379 is illustrated in FIG. 11 and FIG. 12, for example. As used herein, the "three dimensional structure" or "tertiary structure" of a protein refers to the arrangement of the components of the protein in three dimensions. Such term is well known to those of skill in the art. As used herein, the term "model" refers to a representation in a tangible medium of the three dimensional structure of a protein, polypeptide or peptide. For example, a model can be a representation of the three dimensional structure in an electronic file, on a computer screen, on a piece of paper (i.e., on a two dimensional medium), and/or as a ball-and-stick figure.

According to the present invention, an "epitope" of a given protein or peptide or other molecule is generally defined, with regard to antibodies, as a part of or site on a larger molecule to which an antibody or antigen-binding fragment thereof will bind, and against which an antibody will be produced. The term epitope can be used interchangeably with the term "antigenic determinant", "antibody binding site", or "conserved binding surface" of a given protein or antigen. More specifically, an epitope can be defined by both the amino acid residues involved in antibody binding and also by their conformation in three dimensional space (e.g., a conformational epitope or the conserved binding surface). An epitope can be included in peptides as small as about 4-6 amino acid residues, or can be included in larger segments of a protein, and need not be comprised of contiguous amino acid residues when referring to a three dimensional structure of an epitope, particularly with regard to an antibody-binding epitope. Antibody-binding epitopes are frequently conformational epitopes rather than a sequential epitope (i.e., linear epitope), or in other words, an epitope defined by amino acid residues arrayed in three dimensions on the surface of a protein or polypeptide to which an antibody binds. As mentioned above, the conformational epitope is not comprised of a contiguous sequence of amino acid residues, but instead, the residues are perhaps widely separated in the primary protein sequence, and are brought together to form a binding surface by the way the protein folds in its native conformation in three dimensions. The epitope recognized by the mAb1379 is a conformational epitope that is not a linear epitope.

One of skill in the art can identify and/or assemble conformational epitopes and/or sequential epitopes using known techniques, including mutational analysis (e.g., site-directed mutagenesis); protection from proteolytic degradation (protein footprinting); mimotope analysis using, e.g., synthetic peptides and pepscan, BIACORE or ELISA; antibody competition mapping; combinatorial peptide library screening; matrix-assisted laser desorption/ionization time-of-flight (MALDI-TOF) mass spectrometry; or three-dimensional modeling (e.g., using any suitable software program, including, but not limited to, MOLSCRIPT 2.0 (Avatar Software AB, Heleneborgsgatan 21C, SE-11731 Stockholm, Sweden), the graphical display program O (Jones et. al., *Acta Crystallography*, vol. A47, p. 110, 1991), the graphical display program GRASP, or the graphical display program INSIGHT). For example, one can use molecular replacement or other techniques and the known three-dimensional structure of a related protein to model the three-dimensional structure of factor B and predict the conformational epitope of antibody binding to this structure. Indeed, one can use one or any combination of such techniques to define the antibody binding epitope. FIGS. 11 and 12 illustrate the use of three-dimensional modeling, combined with information from mimotope analysis and mutational analysis, to identify the epitope of a factor B antibody of the present invention.

As used herein, the term "selectively binds to" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art, including, but not limited to: Western blot, immunoblot, enzyme-linked immunosorb ant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

One embodiment of the present invention includes an antibody or antigen binding fragment thereof that is a competitive inhibitor of the binding of factor B to the anti-factor B antibody (e.g., monoclonal antibody 1379). According to the present invention, a competitive inhibitor of factor B binding to an anti-factor B antibody of the present invention is an inhibitor (e.g., another antibody or antigen binding fragment or polypeptide) that binds to factor B at the same or similar epitope as the known anti-factor B antibody of the present invention (e.g., mAb 1379) such that binding of the known anti-factor B antibody to factor B is inhibited. A competitive inhibitor may bind to the target (e.g., factor B) with a greater affinity for the target than the anti-factor B antibody. A competitive inhibitor can be used in a manner similar to that described herein for the anti-factor B antibody 1379 (e.g., to inhibit the alternative complement pathway, to inhibit airway hyperresponsiveness in an animal, to inhibit airway inflammation in an animal, to inhibit reperfusion ischemia injury in an animal, etc.). For example, one embodiment of the invention relates to an isolated antibody or antigen binding fragment thereof that specifically binds to factor B, wherein the antibody or fragment thereof competitively inhibits mAb1379 for specific binding to factor B, and wherein, when the antibody or fragment thereof binds to factor B, the alternative complement pathway is inhibited or alternatively, the ability of mAb1379 to inhibit the alternative complement pathway is inhibited. Another embodiment relates to an isolated antibody or fragment thereof that specifically binds to factor B, wherein the isolated antibody or fragment thereof competitively inhibits a second antibody or fragment thereof for specific binding to factor B, and wherein the second antibody or fragment thereof binds to the third SCR domain of factor B.

Competition assays can be performed using standard techniques in the art (e.g., competitive ELISA or other binding assays). For example, competitive inhibitors can be detected and quantitated by their ability to inhibit the binding of factor B to a known, labeled anti-factor B antibody (e.g., the mAb 1379). Antibody-antibody competition assays in the presence of human factor B are described for example, in Example 3. Competitive inhibitors of the binding of factor B to anti-factor B 1379 are described in Example 3 and Table 4.

According to the present invention, antibodies are characterized in that they comprise immunoglobulin domains and as such, they are members of the immunoglobulin superfamily of proteins. Generally speaking, an antibody molecule comprises two types of chains. One type of chain is referred to as the heavy or H chain and the other is referred to as the light or L chain. The two chains are present in an equimolar ratio, with each antibody molecule typically having two H chains and two L chains. The two H chains are linked together by disulfide bonds and each H chain is linked to a L chain by a disulfide bond. There are only two types of L chains referred to as lambda ($\lambda$) and kappa ($\kappa$) chains. In contrast, there are five major H chain classes referred to as isotypes. The five classes include immunoglobulin M (IgM or $\mu$), immunoglobulin D (IgD or $\delta$), immunoglobulin G (IgG or $\lambda$), immunoglobulin A (IgA or $\alpha$), and immunoglobulin E (IgE or $\epsilon$). The distinctive characteristics between such isotypes are defined by the constant domain of the immunoglobulin and are discussed in detail below. Human immunoglobulin molecules comprise nine isotypes, IgM, IgD, IgE, four subclasses of IgG including IgG1 ($\gamma$1), IgG2 ($\gamma$2), IgG3 ($\gamma$3) and IgG4 ($\gamma$4), and two subclasses of IgA including IgA1 ($\alpha$1) and IgA2 ($\alpha$2). In humans, IgG subclass 3 and IgM are the most potent complement activators (classical complement system), while IgG subclass 1 and to an even lesser extent, 2, are moderate to low activators of the classical complement system. IgG4 subclass does not activate the complement system (classical or alternative). The only human immunoglobulin isotype known to activate the alternative complement system is IgA. In mice, the IgG subclasses are IgG1, IgG2a, IgG2b and IgG3. Murine IgG1 does not activate complement, while IgG2a, IgG2b and IgG3 are complement activators.

Each H or L chain of an immunoglobulin molecule comprises two regions referred to as L chain variable domains ($V_L$ domains) and L chain constant domains ($C_L$ domains), and H chain variable domains ($V_H$ domains) and H chain constant domains ($C_H$ domains). A complete $C_H$ domain comprises three sub-domains (CH1, CH2, CH3) and a hinge region. Together, one H chain and one L chain can form an arm of an immunoglobulin molecule having an immunoglobulin variable region. A complete immunoglobulin molecule comprises two associated (e.g., di-sulfide linked) arms. Thus, each arm of a whole immunoglobulin comprises a $V_{H+L}$ region, and a $C_{H+L}$ region. As used herein, the term "variable region" or "V region" refers to a $V_{H+L}$ region (also known as an Fv fragment), a $V_L$ region or a $V_H$ region. Also as used herein, the term "constant region" or "C region" refers to a $C_{H+L}$ region, a $C_L$ region or a $C_H$ region.

Limited digestion of an immunoglobulin with a protease may produce two fragments. An antigen binding fragment is referred to as an Fab, an Fab', or an F(ab')$_2$ fragment. A fragment lacking the ability to bind to antigen is referred to as an Fc fragment. An Fab fragment comprises one arm of an immunoglobulin molecule containing a L chain ($V_L$+$C_L$ domains) paired with the $V_H$ region and a portion of the $C_H$ region (CH1 domain). An Fab' fragment corresponds to an Fab fragment with part of the hinge region attached to the CH1 domain. An F(ab')$_2$ fragment corresponds to two Fab' fragments that are normally covalently linked to each other through a di-sulfide bond, typically in the hinge regions.

The $C_H$ domain defines the isotype of an immunoglobulin and confers different functional characteristics depending upon the isotype. For example, $\mu$ constant regions enable the formation of pentameric aggregates of IgM molecules and $\alpha$ constant regions enable the formation of dimers.

The antigen specificity of an immunoglobulin molecule is conferred by the amino acid sequence of a variable, or V, region. As such, V regions of different immunoglobulin molecules can vary significantly depending upon their antigen specificity. Certain portions of a V region are more conserved than others and are referred to as framework regions (FW regions). In contrast, certain portions of a V region are highly variable and are designated hypervariable regions. When the $V_L$ and $V_H$ domains pair in an immunoglobulin molecule, the hypervariable regions from each domain associate and create hypervariable loops that form the antigen binding sites. Thus, the hypervariable loops determine the specificity of an immunoglobulin and are termed complementarity-determining regions (CDRS) because their surfaces are complementary to antigens.

Further variability of V regions is conferred by combinatorial variability of gene segments that encode an immunoglobulin V region. Immunoglobulin genes comprise multiple germline gene segments which somatically rearrange to form a rearranged immunoglobulin gene that encodes an immunoglobulin molecule. $V_L$ regions are encoded by a L chain V gene segment and J gene segment (joining segment). $V_H$ regions are encoded by a H chain V gene segment, D gene segment (diversity segment) and J gene segment (joining segment).

Both a L chain and H chain V gene segment contain three regions of substantial amino acid sequence variability. Such regions are referred to as L chain CDR1, CDR2 and CDR3, and H chain CDR1, CDR2 and CDR3, respectively. The length of an L chain CDR1 can vary substantially between different $V_L$ regions. For example, the length of CDR1 can vary from about 7 amino acids to about 17 amino acids. In contrast, the lengths of L chain CDR2 and CDR3 typically do not vary between different $V_L$ regions. The length of a H chain CDR3 can vary substantially between different $V_H$ regions. For example, the length of CDR3 can vary from about 1 amino acid to about 20 amino acids. Each H and L chain CDR region is flanked by FW regions.

Other functional aspects of an immunoglobulin molecule include the valency of an immunoglobulin molecule, the affinity of an immunoglobulin molecule, and the avidity of an immunoglobulin molecule. As used herein, affinity refers to the strength with which an immunoglobulin molecule binds to an antigen at a single site on an immunoglobulin molecule (i.e., a monovalent Fab fragment binding to a monovalent antigen). Affinity differs from avidity which refers to the sum total of the strength with which an immunoglobulin binds to an antigen. Immunoglobulin binding affinity can be measured using techniques standard in the art, such as competitive binding techniques, equilibrium dialysis or BIAcore methods. As used herein, valency refers to the number of different antigen binding sites per immunoglobulin molecule (i.e., the number of antigen binding sites per antibody molecule of antigen binding fragment). For example, a monovalent immunoglobulin molecule can only bind to one antigen at one time, whereas a bivalent immunoglobulin molecule can bind to two or more antigens at one time, and so forth. Both monovalent and bivalent antibodies that selectively bind to proteins of the alternative complement pathway are encompassed herein.

In one embodiment, the antibody is a bi- or multi-specific antibody. A bi-specific (or multi-specific) antibody is capable of binding two (or more) antigens, as with a divalent (or multivalent) antibody, but in this case, the antigens are different antigens (i.e., the antibody exhibits dual or greater specificity). For example, an antibody that selectively binds to a protein in the alternative complement pathway according to the present invention (e.g., an anti-factor B antibody as described herein) can be constructed as a bi-specific antibody, wherein the second antigen binding specificity is for a desired target. Therefore, one bi-specific antibody encompassed by the present invention includes an antibody having: (a) a first portion (e.g., a first antigen binding portion) which binds to a protein in the alternative complement pathway (e.g., factor B); and (b) a second portion which binds to a cell surface molecule expressed by a cell. In this embodiment, the second portion can bind to any cell surface molecule. One preferred cell surface molecule is a receptor or ligand, so that the antibody is targeted to a particular cell or tissue type and/or to a particular site in an animal to which the antibody is delivered. In one embodiment, the second antigen binding specificity is for a complement receptor. A particularly preferred complement receptor includes, but is not limited to, complement receptor type 2 (CR2). Antibodies that selectively bind to CR2 and could therefore be used in this embodiment of the invention are described, for example, in U.S. Pat. No. 6,820,011.

In one embodiment, antibodies of the present invention include humanized antibodies. Humanized antibodies are molecules having an antigen binding site derived from an immunoglobulin from a non-human species, the remaining immunoglobulin-derived parts of the molecule being derived from a human immunoglobulin. The antigen binding site may comprise either complete variable regions fused onto human constant domains or only the complementarity determining regions (CDRs) grafted onto appropriate human framework regions in the variable domains. Humanized antibodies can be produced, for example, by modeling the antibody variable domains, and producing the antibodies using genetic engineering techniques, such as CDR grafting (described below). A description various techniques for the production of humanized antibodies is found, for example, in Morrison et al. (1984) *Proc. Natl. Acad. Sci. USA* 81:6851-55; Whittle et al. (1987) Prot. Eng. 1:499-505; Co et al. (1990) *J. Immunol.* 148:1149-1154; Co et al. (1992) *Proc. Natl. Acad. Sci. USA* 88:2869-2873; Carter et al. (1992) *Proc. Natl. Acad. Sci.* 89:4285-4289; Routledge et al. (1991) *Eur. J. Immunol.* 21:2717-2725 and PCT Patent Publication Nos. WO 91/09967; WO 91/09968 and WO 92/113831.

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)₂ fragments), as well as genetically-engineered antibodies or antigen binding fragments thereof, including single chain antibodies, humanized antibodies (discussed above), antibodies that can bind to more than one epitope (e.g., bi-specific antibodies), or antibodies that can bind to one or more different antigens (e.g., bi- or multi-specific antibodies), may also be employed in the invention.

Genetically engineered antibodies of the invention include those produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source as compared to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

In one embodiment, chimeric antibodies are produced according to the present invention comprising antibody variable domains that bind to a protein in the alternative complement pathway (e.g., factor B) and fused to these domains, a protein that serves as a second targeting moiety. For example, the targeting moiety can include a protein that is associated with the cell or tissue to be targeted or with a particular system in the animal. For example, the targeting moiety can be a portion of a complement receptor. One preferred complement receptor to use in this aspect of the invention includes complement receptor type 2 (CR2). The use of CR2 and portions thereof, such as a CR2 protein comprising short consensus repeat 1 (SCR1) and short consensus repeat 2 (SCR2) domains, in a fusion or chimeric protein (e.g., as a delivery system) is described in detail in U.S. Pat. No. 6,820,011.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

A preferred method to produce antibodies of the present invention includes (a) administering to an animal an effective amount of a protein or peptide (e.g., a factor B protein or peptide including domains thereof) to produce the antibodies and (b) recovering the antibodies. In another method, antibodies of the present invention are produced recombinantly. For example, once a cell line, for example a hybridoma, expressing an antibody according to the invention has been obtained, it is possible to clone therefrom the cDNA and to identify the variable region genes encoding the desired antibody, including the sequences encoding the CDRs. From here, antibodies and antigen binding fragments according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming/transfecting an appropriate host cell, in which production of the antibody will occur. Suitable expression hosts include bacteria, (for example, an *E. coli* strain), fungi, (in particular yeasts, e.g. members of the genera *Pichia, Saccharomyces*, or *Kluyveromyces*) and mammalian cell lines, e.g. a non-producing myeloma cell line, such as a mouse NSO line, or CHO cells. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al. (Molecular Cloning, Cold Spring Harbor Laboratory, New York, 1989); DNA sequencing can be performed as described in Sanger et al. (PNAS 74, 5463, (1977)) and the Amersham International plc sequencing handbook; and site directed mutagenesis can be carried out according to the method of Kramer et al. (*Nucl. Acids Res.* 12, 9441, (1984)) and the Anglian Biotechnology Ltd. handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews (ed. Tombs, M P, 10, Chapter 1, 1992, Intercept, Andover, UK) and in the aforementioned European Patent Applications.

Alternative methods, employing, for example, phage display technology (see for example U.S. Pat. Nos. 5,969,108, 5,565,332, 5,871,907, 5,858,657) or the selected lymphocyte antibody method of U.S. Pat. No. 5,627,052 may also be used for the production of antibodies and/or antigen fragments of the invention, as will be readily apparent to the skilled individual.

Another aspect of the present invention therefore generally relates to compositions and methods for selectively inhibiting the alternative complement pathway in an animal that has, or is at risk of developing, a condition or disease in which activation of the alternative complement pathway plays a role (e.g., the alternative complement pathway activation contributes to the condition or disease, exacerbates at least one symptom of the condition or disease, or causes the condition or disease). Such method includes the use of the novel factor B antibodies of the present invention, which have been described in detail above. Such conditions or diseases include, but are not limited to, conditions associated with airway hyperresponsiveness (including airway hyperresponsiveness that is associated with inflammation), ischemia-reperfusion injury, and fetal loss. Compositions and formulations comprising such antibodies and antigen binding fragments thereof, as well as antigen binding polypeptides that mimic the specificity of the factor B antibodies described herein, as well as discussion of methods of administration and doses, are described in detail below.

Method for Prevention or Inhibition of Airway Hyperresponsiveness and Airway Inflammation Based on the present inventors' discovery that the alternative complement pathway is necessary and sufficient to inhibit airway hyperresponsiveness and airway inflammation, another embodiment of the present invention relates to a method to inhibit airway hyperresponsiveness and/or airway inflammation in an animal that has or is at risk of developing, airway hyperresponsiveness associated with inflammation or airway inflammation. The method includes a step of selectively inhibiting the alternative complement pathway in an animal that has, or is at risk of developing, airway hyperresponsiveness, including airway hyperresponsiveness that is associated with inflammation (i.e., the airway hyperresponsiveness occurs as a result of inflammation or an inflammatory process, or occurs in conjunction with concurrent or prior inflammation in the airways).

The following discussion is provided to elaborate on the aspect of treating or preventing airway hyperresponsiveness and/or airway inflammation in an animal, or conditions or diseases related thereto. However, it is to be understood that the general discussion of inhibitors, routes of administration, doses, indicators of treatment, description of formulations, and the like, can apply to any of the embodiments of the invention described herein (i.e., to other conditions or diseases than those associated with airway hyperresponsiveness and airway inflammation). For example, many of the general aspects of the invention described below can be applied to the specific inhibition of the alternative complement pathway to treat other conditions, such as ischemia-reperfusion injury.

According to the present invention, to inhibit the alternative complement pathway in an animal refers to inhibiting the expression and/or the biological activity of at least one protein that is part of the alternative complement pathway. Such proteins include, but may not be limited to, factor B, factor D or properdin. To "selectively" inhibit the alternative complement pathway means that the method of the present invention preferentially or exclusively inhibits the alternative complement pathway, but does not inhibit or at least does not substantially inhibit other pathways for complement activation, including the classical complement pathway or the lectin pathway. For example, the novel factor B antibodies and antigen binding fragments thereof of the present invention are one example of a reagent that selectively inhibits the alternative complement pathway. This definition applies to other methods described herein wherein the alternative complement pathway is selectively inhibited.

Inhibition of the alternative complement pathway according to the present invention can be accomplished by directly affecting the expression (transcription or translation) or biological activity of a protein in the alternative complement pathway, or by directly affecting the ability of a protein to bind to a protein in the alternative complement pathway or to otherwise contribute to the activation of complement via the alternative pathway. More specifically, in one embodiment, expression of a protein refers to either the transcription of the protein or the translation of the protein. Therefore, the method of the present invention can inhibit the transcription and/or the translation of a protein in the animal that naturally expresses the protein (e.g., by administering an agent that inhibits the expression of the protein and genetically modifying an animal to have reduced protein expression). In another embodiment, inhibition of the alternative complement pathway is defined herein as any measurable (detectable) reduction (i.e., decrease, downregulation, inhibition) of the activity of the pathway, such as by any measurable reduction in the expression and/or biological activity of a protein within the alternative complement pathway.

According to the present invention, "airway hyperresponsiveness" or "AHR" refers to an abnormality of the airways that allows them to narrow too easily and/or too much in response to a stimulus capable of inducing airflow limitation. AHR can be a functional alteration of the respiratory system resulting from inflammation in the airways (i.e., AHR that is associated with inflammation) or resulting from airway remodeling (e.g., such as by collagen deposition). Airflow limitation refers to narrowing of airways that can be irreversible or reversible. Airflow limitation or airway hyperresponsiveness can be caused by collagen deposition, bronchospasm, airway smooth muscle hypertrophy, airway smooth muscle contraction, mucous secretion, cellular deposits, epithelial destruction, alteration to epithelial permeability, alterations to smooth muscle function or sensitivity, abnormalities of the lung parenchyma and infiltrative diseases in and around the airways. Many of these causative factors can be associated with inflammation, although AHR is a symptom that can be distinguished from inflammation (i.e., AHR is a specific condition or symptom as described above, that can be, but is not always, associated with prior or concurrent inflammation of the airways). AHR can be triggered in a patient with a condition associated with the above causative factors by exposure to a provoking agent or stimulus, also referred to herein as an AHR provoking stimulus. Such stimuli include, but are not limited to, an allergen, methacholine, a histamine, a leukotriene, saline, hyperventilation, exercise, sulfur dioxide, adenosine, propranolol, cold air, an antigen, bradykinin, acetylcholine, a prostaglandin, ozone, environmental air pollutants and mixtures thereof. The present invention is directed to airway hyperresponsiveness associated with any respiratory condition that involves inflammation, and particularly, to allergen-induced airway hyperresponsiveness.

Airway hyperresponsiveness is commonly associated with allergic inflammation and/or viral-induced inflammation. Airway hyperresponsiveness associated with allergic inflammation can occur in a patient that has, or is at risk of developing, a condition including, but not limited to, any chronic obstructive disease of the airways. Such conditions include, but are not limited to: asthma, chronic obstructive pulmonary disease, allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma and parasitic lung disease. Airway hyperresponsiveness associated with viral-induced inflammation can occur in a patient that has, or is at risk of developing, an infection by a virus including, but not limited to, respiratory syncytial virus (RSV), parainfluenza virus (PIV), rhinovirus (RV) and adenovirus. Other diseases or conditions to treat using the method and agents of the present invention include any pulmonary condition or pulmonary complication involving inflammation and/or airway hyperresponsiveness resulting from a disease, such as from a systemic autoimmune disease. For example, in systemic lupus erythematosus, pulmonary complications could be treated using the present invention.

Inflammation is typically characterized by the release of inflammatory mediators (e.g., cytokines or chemokines) which recruit cells involved in inflammation to a tissue. Airway inflammation is inflammation that occurs in the airways (lung tissue, respiratory cells and tissue) of an animal. A condition or disease associated with allergic inflammation is a condition or disease in which the elicitation of one type of immune response (e.g., a Th2-type immune response) against a sensitizing agent, such as an allergen, can result in the release of inflammatory mediators that recruit cells involved in inflammation in an animal, the presence of which can lead to tissue damage and sometimes death. As discussed above, AHR is frequently associated with (occurs in conjunction with or perhaps as a result of) airway inflammation. It is noted that the symptom or condition of AHR can sometimes be treated independently of the symptom of inflammation and vice versa (e.g., a treatment for AHR may or may not have an impact on inflammation—these are separable conditions).

AHR can be measured by a stress test that comprises measuring an animal's respiratory system function in response to a provoking agent (i.e., stimulus). AHR can be measured as a change in respiratory function from baseline plotted against the dose of a provoking agent (a procedure for such measurement and a mammal model useful therefore are described in detail below in the Examples). Respiratory function (and therefore the biological characteristics of AHR) can be measured by, for example, spirometry, plethysmograph, peak flows, symptom scores, physical signs (i.e., respiratory rate), wheezing, exercise tolerance, use of rescue medication (i.e., bronchodilators), cough and blood gases. In humans, spirometry can be used to gauge the change in respiratory function in conjunction with a provoking agent, such as methacholine or histamine. In humans, spirometry is performed by asking a person to take a deep breath and blow, as long, as hard and as fast as possible into a gauge that measures airflow and volume. The volume of air expired in the first second is known as forced expiratory volume ($FEV_1$) and the total amount of air expired is known as the forced vital capacity (FVC). In humans, normal predicted $FEV_1$ and FVC are available and standardized according to weight, height, sex and race. An individual free of disease has an $FEV_1$ and a FVC of at least about 80% of normal predicted values for a particular person and a ratio of $FEV_1/FVC$ of at least about 80%. Values are determined before (i.e., representing a patient's resting state) and after (i.e., representing a patient's higher lung resistance state) inhalation of the provoking agent. The position of the resulting curve indicates the sensitivity of the airways to the provoking agent.

The effect of increasing doses or concentrations of the provoking agent on lung function is determined by measuring the forced expired volume in 1 second ($FEV_1$) and $FEV_1$ over forced vital capacity ($FEV_1/FVC$ ratio) of the animal challenged with the provoking agent. In humans, the dose or concentration of a provoking agent (i.e., methacholine or histamine) that causes a 20% fall in $FEV_1$ ($PC_{20}FEV_1$) is indicative of the degree of AHR. $FEV_1$ and FVC values can be measured using methods known to those of skill in the art.

Pulmonary function measurements of airway resistance ($R_L$) and dynamic compliance ($C_L$) and hyperresponsiveness can be determined by measuring transpulmonary pressure as the pressure difference between the airway opening and the body plethysmograph. Volume is the calibrated pressure change in the body plethysmograph and flow is the digital differentiation of the volume signal. Resistance ($R_L$) and compliance ($C_L$) are obtained using methods known to those of skill in the art (e.g., such as by using a recursive least squares solution of the equation of motion). It should be noted that measuring the airway resistance ($R_L$) value in a non-human mammal (e.g., a mouse) can be used to diagnose airflow obstruction similar to measuring the $FEV_1$ and/or $FEV_1/FVC$ ratio in a human.

A variety of provoking agents are useful for measuring AHR values. Suitable provoking agents include direct and indirect stimuli, and are typically provoking agents that trigger AHR in vivo. As used herein, the phrase "provoking agent" can be used interchangeably with the phrase "AHR provoking stimulus". Preferred provoking agents or stimulus include, for example, an allergen, methacholine, a histamine, organic irritants, irritating gases and chemicals, a leukotriene, saline, hyperventilation, exercise, sulfur dioxide, adenosine, propranolol, cold air, an antigen, bradykinin, acetylcholine, a prostaglandin, ozone, environmental air pollutants and mixtures thereof. Preferably, for experimental induction of AHR, methacholine (Mch) is used as a provoking agent. Preferred concentrations of Mch to use in a concentration-response curve are between about 0.001 and about 100 milligram per milliliter (mg/ml). More preferred concentrations of Mch to use in a concentration-response curve are between about 0.01 and about 50 mg/ml. Even more preferred concentrations of Mch to use in a concentration-response curve are between about 0.02 and about 25 mg/ml. When Mch is used as a provoking agent, the degree of AHR is defined by the provocative concentration of Mch needed to cause a 20% drop of the $FEV_1$ of an animal ($PC_{20methacholine}FEV_1$). For example, in humans and using standard protocols in the art, a normal person typically has a $PC_{20methacholine}FEV_1 > 8$ mg/ml of Mch. Thus, in humans, AHR is defined as $PC_{20methacholine}FEV_1 < 8$ mg/ml of Mch.

According to the present invention, respiratory function can also be evaluated with a variety of static tests that comprise measuring an animal's respiratory system function in the absence of a provoking agent. Examples of static tests include, for example, spirometry, plethysmography, peak flows, symptom scores, physical signs (i.e., respiratory rate), wheezing, exercise tolerance, use of rescue medication (i.e., bronchodilators), blood gases and cough. Evaluating pulmonary function in static tests can be performed by measuring, for example, Total Lung Capacity (TLC), Thoracic Gas Volume (TgV), Functional Residual Capacity (FRC), Residual Volume (RV) and Specific Conductance (SGL) for lung volumes, Diffusing Capacity of the Lung for Carbon Monoxide (DLCO), arterial blood gases, including pH, $P_{O2}$ and $P_{CO2}$ for gas exchange. Both $FEV_1$ and $FEV_1/FVC$ can be used to measure airflow limitation. If spirometry is used in humans, the $FEV_1$ of an individual can be compared to the $FEV_1$ of predicted values. Predicted $FEV_1$ values are available for standard normograms based on the animal's age, sex, weight, height and race. A normal animal typically has an $FEV_1$ at least about 80% of the predicted $FEV_1$ for the animal. Airflow limitation results in a $FEV_1$ or FVC of less than 80% of predicted values. An alternative method to measure airflow limitation is based on the ratio of $FEV_1$ and FVC ($FEV_1/FVC$). Disease free individuals are defined as having a $FEV_1/FVC$ ratio of at least about 80%. Airflow obstruction causes the ratio of $FEV_1/FVC$ to fall to less than 80% of predicted values. Thus, an animal having airflow limitation is defined by an $FEV_1/FVC$ less than about 80%.

As used herein, to reduce airway hyperresponsiveness refers to any measurable reduction in airway hyperresponsiveness and/or any reduction of the occurrence or frequency with which airway hyperresponsiveness occurs in a patient. A reduction in AHR can be measured using any of the above-described techniques or any other suitable method known in the art. Preferably, airway hyperresponsiveness, or the potential therefor, is reduced, optimally, to an extent that the animal no longer suffers discomfort and/or altered function resulting from or associated with airway hyperresponsiveness. To prevent airway hyperresponsiveness refers to preventing or stopping the induction of airway hyperresponsiveness before biological characteristics of airway hyperresponsiveness as discussed herein can be substantially detected or measured in a patient. Once one or more of the biological characteristics of airway hyperresponsiveness can be substantially detected or measured, acute onset airway hyperresponsiveness is deemed to have occurred.

In one embodiment, the method of the present invention decreases methacholine responsiveness in the animal. Preferably, the method of the present invention results in an improvement in an animal's $PC_{20methacholine}FEV_1$ value such that the $PC_{20methacholine}FEV_1$ value obtained before use of the present method when the animal is provoked with a first concentration of methacholine is the same as the $PC_{20methacholine}FEV_1$ value obtained after use of the present method when the animal is provoked with double the amount of the first concentration of methacholine. Preferably, the method of the present invention results in an improvement in an animal's $PC_{20methacholine}FEV_1$ value such that the $PC_{20methacholine}FEV_1$ value obtained before the use of the present method when the animal is provoked with between about 0.01 mg/ml to about 8 mg/ml of methacholine is the same as the $PC_{20methacholine}FEV_1$ value obtained after the use of the present method when the animal is provoked with between about 0.02 mg/ml to about 16 mg/ml of methacholine.

In another embodiment, the method of the present invention improves an animal's $FEV_1$ by at least about 5%, and more preferably by between about 6% and about 100%, more preferably by between about 7% and about 100%, and even more preferably by between about 8% and about 100% of the animal's predicted $FEV_1$. In another embodiment, the method of the present invention improves an animal's $FEV_1$ by at least about 5%, and preferably, at least about 10%, and even more preferably, at least about 25%, and even more preferably, at least about 50%, and even more preferably, at least about 75%.

In yet another embodiment, the method of the present invention results in an increase in the $PC_{20methacholine}FEV_1$ of an animal by about one doubling concentration towards the $PC_{20methacholine}FEV_1$ of a normal animal. A normal animal refers to an animal known not to suffer from or be susceptible to abnormal AHR. A patient, or test animal refers to an animal suspected of suffering from or being susceptible to abnormal AHR.

Therefore, an animal that has airway hyperresponsiveness is an animal in which airway hyperresponsiveness can be measured or detected, such as by using one of the above methods for measuring airway hyperresponsiveness, wherein the airway hyperresponsiveness is typically induced by exposure to an AHR provoking stimulus, as described above. Similarly, an animal that has allergen-induced airway hyperresponsiveness is an animal in which airway hyperresponsiveness can be measured or detected, such as by using one of the above methods for measuring airway hyperresponsiveness, wherein the airway hyperresponsiveness is induced by exposure to an allergen. To be induced by an AHR provoking stimulus, such as an allergen, the airway hyperresponsiveness is apparently or obviously, directly or indirectly triggered by (e.g., caused by, a symptom of, indicative of, concurrent with) an exposure to the stimulus. Symptoms, or biological characteristics, of AHR include, but are not limited to, indicators of altered respiratory function (described in detail above), change in respiratory rate, wheezing, lowered exercise tolerance, cough and altered blood gases. Detection or measurement of any one or more of such symptoms is indicative of the onset of acute AHR.

In the case of an allergen, the airway hyperresponsiveness is apparently or obviously, directly or indirectly triggered by an allergen to which an animal has previously been sensitized. Sensitization to an allergen refers to being previously exposed one or more times to an allergen such that an immune response is developed against the allergen. Responses associated with an allergic reaction (e.g., histamine release, rhinitis, edema, vasodilation, bronchial constriction or airway hyperresponsiveness, airway inflammation), typically do not occur when a naive individual is exposed to the allergen for the first time, but once a cellular and humoral immune response is produced against the allergen, the individual is "sensitized" to the allergen. Allergic reactions then occur when the sensitized individual is re-exposed to the same allergen (e.g., an allergen challenge). Once an individual is sensitized to an allergen, the allergic reactions can become worse with each subsequent exposure to the allergen, because each re-exposure not only produces allergic symptoms, but further increases the level of antibody produced against the allergen and the level of T cell response against the allergen.

Typically, conditions associated with allergic responses to antigens (i.e., allergens) are at least partially characterized by inflammation of pulmonary tissues. Such conditions or diseases are discussed above. It is noted that this embodiment of the present invention is specifically directed to the treatment of AHR, and as such, it is not required that the related condition or causative factor that caused the AHR, such as allergic inflammation, be significantly reduced or "cured", although the effects of the present method likely extend to inhibition of allergic inflammation. The method of the present invention is fully effective to reduce AHR even after the inflammatory response in the lungs of the animal is fully established. An animal that is at risk of developing airway hyperresponsiveness is an animal that has been exposed to, or is at risk of being exposed to, an AHR provoking stimulus that is sufficient to trigger AHR, but does not yet display a measurable or detectable characteristic or symptom of airway hyperresponsiveness, such symptoms being described previously herein. An animal that is at risk of developing allergen-induced airway hyperresponsiveness is an animal that has been previously sensitized to an allergen, and that has been exposed to, or is at risk of being exposed to, an amount of the allergen that is sufficient to trigger AHR (i.e., a triggering, or challenge dose of allergen), but does not yet display a measurable or detectable characteristic or symptom of airway hyperresponsiveness. An animal that is at risk of developing airway hyperresponsiveness also includes an animal that is identified as being predisposed to or susceptible to such a condition or disease.

The method of the present invention can also inhibit or reduce airway inflammation in an animal. Inflammation, and particularly eosinophilic inflammation, is a hallmark of many respiratory diseases, including asthma. Airway inflammation can be evaluated using several parameters including, but not limited to, accumulation of inflammatory cells (e.g., eosinophils, macrophages, neutrophils, lymphocytes) in the lungs, altered levels of various cytokines (e.g., IL-4, IL-5, IL-10, IL-12, IL-13 and IFN-γ) in the bronchoalveolar lavage fluid (BALF), and/or a change in mucus production in the lungs. Measurement of many of these parameters are exemplified in the Examples.

Agents and formulations of the present invention can be administered to any animal patient, and preferably to humans. According to the present invention, administration of an agent or formulation is useful to inhibit AHR, airway inflammation, or to treat a disease associated with such conditions. Patients whom are suitable candidates for the method of the present invention include, but are not limited to, patients that have, or are at risk of developing (e.g., are predisposed to), such a condition or disease. As discussed above, the present invention is primarily directed to the treatment of AHR and/or airway inflammation, and as such, it is not required that the condition or causative factor that caused the AHR or airway inflammation, or the disease associated with these conditions, be significantly reduced or "cured", although the effects of the present method likely extend to a significant therapeutic benefit for the patient. This concept also generally applies to other conditions and diseases in which the alternative complement pathway plays a role.

As such, a therapeutic benefit is not necessarily a cure for a particular disease or condition (including any disease or condition described herein), but rather, preferably encompasses a result which most typically includes alleviation of the disease or condition, elimination of the disease or condition, reduction of a symptom associated with the disease or condition, prevention or alleviation of a secondary disease or condition resulting from the occurrence of a primary disease or condition, and/or prevention of the disease or condition. As used herein, the phrase "protected from a disease" refers to reducing the symptoms of the disease; reducing the occurrence of the disease, and/or reducing the severity of the disease. Protecting a patient can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment). A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

Accordingly, the method of the present invention includes the use of a variety of agents (i.e., regulatory compounds) which, by acting directly on a protein in the alternative complement pathway, selectively inhibit the expression and/or biological activity of one or more proteins in the alternative complement pathway such that airway hyperresponsiveness and/or airway inflammation is reduced in an animal. Agents useful in the present invention include, for example, proteins, nucleic acid molecules, antibodies, and compounds that are products of rational drug design (i.e., drugs). Such agents are generally referred to herein as inhibitors. According to the present invention, an inhibitor is any agent which inhibits, either by direct inhibition or competitive inhibition, the expression and/or biological activity of a protein (e.g., a protein in the alternative complement pathway), and includes agents which act on factor B, factor D or properdin. In one embodiment of the present invention, inhibition of the alternative complement pathway or a protein of the alternative complement pathway is defined herein as any measurable (detectable) reduction (i.e., decrease, downregulation, inhibition) of the biological activity of a protein in the alternative complement pathway. The biological activity or biological action of a protein refers to any function(s) exhibited or performed by a naturally occurring form of the protein as measured or observed in vivo (i.e., in the natural physiological environment of the protein) or in vitro (i.e., under laboratory conditions). For example, a biological activity of factor B can include, but is not limited to, binding to activated C3, solubilization of immune complexes, B cell growth factor activity, and monocyte activation. According to the present invention, the biological activity of a protein can be inhibited by directly preventing or inhibiting (reducing, decreasing) the ability of the protein to bind to and/or activate another protein (e.g., C3), thereby inhibiting downstream events resulting from such binding. Preferably, the biological activity of the alternative complement pathway is inhibited by administering an agent that inhibits at least one protein in the pathway, such agent including, but not limited to, an agent that binds to a protein in the pathway or competes with the protein in the pathway in a manner that the ability of the protein to bind to and/or activate another protein is inhibited or prevented. Such an agent includes, but is not limited to antagonists of the protein, antibodies (including antigen-binding fragments thereof), other antigen binding polypeptides, and small molecules (e.g. synthetic compounds or drugs).

One agent useful in the present invention is an antagonist of the alternative complement pathway, including an antagonist of a protein within this pathway. According to the present invention, an "antagonist" refers to any compound which inhibits (e.g., antagonizes, reduces, decreases, blocks, reverses, or alters) the effect of a given protein. More particularly, an antagonist is capable of acting in a manner relative to the given protein's activity, such that the biological activity of the given protein, is decreased or blocked in a manner that is antagonistic (e.g., against, a reversal of, contrary to) to the natural action of the given protein. Antagonists can include, but are not limited to, an antibody or antigen binding fragment thereof, a protein, peptide, nucleic acid (including ribozymes and antisense), or a product of drug/compound/peptide design or selection that provides the antagonistic effect. For example, the present invention includes any antagonists of the natural proteins, factor B, factor D or properdin, including antibody antagonists, protein/peptide antagonists, nucleic acid antagonists, or small molecule antagonists (e.g., a small molecule inhibitor).

In a preferred embodiment of the present invention, the agent used for inhibiting a protein of the alternative complement pathway is an antibody or an antigen binding fragment thereof. Similarly, an antigen binding polypeptide is also particularly preferred for use in the present invention. In one aspect, the antibody selectively binds to the protein of the alternative complement pathway in a manner such that the protein is inhibited or prevented from binding to another protein with which it normally (under natural or physiological conditions) interacts. In another aspect, the antibody selectively binds to the protein in a manner such that the protein is inhibited or prevented from activating another protein with which it normally interacts, even though the protein may at least partially bind to the other protein. Particularly preferred antibodies and antigen binding fragments thereof for use in selective inhibition of the alternative complement pathway have been described in detail above (e.g., the factor B antibodies described herein, and particularly, the mAb1379 antibody described in detail herein).

Preferably, an antibody or antigen binding fragment thereof useful in the present invention binds to a protein selected from factor B, factor D or properdin. Most preferably, the invention includes an antibody or antigen binding fragment thereof that binds to factor B. Antibodies (and antigen binding fragments thereof) that selectively bind to factor B and inhibit the alternative complement pathway according to the invention are described and exemplified in detail herein. In one embodiment, the antibody or antigen binding fragment thereof binds to a conserved binding surface or epitope of such a protein that is conserved among animal species, and particularly mammalian, species (i.e., the antibody is cross-reactive with the protein from two or more different mammalian species). In particular, the present invention includes an antibody that binds to a protein in the alternative complement pathway from at least two, and preferably, several different mammalian species, including, but not limited to, human, non-human primate, mouse, rat, pig, horse and rabbit.

The invention also extends to non-antibody polypeptides, sometimes referred to as antigen binding partners or antigen binding polypeptides, that have been designed to bind selectively to and cause the neutralization or inhibition of a protein according to the present invention. Examples of the design of such polypeptides, which possess a prescribed ligand specificity are given in Beste et al. (*Proc. Natl. Acad. Sci.* 96:1898-1903, 1999), incorporated herein by reference in its entirety.

The present invention includes, in addition to antibodies, antigen-binding fragments thereof, and antigen binding polypeptides, other agents that inhibit a protein in the alternative complement pathway. Such agents include, for example, compounds that are products of rational drug design, natural products, and compounds having partially defined regulatory properties. A regulatory agent, including an antagonist of a given protein, can be a protein-based compound, a carbohydrate-based compound, a lipid-based compound, a nucleic acid-based compound, a natural organic compound, a synthetically derived organic compound, an antibody, or fragments thereof. In one embodiment, such regulatory agents of the present invention include drugs, including peptides, oligonucleotides, carbohydrates and/or synthetic organic molecules which regulate the production and/or function of one or more proteins in the alternative complement pathway. Such an agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, *Molecular Biotechnology Therapeutic Applications and Strategies*, Wiley-Liss, Inc., which is incorporated herein by reference in its entirety.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., supra.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Various other methods of structure-based drug design are disclosed in Maulik et al., 1997, supra. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

An isolated nucleic acid molecule that is useful as an agent for inhibiting a protein in the alternative complement pathway is an anti-sense nucleic acid molecule, a ribozyme or siRNA. As used herein, an anti-sense nucleic acid molecule is defined as an isolated nucleic acid molecule that reduces expression of a protein by hybridizing under high stringency conditions to a gene encoding the protein. Such a nucleic acid molecule is sufficiently similar to the gene encoding the protein that the molecule is capable of hybridizing under high stringency conditions to the coding or complementary strand of the gene or RNA encoding the natural protein. RNA interference (RNAi) is a process whereby double stranded RNA, and in mammalian systems, short interfering RNA (siRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA. A ribozyme is an RNA segment that functions by binding to the target RNA moiety and inactivate it by cleaving the phosphodiester backbone at a specific cutting site.

A gene includes regulatory regions that control production of the protein encoded by that gene (such as, but not limited to, transcription, translation or post-translation control regions) as well as the coding region itself. The genes encoding various proteins of the alternative complement pathway, including factor B, factor D or properdin, have been identified and are known in the art. An isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated nucleic acid molecule of the present invention can be isolated from its natural source or produced using recombinant DNA technology (e.g., polymerase chain reaction (PCR) amplification, cloning) or chemical synthesis.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

Ischemia-Reperfusion Injury

Yet another embodiment of the present invention relates to the inventors' discovery that the inhibition of factor B, for example, using the anti-factor B antibodies or antigen binding fragments thereof described herein, also inhibits ischemia-reperfusion injury. This was demonstrated in a model for renal ischemia-reperfusion injury. Therefore, the methods and compositions of the present invention also have therapeutic utility in a conditions related to ischemia-reperfusion injury, and in one aspect of the invention, renal ischemia-reperfusion injury. Other types of ischemia-reperfusion injury that can be prevented or reduced using this method include, but are not limited to, cardiac ischemia-reperfusion injury, central nervous system ischemia-reperfusion injury, ischemia-reperfusion injury of the limbs or digits, ischemia-reperfusion of internal organs such as the lung, liver or intestine, or ischemia-reperfusion injury of any transplanted organ or tissue.

This method of the invention includes a step of selectively inhibiting the alternative complement pathway in an animal that has, or is at risk of experiencing or developing, ischemia-reperfusion. Preferably, at least one symptom or type of injury due to ischemia-reperfusion is prevented or inhibited. Ischemia-reperfusion injury can cause increases in the production of or oxidation of various potentially harmful compounds produced by cells and tissues, which can lead to oxidative damage to or death of cells and tissues. For example, renal ischemia-reperfusion injury can result in histological damage to the kidneys, including kidney tubular damage and changes characteristic of acute tubular necrosis. The resultant renal dysfunction permits the accumulation of nitrogenous wastes ordinarily excreted by the kidney, such as serum urea nitrogen (SUN). Ischemia-reperfusion may also cause injury to remote organs, such as the lung. The method preferably utilizes the novel factor B antibodies of the present invention as described in detail above which, when administered to an animal that has, or is at risk of experiencing or developing, ischemia-reperfusion, prevents, reduces or inhibits at least one symptom of injury due to ischemia-reperfusion. Any of the factor B antibodies of the present invention as described herein, or antigen binding fragments thereof, or antigen binding polypeptides having a similar binding specificity, are useful in this embodiment of the invention. A description of preferred doses, routes of administration, and compositions and formulations comprising such antibodies and related reagents in various methods of the invention is provided herein and is encompassed by this embodiment.

It is noted that this embodiment of the present invention is specifically directed to the treatment of ischemia-reperfusion injury, and as such, it is not required that the related condition or causative factor that caused the ischemia-reperfusion injury be significantly reduced or "cured". The method of the present invention is fully effective to prevent or reduce damage or injury associated with ischemia-reperfusion or to improve or reduce at least one symptom of such injury. Therefore, administration of an agent or formulation described herein is useful for the prevention or inhibition of ischemia-reperfusion injury, although it is not required that all such injury be completely prevented, but it is preferred that the patient experience at least one therapeutic benefit from the use of the agent or formulation.

Formulations, Compositions, and Methods Related to the Embodiments of the Invention Another embodiment of the present invention also includes a formulation or composition comprising an inhibitor of the alternative complement pathway and particularly, a selective inhibitor of the alternative complement pathway as described herein. The formulations or compositions can be used in any of the methods described herein and with any of the reagents described herein (e.g., the novel factor B antibodies described herein). In one embodiment, the composition is useful for reducing or preventing airway hyperresponsiveness in an animal. In another embodiment, the composition is useful for reducing or preventing ischemia-reperfusion injury in an animal. In yet another embodiment, the composition is useful for treating or preventing a condition or disease by selective inhibition of the alternative complement pathway. The formulation comprises: (a) an inhibitor of the alternative complement pathway as described herein; and (b) a pharmaceutically acceptable carrier.

In one embodiment, the formulation or composition can include one or more additional agents, such as an anti-inflammatory agent suitable for reducing inflammation in an animal that has, or is at risk of developing, airway hyperresponsiveness, and particularly, airway hyperresponsiveness that is associated with inflammation. The anti-inflammatory agent can be any anti-inflammatory agent which is suitable for use in reducing inflammation in a patient that has an inflammatory condition associated with airway hyperresponsiveness, including, but not limited to: corticosteroids, (oral, inhaled and injected), β-agonists (long or short acting), leukotriene modifiers (inhibitors or receptor antagonists), cytokine or cytokine receptor antagonists, anti-IgE, phosphodiesterase inhibitors, sodium cromoglycate, nedocrimal, theophylline, and inhibitors of T cell function. Particularly preferred anti-inflammatory agents for use in the present formulation include, corticosteroids, leukotriene modifiers, and cytokine or cytokine receptor antagonists.

In another embodiment, the formulation or composition can include one or more additional agents, such as an additional agent suitable for preventing or reducing ischemia-reperfusion injury in an animal. Such agents include, but are not limited to, anti-inflammatory agents; or inhibitors of oxidation and free radical damage.

In another embodiment, the formulation or composition can include one or more additional agents, such as an additional agent suitable for treatment of another disease or condition associated with activation of the alternative complement pathway.

According to the present invention, a "pharmaceutically acceptable carrier" includes pharmaceutically acceptable excipients and/or pharmaceutically acceptable delivery vehicles, which are suitable for use in the administration of a formulation or composition to a suitable in vivo site. A suitable in vivo site is preferably any site wherein the alternative complement pathway can be inhibited. In one preferred embodiment, when the patient has or is at risk of developing airway hyperresponsiveness and/or airway inflammation, a suitable in vivo site is preferably in the lung tissue or airways. Other preferred in vivo sites include other tissues or organs where conditions associated with the alternative complement pathway may be centered. In another preferred embodiment, a suitable in vivo site is any site where ischemia-reperfusion injury occurs, such as in the heart or pulmonary system, central nervous system, limbs or digits, internal organs (e.g., lung, liver or intestine), or in any transplanted organ or tissue. Preferred pharmaceutically acceptable carriers are capable of maintaining an agent used in a formulation of the invention in a form that, upon arrival of the agent at the target site in a patient, the agent is capable of acting on its target (e.g., a protein that is a component of the alternative complement pathway), preferably resulting in a therapeutic benefit to the patient.

Suitable excipients of the present invention include excipients or formularies that transport or help transport, but do not specifically target a composition to a cell or tissue (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Formulations of the present invention can be sterilized by conventional methods and/or lyophilized.

One type of pharmaceutically acceptable carrier includes a controlled release formulation that is capable of slowly releasing a composition of the present invention into an animal. As used herein, a controlled release formulation comprises an agent of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other suitable carriers include any carrier that can be bound to or incorporated with the agent that extends that half-life of the agent to be delivered. Such a carrier can include any suitable protein carrier or even a fusion segment that extends the half-life of a protein when delivered in vivo. Suitable delivery vehicles have been previously described herein, and include, but are not limited to liposomes, viral vectors or other delivery vehicles, including ribozymes. Natural lipid-containing delivery vehicles include cells and cellular membranes. Artificial lipid-containing delivery vehicles include liposomes and micelles. As discussed above, a delivery vehicle of the present invention can be modified to target to a particular site in a patient, thereby targeting and making use of an inhibitory agent at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

In one embodiment, an agent useful in the present methods is administered in a formulation suitable for pulmonary or nasal delivery, and particularly, aerosol delivery, also referred to herein as an aerosolized formulation. Such a route of delivery is particularly useful in the method to prevent or inhibit AHR and/or airway inflammation in a patient, but can be used in other conditions when delivery to the lung or airways is desired. In addition, these formulations are particularly useful for the delivery of antibodies. Such a formulation generally includes a carrier, and preferably, a pharmaceutically acceptable carrier. Carriers that are particularly useful for aerosol delivery according to the present invention include, but are not limited to: anhydrous ethanol; dry, dispersible powders; small capsules (e.g., microcapsules or microparticles); liposomes; injectable excipients; and nebulized sprays. Anhydrous ethanol for the delivery of proteins and peptides is described, for example, in Choi et al., 2001, *PNAS USA* 98(20):11103-11107. Dry, dispersible powders suitable for aerosolized delivery of agents are described in detail, for example, in U.S. Pat. No. 6,165,463, incorporated herein by reference in its entirety (See also products from Inhale Therapeutic Systems, Inc., now Nektar, and Quadrant Technology). Suitable liposomes for use in aerosols include any liposome, and particularly, any liposome that is sufficiently small to be delivered by aerosol in the method of the invention. Microcapsules and microparticles are known in the art. For example, Alliance Pharmaceutical Corporation has a particle engineering technology, called PulmoSphere®, prepared by a proprietary spray-drying process and are designed to be both hollow and porous. A product by Ventolin® consists of micronized albuterol (free base) particles suspended in a mixture of CFC-based propellants. Proventil HFA® contains micronized albuterol sulfate and a small percentage of an ethanol co-solvent to solubilize the stabilizing oleic acid surfactant. Incorporation of drugs into liposomes has several advantages for aerosol delivery. Because liposomes are relatively insoluble, the retention time of some drugs in the lung can be prolonged for increased efficacy. Liposomes are also taken up primarily by phagocytic cells which make them particularly suitable for delivery of certain drugs. Nebulized formulations are described in the Examples. Devices for delivery of aerosolized formulations include, but are not limited to, pressurized metered dose inhalers (MDI), dry powder inhalers (DPI), metered solution devices (MSI), and ultrasonic inhalers, and include devices that are nebulizers and inhalers. Various agents can be used in formulations delivered by such devices as suspension aids and solubilizers that are particularly useful for the delivery of proteins (e.g., oligolactic acid, acyl-amide acids, and mono-functionalized M-PEGS; see, McKenzie and Oliver; 2000; Formulating Therapeutic Proteins and Peptides in Pressurized Metered Dose Inhalers For Pulmonary Delivery; 3M Health Care Ltd., Morley Street, Loughborough, Leicesteshire LE11 1EP, UK).

A pharmaceutically acceptable carrier which is capable of targeting is herein referred to as a "targeting delivery vehicle." Targeting delivery vehicles of the present invention are capable of delivering a formulation, including an inhibitory agent, to a target site in a patient. A "target site" refers to a site in a patient to which one desires to deliver a therapeutic formulation. For example, a target site can be any cell or tissue which is targeted by an antibody of the present invention, or by direct injection or delivery using liposomes, viral vectors or other delivery vehicles, including ribozymes. A delivery vehicle or antibody of the present invention can be modified to target to a particular site in an animal, thereby targeting and making use of particular compound, antibody, protein, or nucleic acid molecule at that site. Suitable modifications include manipulating the chemical formula of the lipid portion of a delivery vehicle and/or introducing into the vehicle a compound capable of specifically targeting a delivery vehicle to a preferred site, for example, a preferred cell or tissue type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Particularly useful examples include any ligands that are associated with the complement pathway (e.g., CR2, C3, C3d, C3dg, iC3b, C3b) or any ligands that are associated with the cell type, tissue type, or site in the animal to be treated. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One delivery vehicle useful for a variety of administration routes and agents is a liposome. A liposome is capable of remaining stable in an animal for a sufficient amount of time to deliver a nucleic acid molecule, or even a protein or antibody, described in the present invention to a preferred site in the animal. A liposome, according to the present invention, comprises a lipid composition that is capable of delivering a nucleic acid molecule described in the present invention to a particular, or selected, site in an animal. A liposome according to the present invention comprises a lipid composition that is capable of fusing with the plasma membrane of the targeted cell to deliver a nucleic acid molecule into a cell. Suitable liposomes for use with the present invention include any liposome. Preferred liposomes of the present invention include those liposomes typically used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule or inhibitory agent of the present invention can be achieved using methods standard in the art.

Another delivery vehicle comprises a viral vector. A viral vector includes an isolated nucleic acid molecule useful in the method of the present invention, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

In accordance with the present invention, determination of acceptable protocols to administer an agent, composition or formulation, including the route of administration and the effective amount of an agent to be administered to an animal, can be accomplished by those skilled in the art. An agent of the present invention can be administered in vivo or ex vivo. Suitable in vivo routes of administration can include, but are not limited to, oral, nasal, inhaled, topical, intratracheal, transdermal, rectal, and parenteral routes. Preferred parenteral routes can include, but are not limited to, subcutaneous, intradermal, intravenous, intramuscular, and intraperitoneal routes. Preferred topical routes include inhalation by aerosol (i.e., spraying) or topical surface administration to the skin of an animal. Preferably, an agent is administered by nasal, inhaled, intratracheal, topical, or systemic routes (e.g., intraperitoneal, intravenous). Ex vivo refers to performing part of the administration step outside of the patient. Preferred routes of administration for antibodies include parenteral routes and aerosol/nasal/inhaled routes.

Intravenous, intraperitoneal, and intramuscular administrations can be performed using methods standard in the art. Aerosol (inhalation) delivery can be performed using methods standard in the art (see, for example, Stribling et al., *Proc. Natl. Acad. Sci. USA* 189:11277-11281, 1992, which is incorporated herein by reference in its entirety). Carriers suitable for aerosol delivery are described above. Devices for delivery of aerosolized formulations include, but are not limited to, pressurized metered dose inhalers (MDI), dry powder inhalers (DPI), and metered solution devices (MSI), and include devices that are nebulizers and inhalers. Oral delivery can be performed by complexing a therapeutic composition of the present invention to a carrier capable of withstanding degradation by digestive enzymes in the gut of an animal. Examples of such carriers, include plastic capsules or tablets, such as those known in the art. Direct injection techniques are particularly useful for administering a recombinant nucleic acid molecule to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell or tissue, whereby the nucleic acid molecule transfected the cell and was expressed. In many studies, successful delivery and expression of a heterologous gene was achieved in preferred cell types and/or using preferred delivery vehicles and routes of administration of the present invention. For example, using liposome delivery, U.S. Pat. No. 5,705,151, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. Liu et al., 1997 demonstrated that intravenous delivery of cholesterol-containing cationic liposomes containing genes preferentially targets pulmonary tissues and effectively mediates transfer and expression of the genes in vivo. Delivery of numerous nucleic acid sequences has been accomplished by administration of viral vectors encoding the nucleic acid sequences.

A preferred single dose of an agent, including proteins, small molecules and antibodies, for use in any method described herein, comprises between about 0.01 microgram× kilogram$^{-1}$ and about 10 milligram×kilogram$^{-1}$ body weight of an animal. A more preferred single dose of an agent comprises between about 1 microgram×kilogram$^{-1}$ and about 10 milligram×kilogram$^{-1}$ body weight of an animal. An even more preferred single dose of an agent comprises between about 5 microgram×kilograms$^{-1}$ and about 7 milligram×kilogram$^{-1}$ body weight of an animal. An even more preferred single dose of an agent comprises between about 10 microgram×kilogram$^{-1}$ and about 5 milligram×kilogram$^{-1}$ body weight of an animal. A particularly preferred single dose of an agent comprises between about 0.1 milligram×kilogram$^{-1}$ and about 5 milligram×kilogram$^{-1}$ body weight of an animal, if the an agent is delivered by aerosol. Another particularly preferred single dose of an agent comprises between about 0.1 microgram×kilograms$^{-1}$ and about 10 microgram×kilogram$^{-1}$ body weight of an animal, if the agent is delivered parenterally.

In one embodiment, an appropriate single dose of a nucleic acid:liposome complex of the present invention is from about 0.1 μg to about 100 μg per kg body weight of the patient to which the complex is being administered. In another embodiment, an appropriate single dose is from about 1 μg to about 10 μg per kg body weight. In another embodiment, an appropriate single dose of nucleic acid:lipid complex is at least about 0.1 μg of nucleic acid, more preferably at least about 1 μg of nucleic acid, even more preferably at least about 10 μg of nucleic acid, even more preferably at least about 50 g of nucleic acid, and even more preferably at least about 100 μg of nucleic acid.

In one embodiment a suitable dose of an agent of the present invention for use in any method described herein is a dose effective to inhibit the expression or activity of at least one protein in the alternative complement pathway as described herein (e.g., factor B, factor D or properdin), as compared to in the absence of the administration of the agent. Methods of measuring the expression or biological activity of a protein have been described above. In another embodiment, a suitable dose of an agent of the present invention is a dose that measurably inhibits the alternative complement pathway of the invention. Activation of complement and inhibition thereof can be measured using techniques/assays that are well-known in the art. For example, one can perform an in vitro analysis of C3 deposition on zymosan A particles as described in the examples. One can also test the ability of the agent to inhibit lysis of unsensitized erythrocytes by human serum. Extrapolation of in vitro results to in vivo dosages based on these assays is within the ability of those of skill in the art.

In humans, it known in the art that, using conventional methods for aerosol delivery, only about 10% of the delivered solution typically enters the deep airways, even using an inhaler. If the aerosolized delivery is by direct inhalation, one may assume a dosage of about 10% of that administered by nebulization methods. Finally, one of skill in the art will readily be capable of converting a mouse dosage to a human dosage using alometric scaling. Essentially, a scale of dosage from mouse to human is based on the clearance ratio of a compound and the body surface of the mouse. The conversion for mg/kg is 1/12th of the "no observed adverse event level" (NOEL) to obtain the concentration for human dosage. This calculation assumes that the elimination between mouse and human is the same, which is believed to be the case for antibodies.

Accordingly, a preferred single dose of an antibody comprises between about 1 ng×kilogram$^{-1}$ and about less than 1 mg×kilogram$^{-1}$ body weight of an animal. A more preferred single dose of an antibody comprises between about 20 ng×kilogram$^{-1}$ and about 600 μg×kilogram$^{-1}$ body weight of the animal. An even more preferred single dose of an antibody, particularly when the antibody formulation is delivered by nebulization, comprises between about 20 ng×kilogram$^{-1}$ and about 600 μg×kilograms$^{-1}$ body weight of the animal, and more preferably, between about 20 ng×kilogram$^{-1}$ and about 500 μg×kilogram$^{-1}$, and more preferably, between about 20 ng×kilogram$^{-1}$ and about 400 μg×kilogram$^{-1}$, and more preferably, between about 20 ng×kilogram$^{-1}$ and about 300 μg×kilogram$^{-1}$, and more preferably, between about 20 ng×kilogram$^{-1}$ and about 200 μg×kilogram$^{-1}$, and more preferably, between about 20 ng×kilogram$^{-1}$ and about 100 μg×kilogram$^{-1}$, and more preferably, between about 20 ng×kilogram$^{-1}$ and about 50 μg×kilogram$^{-1}$ body weight of the animal.

Another preferred single dose of an antibody, particularly when the antibody formulation is delivered by nebulization, comprises between about 200 ng×kilogram$^{-1}$ and about 600 μg×kilogram$^{-1}$ body weight of the animal, and more preferably, between about 200 ng×kilogram$^{-1}$ and about 500 μg×kilogram$^{-1}$, and more preferably, between about 200 ng×kilogram$^{-1}$ and about 400 μg×kilogram$^{-1}$, and more preferably, between about 200 ng×kilogram$^{-1}$ and about 300 μg×kilogram$^{-1}$, and more preferably, between about 200 ng×kilogram$^{-1}$ and about 200 μg×kilogram$^{-1}$, and more preferably, between about 200 ng×kilogram$^{-1}$ and about 100 μg×kilogram$^{-1}$, and more preferably, between about 200 ng×kilogram$^{-1}$ and about 50 μg×kilogram$^{-1}$ body weight of the animal.

Another preferred single dose of an antibody, particularly when the antibody formulation is delivered by direct inhalation from an inhaler, comprises between about 2 ng×kilogram$^{-1}$ and about 100 μg×kilogram$^{-1}$ body weight of the animal, and more preferably, between about 2 ng×kilograms$^{-1}$ and about 50 μg×kilogram$^{-1}$, and more preferably, between about 2 ng×kilogram$^{-1}$ and about 10 μg×kilogram$^{-1}$, and more preferably, between about 2 ng×kilogram$^{-1}$ and about 5 μg×kilogram$^{-1}$, and more preferably, between about 2 ng×kilogram$^{-1}$ and about 1 μg×kilogram$^{-}$, and more preferably, between about 2 ng×kilogram$^{-1}$ and about 0.5 μg×kilogram$^{-1}$, and more preferably, between about 2 ng×kilogram$^{-1}$ and about 0.25 μg×kilogram$^{-1}$, and more preferably, between about 2 ng×kilogram$^{-1}$ and about 0.1 μg×kilogram$^{-1}$ body weight of the animal.

In another embodiment, the antibody is administered at a dose of less than about 500 μg antibody per milliliter of formulation, and preferably, less than about 250 μg antibody per milliliter of formulation, and more preferably, less than about 100 μg antibody per milliliter of formulation, and more preferably, less than about 50 μg antibody per milliliter of formulation, and more preferably, less than about 40 μg antibody per milliliter of formulation, and more preferably, less than about 30 μg antibody per milliliter of formulation, and more preferably, less than about 20 μg antibody per milliliter of formulation, and more preferably, less than about 10 μg antibody per milliliter of formulation, and even more preferably, between about 5 μg antibody and about 10 μg antibody per milliliter of formulation.

With more particular regard to the method of reducing or preventing airway hyperresponsiveness and/or airway inflammation or a condition or disease related thereto, a suitable single dose of an inhibitory agent to administer to an animal is a dose that is capable of reducing or preventing airway hyperresponsiveness and/or airway inflammation, or reducing at least one other symptom of a disease to be treated (e.g., asthma), in an animal when administered one or more times over a suitable time period. When the patient has or is at risk of developing AHR, a suitable single dose of an agent comprises a dose that improves AHR by a doubling dose of a provoking agent or improves the static respiratory function of an animal.

According to the method of the present invention, an effective amount of an agent that inhibits AHR to administer to an animal comprises an amount that is capable of reducing airway hyperresponsiveness (AHR) or airway inflammation without being toxic to the animal. An amount that is toxic to an animal comprises any amount that causes damage to the structure or function of an animal (i.e., poisonous).

In one embodiment, the effectiveness of an AHR inhibiting agent to protect an animal from AHR in an animal having or at risk of developing AHR can be measured in doubling amounts. For example, the ability of an animal to be protected from AHR (i.e., experience a reduction in or a prevention of) by administration of a given agent is significant if the animal's $PC_{20methacholine}FEV_1$ is at 1 mg/ml before administration of the agent and is at 2 mg/ml of Mch after administration of the agent. Similarly, an agent is considered effective if the animal's $PC_{20methacholine}FEV_1$ is at 2 mg/ml before administration of the agent and is at 4 mg/ml of Mch after administration of the agent. A preferred effective amount of an agent comprises an amount that is capable of increasing the $PC_{20methacholine}FEV_1$ of an animal treated with the agent by about one doubling concentration towards the $PC_{20methacholine}FEV_1$ of a normal animal. As discussed above, a normal animal refers to an animal known not to suffer from or be susceptible to abnormal AHR. A test animal refers to an animal suspected of suffering from or being susceptible to abnormal AHR.

In one embodiment of the present invention, in an animal that has AHR, an effective amount of an agent to administer to an animal is an amount that measurably reduces AHR in the animal as compared to prior to administration of the agent. In another embodiment, an effective amount of an agent to administer to an animal is an amount that measurably reduces AHR in the animal as compared to a level of airway AHR in a population of animals with inflammation that is associated with AHR wherein the agent was not administered. The agent is preferably capable of reducing AHR in an animal, even when the agent is administered after the onset of the physical symptoms of AHR (i.e., after acute onset AHR). Most preferably, an effective amount of the agent is an amount that reduces the symptoms of AHR to the point where AHR is no longer detected in the patient. In another embodiment, an effective amount of the agent is an amount that prevents, or substantially inhibits the onset of AHR when the agent is administered prior to exposure of the patient to an AHR provoking stimulus, such as an allergen, in a manner sufficient to induce AHR in the absence of the agent.

In another embodiment, an effective amount of an agent according to the method of the present invention, comprises an amount that results in an improvement in an animal's $PC_{20methacholine}FEV_1$ value such that the $PC_{20methacholine}FEV_1$ value obtained before administration of the agent when the animal is provoked with a first concentration of methacholine is the same as the $PC_{20methacholine}FEV_1$ value obtained after administration of the agent when the animal is provoked with double the amount of the first concentration of methacholine. A preferred amount of an agent comprises an amount that results in an improvement in an animal's $PC_{20methacholine}FEV_1$ value such that the $PC_{20methacholine}FEV_1$ value obtained before administration of the agent is between about 0.01 mg/ml to about 8 mg/ml of methacholine is the same as the $PC_{20methacholine}FEV_1$ value obtained after administration of the agent is between about 0.02 mg/ml to about 16 mg/ml of methacholine.

As previously described herein, the effectiveness of an agent to protect an animal having or susceptible to AHR can be determined by measuring the percent improvement in $FEV_1$ and/or the $FEV_1/FVC$ ratio before and after administration of the agent. In one embodiment, an effective amount of an agent comprises an amount that is capable of reducing the airflow limitation of an animal such that the $FEV_1/FVC$ value of the animal is at least about 80%. In another embodiment, an effective amount of an agent comprises an amount that is capable of reducing the airflow limitation of an animal such that the $FEV_1/FVC$ value of the animal is improved by at least about 5%, or at least about 100 cc or PGFRG 10 L/min. In another embodiment, an effective amount of an agent comprises an amount that improves an animal's $FEV_1$ by at least about 5%, and more preferably by between about 6% and about 100%, more preferably by between about 7% and about 100%, and even more preferably by between about 8% and about 100% (or about 200 ml) of the animal's predicted $FEV_1$. In another embodiment, an effective amount of an agent comprises an amount that improves an animal's $FEV_1$ by at least about 5%, and preferably, at least about 10%, and even more preferably, at least about 25%, and even more preferably, at least about 50%, and even more preferably, at least about 75%.

One of skill in the art will be able to determine that the number of doses of an agent to be administered to an animal is dependent upon the extent of the airway hyperresponsiveness and the underlying condition of which AHR is a symptom, and the response of an individual patient to the treatment. In addition, the clinician will be able to determine the appropriate timing for delivery of the agent in a manner effective to reduce AHR in the animal. Preferably, the agent is delivered within 48 hours prior to exposure of the patient to an amount of an AHR provoking stimulus effective to induce AHR, and more preferably, within 36 hours, and more preferably within 24 hours, and more preferably within 12 hours, and more preferably within 6 hours, 5 hours, 4 hours, 3 hours, 2 hours, or 1 hour prior to exposure of the patient to an amount of AHR provoking stimulus effective to induce AHR. In one embodiment, the agent is administered as soon as it is recognized (i.e., immediately) by the patient or clinician that the patient has been exposed or is about to be exposed to an AHR provoking stimulus, and especially an AHR provoking stimulus to which the patient is sensitized (i.e., an allergen). In another embodiment, the agent is administered upon the first sign of development of AHR (i.e., acute onset AHR), and preferably, within at least 2 hours of the development of symptoms of AHR, and more preferably, within at least 1 hour, and more preferably within at least 30 minutes, and more preferably within at least 10 minutes, and more preferably within at least 5 minutes of development of symptoms of AHR. Symptoms of AHR and methods for measuring or detecting such symptoms have been described in detail above. Preferably, such administrations are given until signs of reduction of AHR appear, and then as needed until the symptoms of AHR are gone.

With particular regard to the method of inhibiting or preventing ischemia-reperfusion injury, an effective amount of an agent, and particularly a factor B antibody or antigen binding fragment thereof (or antigen binding polypeptide) to administer to an animal is an amount that measurably inhibits histological damage, including oxidative damage or cell death, in the animal as compared to in the absence of administration of the agent. In the case of renal ischemia-reperfusion injury, an effective amount of an agent to administer to an animal is an amount that measurably inhibits increases in serum urea nitrogen or measurably decrease histologic injury to the tissues of the kidney of the animal as compared to in the absence of administration of the agent. A suitable single dose of an inhibitory agent to administer to an animal is a dose that is capable of reducing or preventing at least one symptom, type of injury, or resulting damage, from ischemia-reperfusion injury in an animal when administered one or more times over a suitable time period. Suitable doses of antibodies, including for various routes of administration, are described in detail above. In one aspect, an effective amount of an agent that inhibits ischemia-reperfusion injury to administer to an animal comprises an amount that is capable of inhibiting at least one symptom or damage caused by ischemia-reperfusion injury without being toxic to the animal.

Any of the methods of the present invention can be used in any animal, and particularly, in any animal of the Vertebrate class, Mammalia (i.e., mammals), including, without limitation, primates, rodents, livestock and domestic pets. Preferred mammals to treat using the method of the present invention are humans.

The following examples are provided for the purposes of illustration and are not intended to limit the scope of the present invention.

EXAMPLES

Example 1

The following example describes the production of a novel inhibitor of the alternative complement pathway.

The present inventors have created several hybridomas that produce mouse monoclonal antibodies that bind mouse factor B. In this study, the inventors set out to characterize the ability of one of these antibodies to inhibit the alternative complement pathway. The inventors also tested this antibody in a model of antiphospholipid mediated fetal loss. As previously reported (Girardi), mice deficient in factor B were greatly protected from fetal loss in this model, and the inventors hypothesized that an exogenous inhibitor of the alternative pathway would be an effective therapeutic agent in this disease model.

Methods

Construction of a factor B-Ig fusion protein and purification of mouse factor B. A plasmid encoding two of the short consensus repeats (SCR) of the factor B gene linked to the hinge, CH2, and CH3 domains of a mouse IgG1 isotype was constructed (FIG. 1). These SCR domains were chosen because they are part of the deleted segment of the factor B gene in the fB−/− mice used in these studies.

Purification of mouse factor B. Complement factor B was purified from normal mouse serum by affinity purification. The affinity column was created by binding goat anti-human properdin factor B (Diasorin, Stillwater, Minn.) to CNBr-Activated Separose (Amersham, Arlington Heights, Ill.) according to the manufacturer's instructions. C57/B6J mice were bled by cardiac puncture, and the blood was collected into syringes containing 50 µl of 500 mM EDTA in order to prevent alternative pathway activation. The blood was centrifuged at 2000 rpm for 15 minutes and the plasma was collected. The plasma was then diluted 1:1 with buffer (EACA 50 mM, EDTA 10 mM, benzamidine 2 mM in PBS, pH 7.4) and passed through a 0.22 μm filter (GE Water Technologies). The plasma was added to the affinity column and the column was washed with 10 column volumes of buffer. The factor B was eluted using 5 M LiCl$_2$ and dialyzed overnight against PBS. The purity of the factor B was then checked by electrophoresis on a 10% Tris-Glycine gel and stained with Coomassie (data not shown).

Development of inhibitory monoclonal antibodies targeting complement factor B. Targeted deletion of mouse factor B was accomplished as previously described (Matsumoto). The factor B deficient mice were created with Sv129 strain embryonic stem cells and were then crossed with C57BL/6 mice prior to expansion of the colony at F1. Factor B deficient mice were immunized with 125 μg of the recombinant factor B-Ig fusion protein emulsified with Freund's incomplete adjuvant and then boosted four times at three week intervals. The mice were screened for the development of inhibitory antibodies to factor B by testing their sera in an enzyme linked immunosorbant assay (ELISA) using mouse factor B coated plates and an in vitro assay of alternative complement pathway inhibition (described below). One day after the last injection, spleen cells from a mouse identified as having a robust immune response towards factor B were fused to the myeloma cell line in the University of Colorado Monoclonal Antibody Center. Candidate hybridomas were cloned by limiting dilution, and clones capable of inhibiting alternative pathway activity were identified. One of the hybridomas, A1379, was used for these experiments. A1379 was purified from tissue culture supernatant with a Protein-G Sepharose® column (Pharmacia, Uppsala, Sweden). LPS was removed from the purified mAb using polymyxin (Sigma). The Limulus Amebocyte Lysate Assay (BioWhittaker, Inc., Walkersville, Md.) was used according to the manufacturers instructions to verify that the mAb had LPS levels below 1 EU/mg of mAb. The purity of the mAb was then checked by electrophoresis on a 10% Tris-Glycine gel and stained with Coomassie.

ELISA Analysis of Anti-factor B Antibody Levels.

Mice were screened for an immune response to the immunizations by testing their sera in an enzyme linked immunosorbant assay (ELISA) against purified factor B. Ninety-six well ELISA plates (Costar, Corning, N.Y.) were coated with 125 ng of purified factor B in coating buffer (15 mM Na$_2$CO$_3$, 35 mM Na$_2$HCO$_3$) and stored overnight at 4° C. The plates were then washed with 200 μl of PBS. Non-specific binding was blocked by incubating the plates with 200 μl of 5% BSA (Sigma-Aldrich, St. Louis, Mo.) in PBS. The plates were washed two times with 200 μl of PBS with 0.1% Tween 20, then incubated with diluted serum for one hour. Samples were diluted 1:100 in PBS with 0.1% Tween-20 and 0.1% BSA, then the samples were further serially diluted 1:1 seven times. The plates were then washed two times and incubated with 50 μl of peroxidase conjugated goat anti-mouse IgG (Cappel, Durham, N.C.). The plates were next washed four times and incubated with 100 μl of ABTS containing 1:1000 30% H$_2$O$_2$ (Sigma), and absorbance at 405 nm was read with a microplate reader (Biorad, Richmond, Calif.).

Assays of alternative complement pathway inhibition. Sera with detectable titers of anti-factor B antibodies were then screened for the ability to inhibit the alternative pathway. This was performed using an in vitro analysis of C3 deposition on zymosan A particles (Sigma) (Quigg). Fifty mg of zymosan particles in 10 ml of 0.15 M NaCl were boiled for 60 minutes, then washed twice in PBS. Sera was assayed by mixing 1×10$^7$ zymosan particles in a reaction mix with a final concentration of 10 mM EGTA and 5 mM MgCl$_2$. Ten microliters of sera from unmanipulated C57/B6 mice were added as a source of complement were added. Assays of inhibition were conducted with up to 70 μl of sera from immunized mice (to screen for the generation of inhibitory antibodies) or with purified antibody titrated from 0.0625 μg to 8 μg per reaction. Samples were brought up to 100 μl final volume with PBS and were incubated at 37° C. for 30 minutes. The zymosan particles were washed twice with cold PBS, 1% fetal bovine serum, and were then incubated with FITC-conjugated goat anti-mouse C3 (Cappel, Durham, N.C.) for one hour on ice. The samples were again washed twice, were resuspended in 0.5 ml of PBS, 1% fetal bovine serum, and were then analyzed by flow cytometry. Percent inhibition was calculated using the formula:

$$100 \times \left[1 - \frac{\text{(sample mean channel fluorescence} - \text{background (no serum))}}{\text{(positive control mean channel fluorescence} - \text{background)}}\right]$$

Fab fragments of the 1379 clone were also tested for the ability to inhibit the alternative pathway using the zymosan assay. Fab fragments were generated by incubating purified antibody with papain-agarose (ICN Biomedicals, Aurora, Ohio) according to the manufacturer's instructions. Fc fragments and undigested IgG were then removed by applying the digested antibody to a protein G column. The Fab fragments were collected in the flow through, and the Fc fragments and undigested IgG were subsequently eluted with 0.1 M glycine-HCl, pH 2.8. One μg of the Fab was used in the zymosan reaction. The polyclonal anti-mouse C3 antibody used in this assay was found to have cross reactivity with multiple species. This assay was therefore used to test inhibition by the 1379 clone of the alternative pathway in those species. Titration of the inhibitory antibody was conducted as described above.

As another assay of the ability of the 1379 clone to inhibit the alternative complement pathway, the inventors tested the ability of this antibody to inhibit lysis of unsensitized rabbit erythrocytes by human serum. Whole rabbit blood was mixed 1:1 with a buffer solution composed of 20.5 g dextrose, 8.0 g sodium citrate (dihydrate), 4.0 g NaCl, 0.55 g citric acid in one liter of distilled water. Five ml of the erythrocyte solution was then mixed 1:9 with a solution of 1.1% NaCl, 0.0025% Na-5,5 diethyl barbiturate, pH 7.35, 8 mM EGTA, 2 mM MgCl$_2$. The mixture was incubated at 37° C. for several minutes then centrifuged at 1000×g for 10 minutes at 4° C. The erythrocytes were washed three more times before being resuspended in 40 ml of the same solution. Fifty μl of the above suspension was added to human serum (5 to 100 μl) buffer solution was added to bring the final volume up to 150 μl. Erythrocytes in buffer without serum were used as a negative control, and erythrocytes added to 100 μl of distilled water were used as positive controls (complete lysis). Samples were incubated at 37° C. for 30 minutes with occasional shaking to keep the cells in suspension. The reactions were stopped by adding 1.5 ml of cold PBS and the samples were spun at 1000×g for five minutes. The optical density of each supernatant was read at 415 nm using a spectrophotometer (Biorad). Ten µl of serum were found to cause complete lysis of the erythrocytes. The same reaction was then carried out using 10 µl of the serum and increasing concentrations of the 1379 clone (1 µg to 12 µg per reaction). Percent inhibition of alternative pathway activity was determined using the formula:

$$100 \times \left[1 - \frac{(OD_{sample} - OD_{background})}{(OD_{positive\ control} - OD_{background})}\right]$$

In Vivo pharmacokinetics of the 1379 clone. Mice were pre-bled, and then were injected intraperitoneally (IP) or intravenously (IV) with one or two mg doses of the 1379 clone of antibody. These doses were chosen because it was estimated that they would be equimolar with factor B. Factor B is present in the serum at approximately ~200 µg/ml (or ~2.2 µM given that factor B is a 90 kD protein). Because the 1379 antibody is 150 kD and the intravascular volume of an adult mouse is approximately 3 ml, a one mg injection (6.7 µMol) should result in a circulating concentration of ~2.2 µM. Because the antibody is divalent, it was anticipated that this equimolar injection would be more than sufficient to result in complete inhibition of the alternative pathway. The mice were bled 1, 2, 6, 24, 48, and 96 hours after the injection of the inhibitor. Sera from these time points were then used in the zymosan assay to assess the activity of the alternative pathway.

Results

Figure 2A:
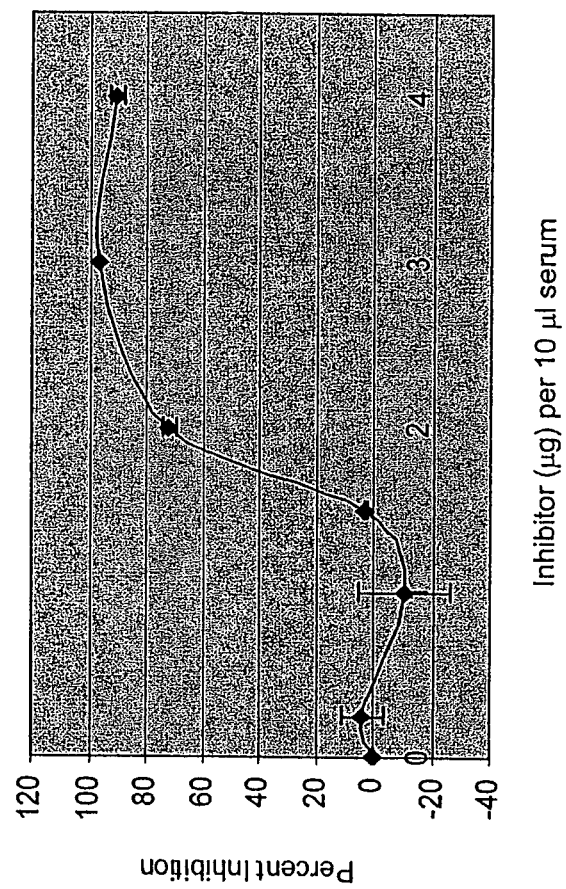
FIG. 2A is a line graph showing that anti-factor B completely inhibited the alternative complement pathway in a zymosan assay when 3 μg were added to a reaction containing 10 μl of serum.
Figure 2B:
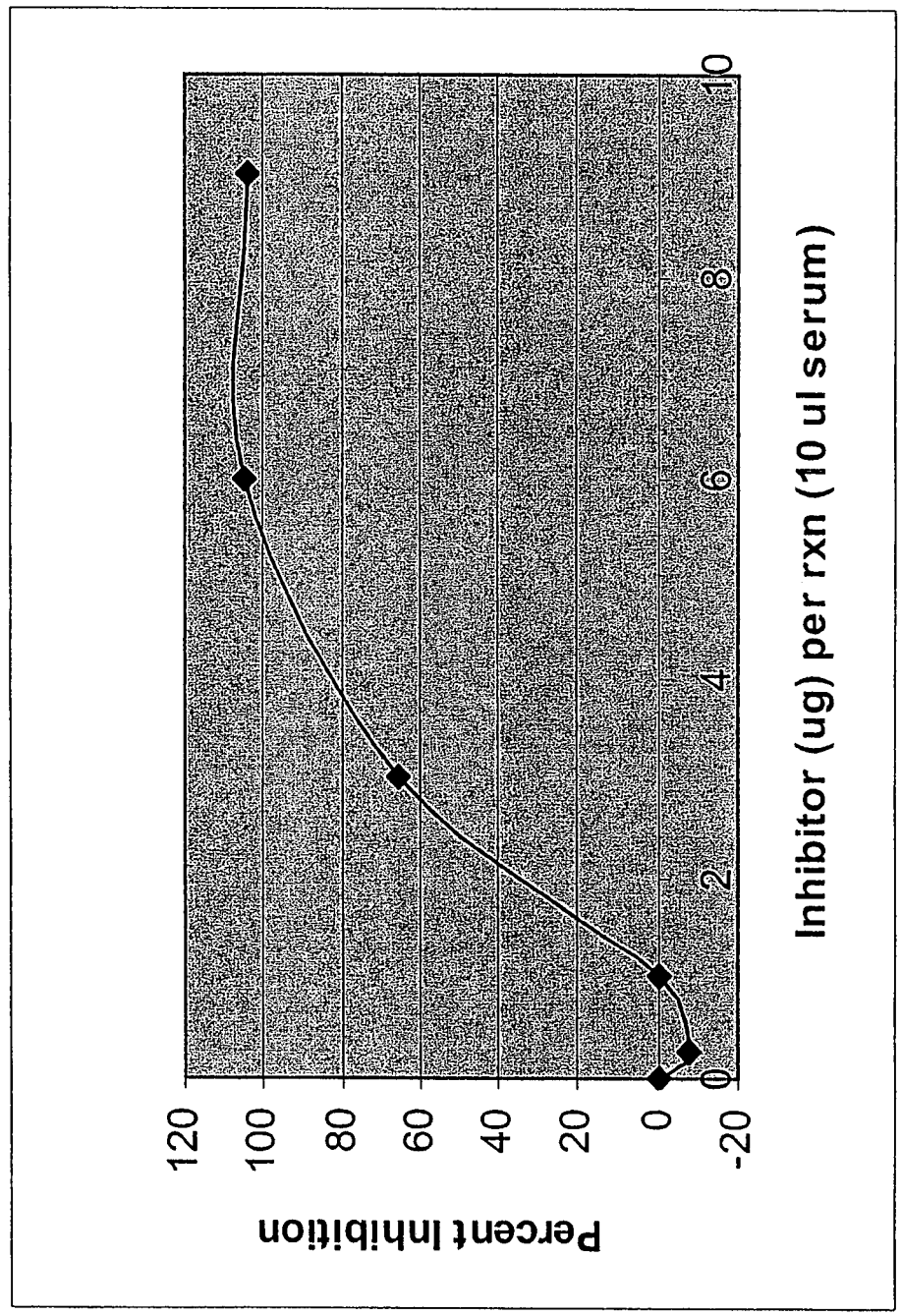
FIG. 2B is a line graph showing that anti-factor B completely inhibited the alternative complement pathway in a rabbit erythrocyte lysis assay when 6 μg of antibody were added to 10 μl of human serum.

Generation of inhibitory monoclonal antibodies to the Ba portion of factor B. Monoclonal antibodies to mouse factor B were generated as described in the methods section. Serum from immunized mice were assayed for the presence of anti-factor B antibodies (data not shown). One clone, designated 1379, was chosen for further characterization due to the fact that the hybridoma was found to be rapidly growing, the antibody is of the $IgG_1$ subclass (non-complement activating), and its supernatant was found to be a potent inhibitor of the alternative complement pathway. After purification of the antibody (data not shown), the antibody was tested in two in vitro assays of alternative pathway activity (FIGS. 2A and 2B). Using the zymosan assay the inhibitor was found to completely inhibit the alternative pathway when three µg were added to a reaction containing 10 µl of serum. The anti-factor B and the factor B are approximately equimolar at this concentration (Assuming that factor B is present at 200 µg/ml and has a molecular weight of 90,000 kD, there are 0.022 nMol in 10 µl of serum, and 3 µg of antibody with a molecular weight of 150,000 kD equals approximately 0.02 nMol). In the rabbit erythrocyte lysis assay, full inhibition was achieved with 6 µg of antibody per 10 µl of human serum in the reaction. Inhibition of the alternative pathway was next tested using Fab fragments made from the 1379 clone. When a molar excess of Fab from the 1379 clone was used, complete inhibition of alternative pathway activity was seen by this assay.

The ability of 1379 to inhibit alternative pathway activity in sera from multiple different mammalian species was next tested in the zymosan assay. The 1379 antibody was able to fully inhibit alternative pathway activation in most of the species tested (Table 1). The antibody fully inhibited alternative pathway activity in serum from mice, rats, humans, and several species of monkeys. However, it did not demonstrate any inhibitory activity towards serum from dogs or guinea pigs.

TABLE 1

Species in which the alternative pathway is fully inhibited by mAb 1379

Mouse
Human
Rat
Baboon
Rhesus
Pig
Cyno Monkey
Horse

Species in which the alternative pathway is not inhibited by mAb 1379

Dog
Guinea Pig

Figure 3:
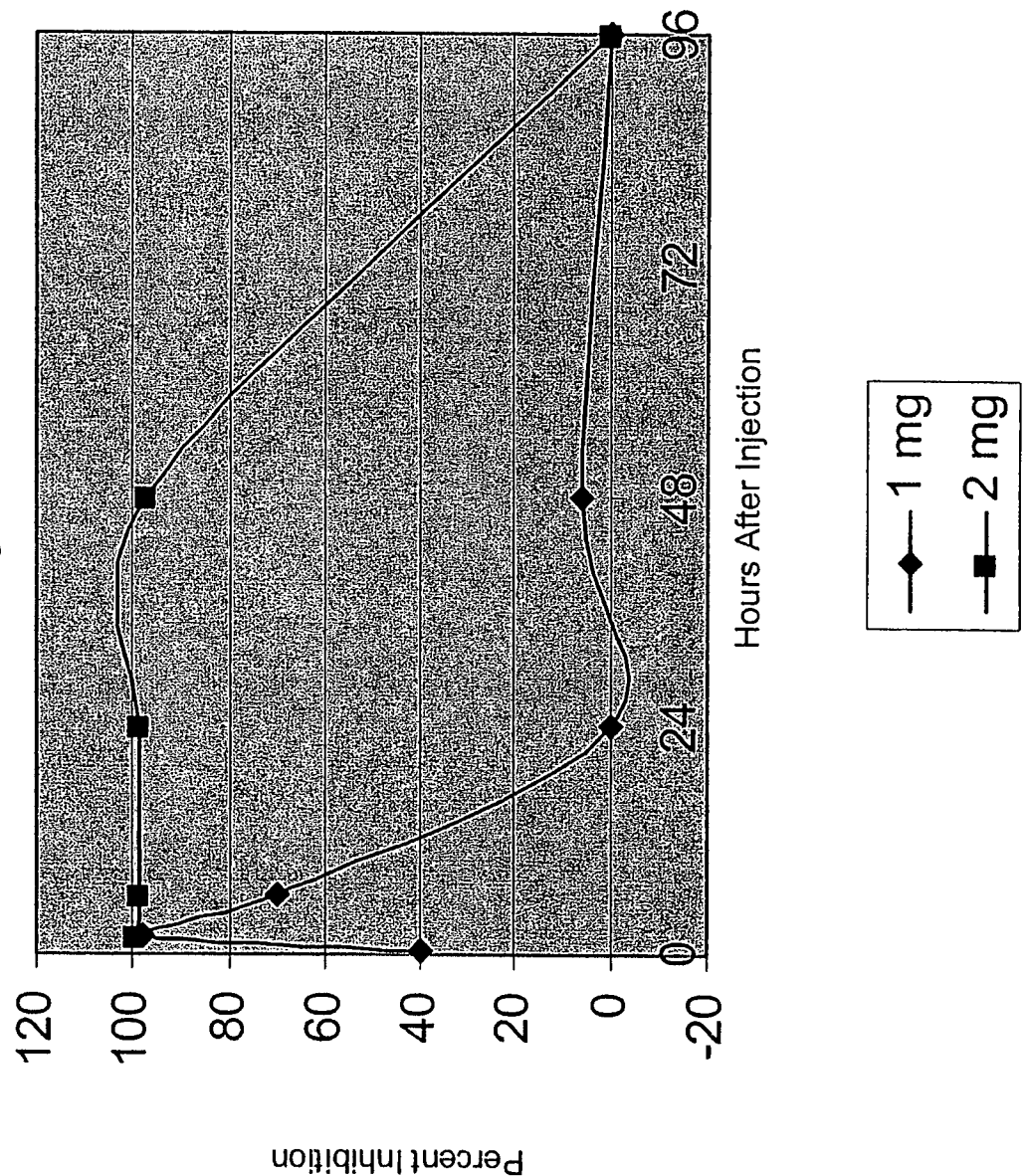
FIG. 3 is a line graph showing that administration of anti-factor B to mice inhibits the alternative complement pathway.

Pharmacokinetics of the 1379 antibody. Mice were tested for inhibition of the alternative pathway at various times after a single injection of the inhibitory antibody. One mg of antibody led to full inhibition within one hour when injected IV and within two hours when injected IP (FIG. 3). Mice receiving a one mg injection IP retained full inhibition of the alternative pathway at 24 hours and those receiving a two mg injection retained full inhibition up to 48 hours after the injection. The inventors have also injected 2 mg of the 1379 antibody repetitively i.p. every other day for 14 days and have shown that the complete inhibition of the alternative complement pathway was maintained for at least 48 hours after the last injection (data not shown). These data strongly suggest that this mouse mAb is not recognized as "foreign" and supports its chronic usage in vivo. Finally, experiments using F(ab) fragments of the antibody has shown that inhibition of the alternative pathway is achieved in approximately equimolar levels as with the intact 1379 antibody (data not shown).

1379 binds an epitope in the SCR3 region of Ba. The ability of the 1379 antibody to bind to a panel of factor B mutants was performed as previously described (Hourcade, 1995, *J. Biol. Chem.*) in order to characterize the mAb binding site. Experiments have shown that the introduction of certain alanine substitutions into SCRs 2 and 3 of human factor B, but not SCR1, results in the loss of binding of the 1379 antibody to factor B. From the 25 different mutants tested, 1379 had virtually no binding to the B17 and B23 mutants and retained less than 20% of its binding capability to the B18 mutant. These are all SCR3 mutations. More specifically, mutant B17 substitutes 139-Tyr-140-Cys-141-Ser with His-Cys-Pro, the positions being relevant to the mature human factor B represented by SEQ ID NO:2; mutant B23 substitutes 182-Glu-183-Gly-184-Gly-185-Ser with Gly-Asn-Gly-Val, the positions also relevant to the mature human factor B represented by SEQ ID NO:2. Therefore, the 1379 antibody binds to the third SCR domain of factor B.

Conclusions

The present inventors have generated a novel monoclonal antibody to mouse factor B identified as clone 1379. This antibody is a specific inhibitor of the alternative pathway of complement and leads to complete inhibition of this pathway in vitro and in vivo. A single 1 mg i.p. injection led to complete inhibition of the alternative pathway for up to 48 hours, and multiple injections resulted in prolonged inhibition of this pathway.

Using in vitro assays, 1379 was demonstrated to fully inhibit alternative pathway activity in serum from multiple species including mice, rats, monkeys and humans. Using assays of the binding affinity for the antibody to a panel of factor B mutants, the antigenic site was determined to be in the SCR3 domain of factor B, part of the region deleted in the fB−/− mice. This region of the factor B protein is adjacent to the factor D cleavage site. The ability of the Fab fragment of 1379 to inhibit alternative pathway activity suggests that the it is not merely steric hindrance by 1379 that prevents cleavage but that the specific binding site is a critical location in factor D mediated cleavage of the protein. The efficacy of 1379 against the serum from so many different species suggests that this site is highly conserved among higher mammals.

Several other soluble complement inhibitors have already been developed and characterized (Quigg; Weisman; Heller; Granger; Pratt), but the inhibitor described herein is believed to be the first that selectively inhibits the alternative pathway in a broad range of animal species. By selectively inhibiting the alternative pathway, 1379 may have several advantages compared to inhibitors that work at the level of the C3 convertase. By leaving the classical pathway intact, this inhibitor may have fewer immunosuppressive affects. Furthermore, blockade of the classical pathway may actually induce autoimmunity. Selective blockade of the alternative pathway has ameliorated a mouse model of lupus nephritis (Watanabe), whereas C3 deficiency did not. The alternative pathway has been specifically implicated in a number of disease models (Thurman; Watanabe; Girardi), highlighting the therapeutic potential of a specific alternative pathway inhibitor.

REFERENCES

1. Thurman et al., 2003, *J Immunol* 170:1517-1523
2. Watanabe et al., 2000, *J Immunol* 164:786-794
3. Girardi et al., 2003, *J Clin Invest* 112:1644-1654
4. Holers, V. M. 2003, *Clin Immunol* 107:140-151
5. Densen et al., 1996, *Mol Immunol* 33:68 (Abstract 270)
6. Matsumoto et al., 1997, *Proc Natl Acad Sci USA* 94:8720-8725
7. Figueroa and Densen, 1991, *Clin Microbiol Rev* 4:359-395
8. Quigg et al., 1998, *J Immunol* 160:4553-4560
9. Weisman et al., 1990, *Science* 249:146-151
10. Heller et al., 1999, *J Immunol* 163:985-994
11. Granger et al., 2003, *Circulation* 108:1184-1190
12. Pratt et al., 2003, *Am J Pathol* 163:1457-1465

Example 2

The following example demonstrates that complement activation through the alternative pathway is critical for development of airway hyperresponsiveness and inflammation, and further demonstrates that inhibition of the alternative pathway for complement activation inhibits airway hyperresponsiveness.

Given the effectiveness of inhibition of complement activation before allergen exposure, the present inventors further determined the pathway of complement activation. In the present study the inventors report that activation of the complement cascade through the alternative pathway is critical for the development of airway hyperresponsiveness and airway inflammation.

Methods
Animals

Female C57BL/6 mice, 8 to 12 weeks of age, were obtained from Jackson Laboratories (Bar Harbor, Me.). As previously described, factor B heterozygote deficient mice (fB+/−) were intercrossed at F1 following an initial cross to C57BL/6 strain and then intercrossed to generate and fB−/− strain. These mice were then backcrossed for 7 generations with C57BL/6 mice. As control mice, congenic fB+/+ littermates were used. C4 deficient mice ((C4−/−) backcrossed for 17 generations with C57BL/6 mice) were maintained in the animal facility. All experimental animals used in this study were maintained on ovalbumin (OVA)-free diets and were under a protocol approved by the Institutional Animal Care and Use Committee of the National Jewish Medical and Research Center.

Experimental Protocol

Mice were sensitized by intraperitoneal injection (i.p.) of 20 µg of OVA (Grade V; Sigma Chemical Co., St. Louis, Mo.) or ragweed (*Ambrosia artemisiifolia*, Greer Laboratories, Lenoir, N.C.) suspended in 2.25 mg aluminum hydroxide (Alum Imuject; Pierce, Rockford, Ill.) on days 1 and 14 and then challenged via the airways, using nebulized OVA or ragweed (1% in PBS), with an ultrasonic nebulizer (DeVilbiss Health Care, Somerset, Pa.) for 20 minutes daily on days 27, 28, and 29.

For reconstitution of fB either 10 µg, 1 µg or 0.1 µg of purified fB (50 µL in PBS) was administered by intranasal application 1 hour before each airway challenge to non-sensitized and sensitized fB−/− mice. As a control PBS was administered.

In a different study 2 hours before each OVA challenge an antibody against fB (anti-fB) was administered to sensitized mice either by i.p. injection (2 mg/treatment/mouse) or by nebulization. For nebulization, 4 mice were placed in a plexiglass box, and 0.5 mg of anti-fB (in 5 ml PBS) was nebulized using an ultrasonic nebulizer (DeVilbiss Health Care). As a control, rat IgG at the same dose and volume was injected i.p. or nebulized at the same time points. On day 31, AHR was assessed and animals were sacrificed the same day for the collection of BAL fluid, blood and lung tissue.

Purification of Factor B

To reconstitute alternative pathway activity in B−/− mice, mouse complement factor B was purified from normal mouse serum by affinity purification. The affinity column was created by binding goat anti-human properdin factor B (Diasorin, Stillwater, Minn.) to CNBr-Activated Separose (Amersham, Arlington Heights, Ill.) according to the manufacturer's instructions. C57/B6J mice were bled by cardiac puncture, and the blood was collected into syringes containing 50 µl of 500 mM EDTA in order to prevent alternative pathway activation. The blood was centrifuged at 2000 rpm for 15 minutes and the plasma was collected. The plasma was then diluted 1:1 with buffer (EACA 50 mM, EDTA 10 mM, benzamidine 2 mM in PBS, pH 7.4) and passed through a 0.22 µm filter (GE Water Technologies). The plasma was added to the affinity column and the column was washed with 10 column volumes of buffer. The factor B was eluted using 5 M $LiCl_2$ and dialyzed overnight against PBS. The purity of the factor B was then checked by electrophoresis on a 10% Tris-Glycine gel and stained with Coomassie. The concentration of LPS was determined by Limulus Amebocyte Lysate Assay (BioWhittaker, Inc., Walkersville, Md.) and found to be below 1 EU/mg of purified factor B.

Generation of Anti-factor B Antibody

Anti-mouse factor B monoclonal antibodies were produced as described in Example 1. Briefly, factor B deficient mice were immunized with a recombinant fusion protein created from the second and third short consensus repeat (SCR) domains from the factor B gene and an immunoglobulin. The SCR domains were chosen because they are part of the deleted segment of the factor B gene in the fB−/− mice. fB−/− mice were then immunized with this protein and then boosted four times at three week intervals. One day after the last injection, spleen cells were fused with myeloma cells at the University of Colorado Monoclonal Antibody Center. Anti-factor B monoclonal antibody (mAb) secreting clones were then identified and characterized. One of the hybridomas, A1379, was used for these experiments. A1379 was purified from tissue culture supernatant with a Protein-G Sepharose® column (Pharacia, Uppsala, Sweden). LPS was removed from the purified mAb using polymyxin (Sigma-Aldrich, St. Louis, Mo.). The Limulus Amebocyte Lysate Assay (BioWhittaker, Inc., Walkersville, Md.) was used according to the manufacturers instructions to verify that the mAb had LPS levels below 1 EU/mg of mAb. The purity of the mAb was then checked by electrophoresis on a 10% Tris-Glycine gel and stained with Coomassie.

Determination of Airway Function

Airway responsiveness was assessed as a change in airway function after challenge with aerosolized methacholine (MCh) administered for 10 sec (60 breaths/min, 500 µl tidal volume) in increasing concentrations (6.25, 12.5, 25, 50 and 100 mg/ml). Anesthetized (pentobarbital sodium, i.p., 70 to 90 mg/kg), tracheostomized (18G cannula) mice were mechanically ventilated (160 breaths per min, tidal volume of 150 µl, positive end-expiratory pressure of 2-4 cm $H_2O$) and lung function was assessed (Takeda, 1997). Airway resistance (RL) was continuously computed (Labview, National Instruments, Tex.) by fitting flow, volume, and pressure to an equation of motion. Maximum values of RL were taken and expressed as a percentage change from baseline following PBS aerosol. There were no significant differences in baseline RL values between the respective deficient or control mice.

Bronchoalveolar Lavage and Measurement of Cytokines

After assessment of airway function, lungs were lavaged via the tracheal tube with Hank's balanced salt solution (1×1 ml, 37° C.). Number of BAL cells were obtained using a cell counter (Coulter Counter; Coulter Co., Hialeah, Fla.). Differential cell counts were made from cytocentrifuged preparations and the percentage and absolute numbers of each cell type were calculated. Cytokine levels were assessed by ELISA in BAL fluid (Tompkinson). IFN-γ, IL-4, IL-5, IL-10, IL-12 (all PharMingen, San Diego, Calif.) and IL-13 (R&D Systems, Minneapolis, Minn.) ELISAs were performed according to the manufacturers' directions.

Levels of C3a desArg in BAL fluid were measured by ELISA in non-sensitized and sensitized mice 24 hrs following the first or second allergen challenge, and at 24 and 48 hrs following the third and final challenge following the manufacturers' directions (Cedarlane Laboratories, Hornby, Ontario, Canada).

Histologic and Immunohistochemistry Studies

After obtaining BAL fluid, lungs were inflated through the trachea with 2 mL of 10% formalin and then fixed in the same solution by immersion. Tissue sections were stained with hematoxylin and eosin, periodic acid Schiff (PAS) and immunohistochemically for cells containing eosinophilic major basic protein (MBP), using a rabbit anti-mouse MBP antibody (provided by J. J. Lee, Mayo Clinic, Scottsdale, Ariz). Slides were examined in a blinded fashion and numbers of eosinophils in the peribronchial tissue and goblet cells were analyzed separately using NIH Scion Image® software (version 1.62, developed at the U.S. National Institute of Health and available on the Internet).

Measurement of Total IgE and OVA-specific Antibodies

Serum levels of total IgE, and OVA-specific IgE and IgG1 were measured by ELISA as previously described (Tompkinson). The OVA-specific antibody titers of samples were related to internal pooled standards, which were arbitrarily assigned to be 500 ELISA units (EU). The total IgE level was calculated by comparison with a known mouse IgE standard (55 3481, PharMingen).

Statistical Analysis

Analysis of variance (ANOVA) was used to determine the level of difference between all groups. Comparisons for all pairs was performed by the Tukey-Kramer honestly significant difference (HSD). Probability (p) values for significance were set at 0.05. Values for all measurements are expressed as the mean ±standard error of mean (SEM).

Results

Complement Activation Through the Alternative Pathway is Critical for the Development of AHR Following Allergen Challenge of Sensitized Mice To assess the role of the alternative pathway in the development of AHR and airway inflammation OVA-sensitized and non-sensitized fB−/− mice and matched control mice (fB+/+) were challenged with an aerosol of 1% OVA for 3 consecutive days. Sensitized and challenged fB+/+ mice showed increased responsiveness to MCh compared to challenged only fB+/+ mice (FIG. 4). In contrast, sensitized and challenged fB−/− mice demonstrated a significantly ($p<0.01$) lower response to MCh throughout the dose-response curve compared to the sensitized and challenged fB+/+ mice, and thus demonstrate a marked inability to develop AHR following sensitization and challenge.

Figure 5:
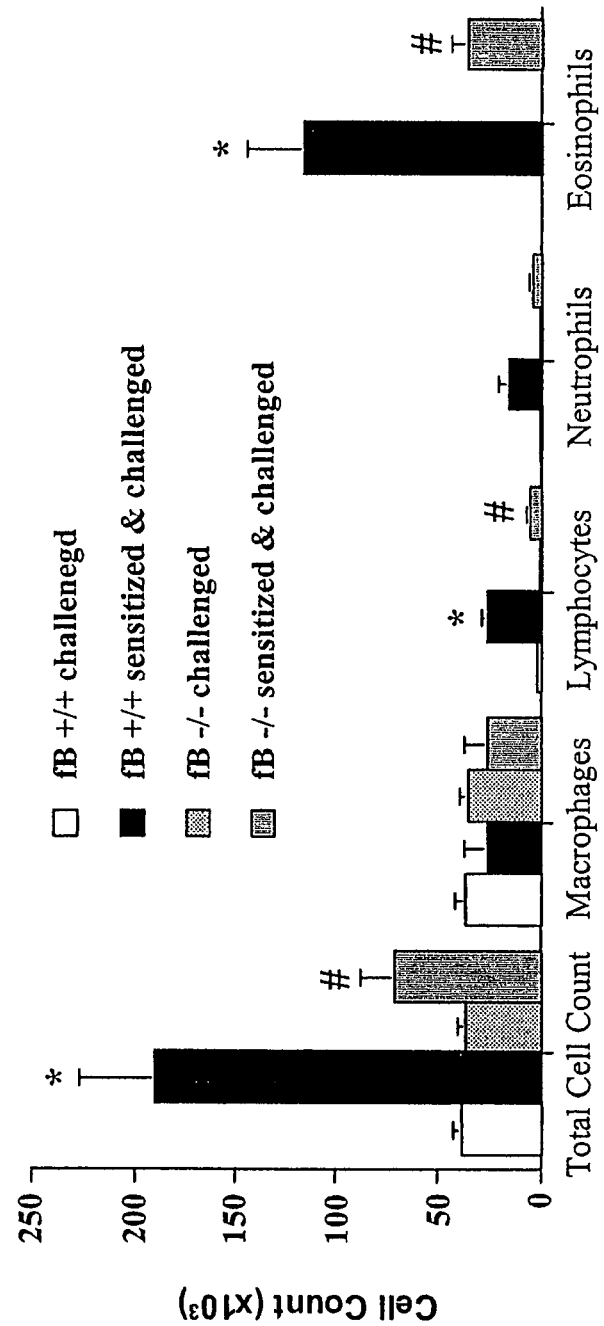
FIG. 5 is a bar graph characterizing BAL fluid and lung tissue from fB−/− mice following airway sensitization and challenge.

Complement Activation Through the Alternative Pathway is Critical for the Development Airway Inflammation Following Allergen Challenge of Sensitized Mice Airway inflammation is a characteristic feature of allergic airway disease. To assess airway inflammation BAL fluid and lung tissue was obtained 48 hrs following the last airway challenge. Sensitized and challenged fB+/+ mice showed an increase in total cell count and especially eosinophil numbers in BAL fluid compared to challenged only mice, which had no eosinophils in their BAL fluid (FIG. 5). Sensitized and challenged fB−/− mice showed significantly lower total cell count as well as numbers of eosinophils ($p<0.01$) in BAL fluid compared to sensitized and challenged fB+/+ but still significantly ($p<0.01$) higher compared to the challenged only controls. Similarly, fB−/− mice showed also lower eosinophil numbers in BAL fluid following sensitization and challenge with ragweed compared to ragweed sensitized and challenged controls (FIG. 5).

Allergen sensitization and airway challenge leads to an increase in peribronchial inflammation and especially eosinophil infiltration compared to challenged alone (FIG. 3). However, sensitized and challenged fB−/− mice showed markedly reduced peribronchial inflammation (Table 2) compared to sensitized and challenged control mice. To quantitate eosinophil infiltration in the lung, tissue section were stained with anti-major basic protein (data not shown). In challenged only mice only few eosinophils were detected in the peribronchial tissue. Sensitization and subsequent allergen challenge of fB+/+ mice resulted in significantly increased peribronchial eosinophil numbers (Table 2). In contrast, sensitized and challenged fB−/− mice showed significantly peribronchial fewer eosinophil infiltration (Table 2).

Another hallmark of allergic airway disease is goblet cell hyperplasia of the airway epithelial cells. Lungs were stained with periodic acid-Schiff to identify mucus-containing cells in the airway epithelium. In sensitized and challenge mice a large amount of cells staining positive for mucus were found (Table 2) in contrast to challenged only mice where no PAS positive cells were detectable (Table 2). Sensitized and challenged fB−/− showed significantly ($p<0.001$) less mucus containing cell in the airway epithelium compared to the sensitized and challenged wild-type mice.

Complement Activation Through the Alternative Pathway Affects Cytokine Production in BAL Fluid Th2 cytokine production by T cells plays a key role in the induction of allergic airway inflammation and AHR. To evaluate the cytokine response following allergen challenge, concentrations of IL-4, IL-5, IL-10, IL-12, IL-13 and IFN-γ were assessed in the BAL fluid, 48 h after the last OVA challenge. Sensitization and challenge of wild-type mice resulted in significant (p<0.05) increases in IL-4, IL-5 and IL-13 and significant (p<0.05) decreases in IL-10, IL-12 and IFN-γ compared to challenged only controls (data not shown). $T_H2$ cytokine levels (IL-4, IL-5 and IL-13) in the BAL fluid were decreased in the fB−/− mice (data not shown).

fB Deficiency does not Affect Serum Levels of Antigen Specific Antibodies

Serum levels of total IgE and OVA-specific IgE and IgG1 were measured 48 hours following the last airway challenge. Sensitized and challenge fB+/+ mice showed increased levels of total IgE and OVA-specific IgE and IgG1 compared to challenged only control mice (Table 3). Similarly, fB−/− mice showed increased levels of total IgE and OVA-specific IgE and IgG1, which were not statistically different from sensitized and challenged fB+/+ mice, indicating that the humoral response to allergen sensitization and challenge remains intact in these mice.

complement component 4 (C4−/−), which is essential to the activation of the classical and lectin pathways, in comparison to the fB−/− mice.

To assess activation of the complement pathway, levels of C3a desArg were assessed in BAL fluid. Challenged only mice showed low levels of C3a desArg (data not shown). In contrast, sensitized mice showed increased levels of C3a desArg in BAL fluid after the first, second and third challenge, with the highest values at 48 hrs following the last challenge (data not shown). Interestingly, sensitized and challenged C4−/− mice showed similar levels of C3a compared to the sensitized and challenged wild-type mice, in contrast to sensitized and challenged fB−/− mice, which showed a decrease in C3a desArg levels compared to their respective sensitized and challenged wild-type mice (data not shown). These data suggest that following allergen exposure of sensitized mice, complement activation occurs through the alternative pathway.

Figure 9:
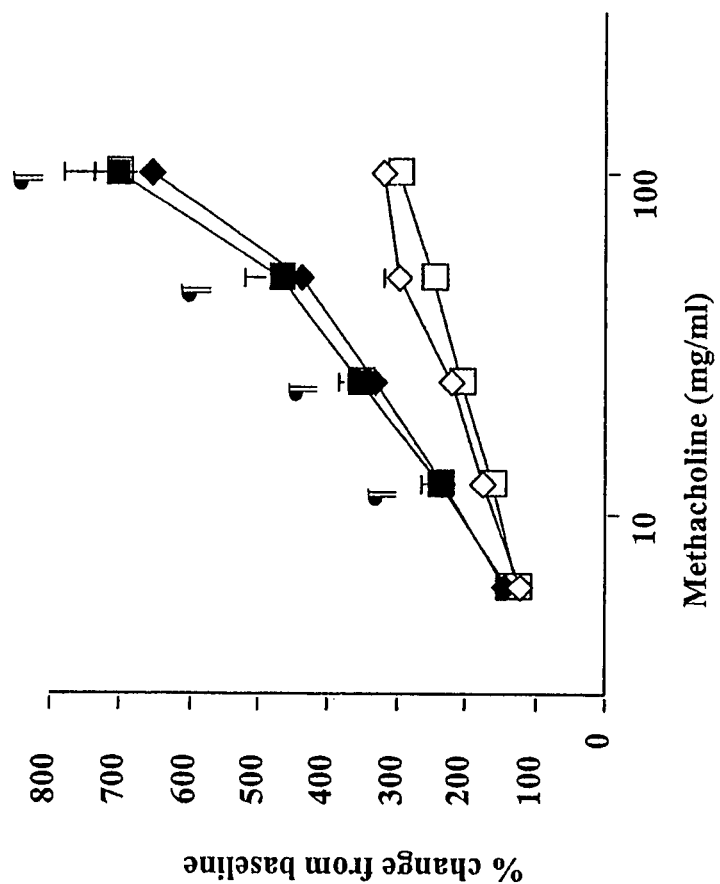
FIG. 9 is a line graph showing that sensitized and challenged C4−/− (closed diamond, n=10) showed a similar response to inhaled MCh as sensitized and challenged C4+/+ mice (closed square, n=10) and significantly higher responses compared to challenged only C4−/− (open diamond, n=10) and challenged only C4+/+ mice (open square, n=10) (*$p<0.05$ compared to fB−/− sensitized and challenged fB+/+ challenged and fB−/− challenged; # $p<0.05$ compared to fB+/+challenged and fB−/− challenged; ¶$p<0.05$ compared to C4+/+challenged and C4−/− challenged).

C4−/− mice (developed similar levels of AHR as the sensitized and challenged C4+/+mice (FIG. 9). Similarly, C4−/− mice showed no decrease in total cell counts (mean ±SEM, n=10; 163±35×$10^3$ cells), or lymphocyte (28±9×$10^3$ cells) and eosinophil (98±23×$10^3$ cells) numbers in bronchoalveolar lavage (BAL) fluid compared to the sensitized and challenged control mice (n=10; 175±53; 35±12; 115±32×$10^3$

TABLE 2

Quantification of goblet cell hyperplasia and peribronchial eosinophil inflammation

| | fβ +/+ Challenged only | fβ +/+ Sensitized & Challenged | fβ −/− Sensitized & Challenged | C4 +/+ Sensitized & Challenged | C4 −/− Sensitized & Challenged | Control Ab Sensitized & Challenged | anti-fβ i.p. Sensitized & Challenged | anti-fβ neb Sensitized & Challenged |
|---|---|---|---|---|---|---|---|---|
| PAS-positive cells (cells/mm BM) | N.D. | 132 ± 35 * | 36 ± 19 # | 156 ± 27 * | 149 ± 15 * | 153 ± 33 * | 28 ± 10 # | 43 ± 12 # |
| αMBP-positive cells (cells/mm BM) | 1.3 ± 0.9 | 80 ± 16 * | 24 ± 14 # | 95 ± 20 * | 87 ± 21 * | 95 ± 28 * | 20 ± 9 # | 33 ± 16 # |

Mice were sensitized and challenged as described in Methods. Number of goblet cells (PAS-positive cells) and peribronchial eosinophils (anti-major basic protein (MBP)-positive cells) were assessed 48 h after the last challenge. Mean values ± SEM are shown; fβ −/−: factor B deficient mice; fβ +/+:congenic wild-type control mice; C4 −/−: complement factor 4 deficient mice; C4 +/+: congenic wild-type control mice; Control Ab: C57BL/6 mice sensitized and challenged treated with control Ab i.p.; anti-fβ i.p.: C57BL/6 mice sensitized and challenged treated with anti-fβ antibody i.p.; anti-fβ neb: C57BL/6 mice sensitized and challenged treated with anti-fβ antibody by inhalation; BM (basement membrane).
* p < 0.05 compared to fβ +/+ challenged only, fβ −/− challenged; anti-fβ i.p. sensitized & challenged and anti-fβ neb sensitized & challenged.
# p < 0.05 compared to fβ +/+ challenged only.

TABLE 3

Serum immunoglobulin levels

| | fβ +/+ Challenged only | fβ +/+ Sensitized & Challenged | fβ −/− Challenged only | fβ −/− Sensitized & Challenged | C57BL/6 Sensitized & Challenged | Control Ab Sensitized & Challenged | anti-fβ i.p. Sensitized & Challenged | anti-fβ neb Sensitized & Challenged |
|---|---|---|---|---|---|---|---|---|
| Total IgE (ng/ml) | 47.3 ± 11.2 | 219.8 ± 48.4 * | 38.5 ± 12.5 | 198.3 ± 31.2 * | 241.1 ± 37.6 * | 238.5 ± 41.1 * | 189.6 ± 33.2 * | 229.5 ± 44 * |
| OVA-specific IgE (EU/ml) | <10 | 145.1 ± 36.7 * | <10 | 166.2 ± 42.1 * | 153.8 ± 47.4 * | 128.1 ± 30.8 * | 99.1 ± 27.4 * | 122.5 ± 39.5 * |
| OVA-specific IgG1 (EU/ml) | <10 | 189.1 ± 20.5 * | <10 | 155.9 ± 38.8 * | 171.8 ± 71.1 * | 146.5 ± 61.2 * | 106.5 ± 28.9 * | 120.1 ± 30.8 * |

Mice were sensitized and challenged as described in Methods. Serum levels of immunoglobulins were assessed 48 h after the last challenge. Mean values ± SEM are shown; fβ −/−: factor B deficient mice; fβ +/+: congenic wild-type control mice; C57BL/6 mice sensitized and challenged treated with control Ab i.p.; anti-fβ i.p.:C57BL/6 mice sensitized and challenged treated with anti-fβ antibody i.p.; anti-fβ neb: C57BL/6 mice sensitized and challenged treated with anti-fβ antibody by inhalation; EU/ml (Elisa Units/ml).
* p < 0.05 compared to fβ +/+ challenged only and fβ −/− challenged.

Activation of the Classical Pathway in this Model is not Essential to the Development of Allergic Airway Disease To further define the complement pathway critical to the development of allergic responses in the lungs of sensitized and challenged mice, the inventors used mice deficient in cells, respectively) (data not shown). Further sensitized and challenged C4−/− mice showed similar increases in peribronchial eosinophil numbers and numbers of goblet cells compared to the sensitized and challenged respective WT mice (Table 2). These findings suggest that activation of the classical pathway in this model is not essential to the development of allergic airway disease.

Lack of Development on AHR and Airway Inflammation in fB Deficient Mice is not Specific for OVA To assess if the lack of airway hyperresponsiveness following allergen sensitization and challenge was due to a specific unresponsiveness to OVA, fB−/− and wild-type mice were sensitized and challenged with ragweed. Ragweed sensitized and challenged fB−/− mice showed a decrease in responsiveness to MCh, whereas fB+/+developed a strong response to MCh (FIGS. 6A and 6B). Similarly, airway inflammation in BAL fluid was reduced in ragweed sensitized and challenged fB−/− mice compared to fB+/+(FIG. 6C).

Figure 7A:
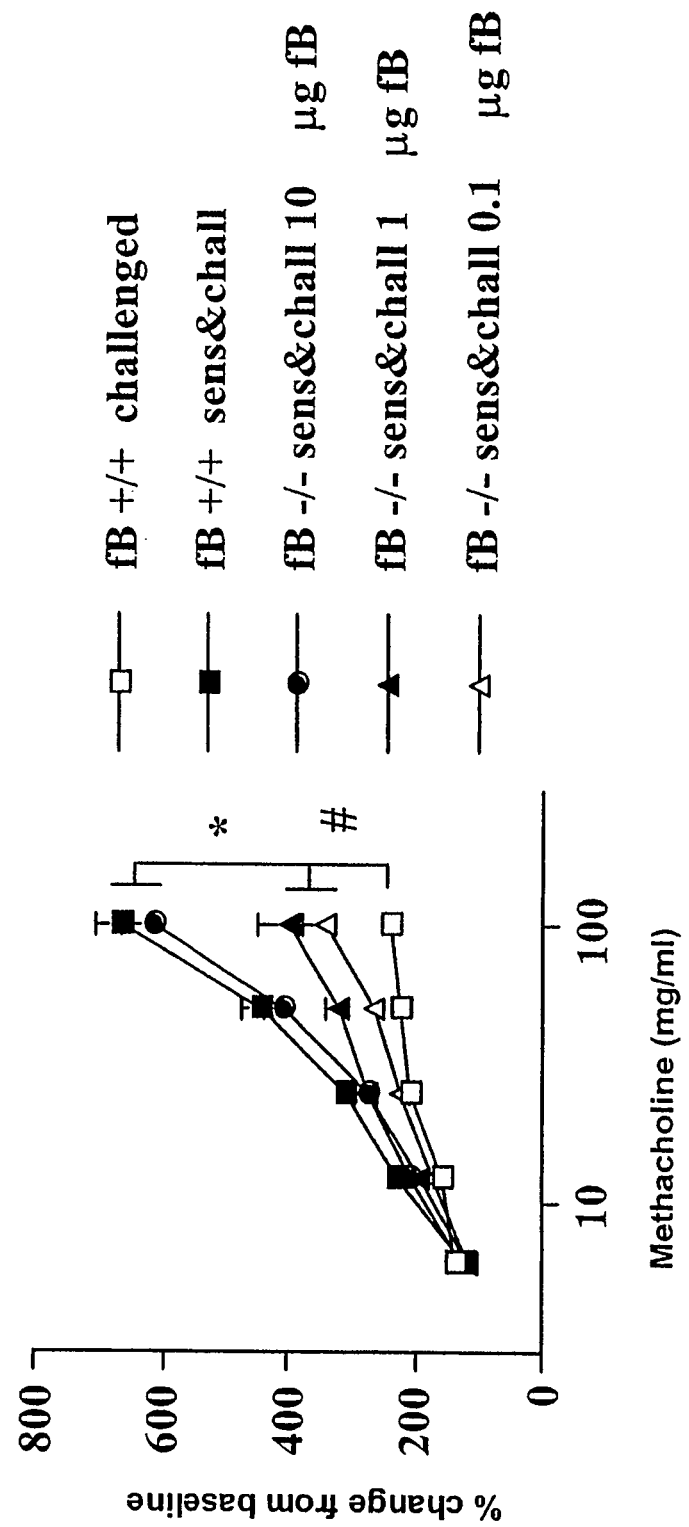
FIG. 7A is a line graph showing that sensitized and challenged fB−/− mice treated with factor B before each challenge showed a decreased response to methacholine similar to sensitized and challenged fB−/− mice treated with PBS, but significantly lower compared to sensitized and challenged fB+/+ mice.

Administration of Factor B Reconstitutes the Ability to Develop AHR and Airway Inflammation in fB−/− Mice To reconstitute factor B in the lung fB−/− received a single intranasal application of either 10 µg, 1 µg, 0.1 µg of purified factor B (FIG. 7) or a PBS before each airway challenge. Sensitized and challenged fB−/− mice treated with 0.1 µg of factor B before each challenge showed a decreased response to MCh similar to sensitized and challenged fB−/− mice treated with PBS, but significantly lower compared to sensitized and challenged fB+/+ mice (FIG. 7A). Sensitized and challenged mice treated with 1 µg of purified factor B showed a slight but not statistically different increase in airway reactivity compared to sensitized and challenged fB−/− mice either treated with PBS or 0.1 µg of purified factor B (FIG. 7A). In contrast, sensitized and challenged fB−/− mice treated with 10 µg of purified factor B before each airway challenge showed an increased response to MCh, similar to the sensitized and challenged fB+/+ mice.

Also treatment of sensitized and challenged fB−/− mice with 10 µg of purified factor B before each airway challenge increased airway inflammation and especially eosinophil numbers in BAL fluid similar to numbers observed in sensitized and challenged fB+/+ mice, whereas treatment with either 0.1 µg or 1 µg purified factor B failed to increase numbers of eosinophils in the BAL fluid (FIG. 7B). If factor B was given before each airway challenge but to non-sensitized recipients, AHR or airway inflammatory responses were not observed, indicating that the sensitization phase was needed for the responses to develop on challenge, as well as demonstrating that the sensitization phase in the fB−/− mice was intact. These data in the fB−/− mice directly demonstrate that factor B of the alternative pathway is critical to the development of allergic airway disease.

Figure 8C:
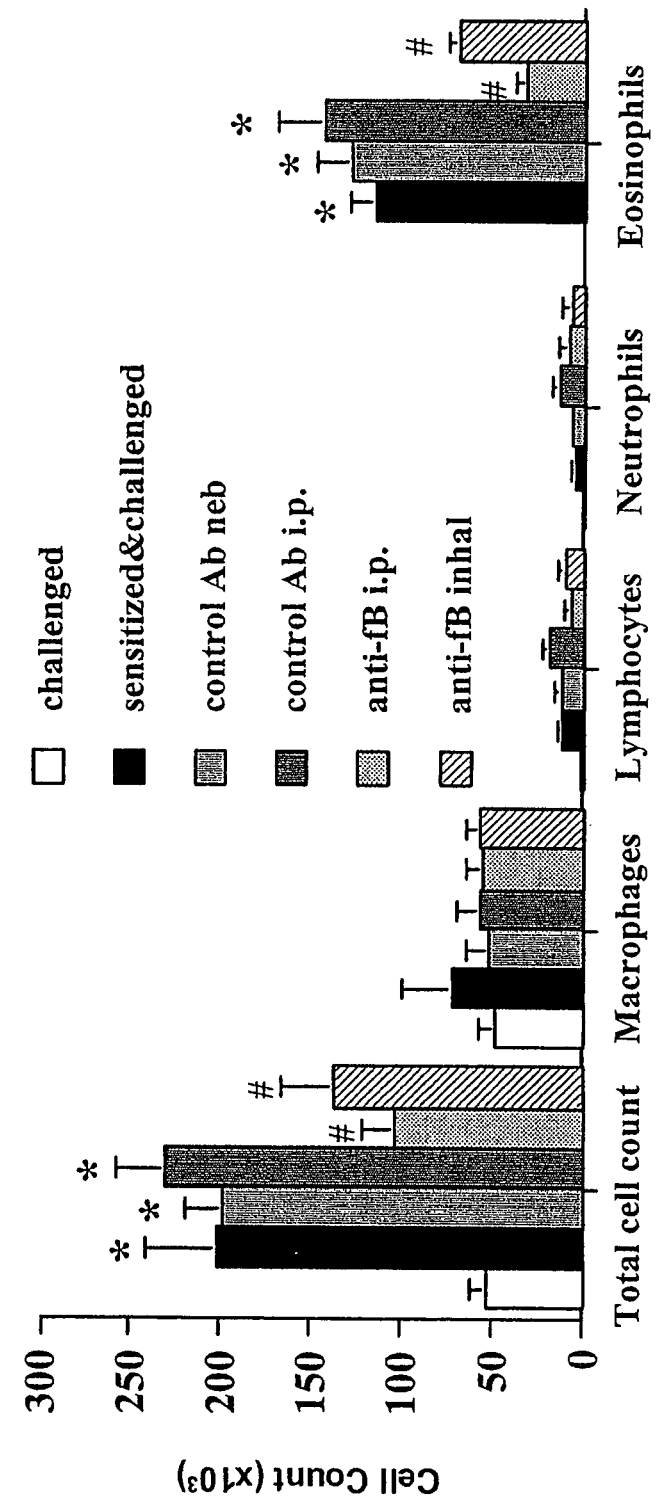
FIG. 8C is a bar graph characterizing BAL fluid and lung tissue and showing that treatment with either systemic or nebulized anti-factor B reduced the number of eosinophils in the BAL fluid, peribronchial inflammation, peribronchial eosinophil numbers, as well as number of mucus positive cells in the airway epithelium.
Figure 10:
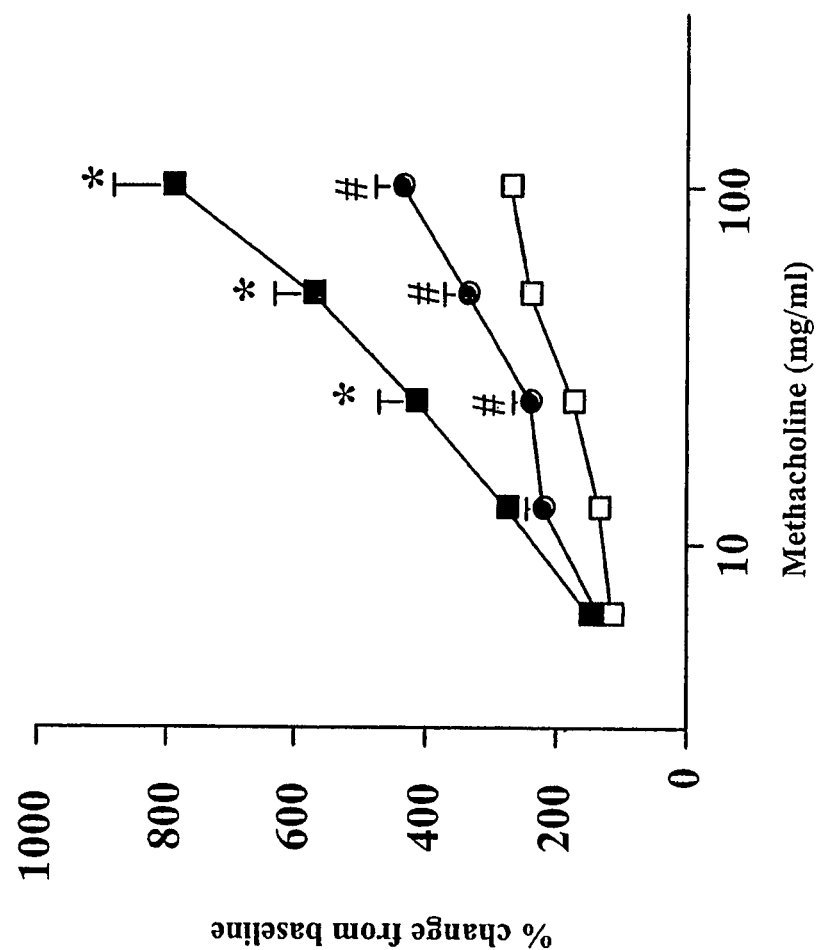
FIG. 10 is a line graph showing that sensitized and challenged C4−/− mice (solid box, n=8) showed increased airway resistance to inhaled MCh compared to challenged only C4−/− mice (open box, n=8), and that treatment of sensitized and challenged C4−/− mice with systemic anti-factor B monoclonal antibody decreased the airway response to MCh (solid circle, n=8).

Treatment with a fB Neutralizing Antibody Inhibits the Development of AHR in Sensitized and Challenged Mice To assess the role of complement activation through the alternative pathway in sensitized and challenge non-gene-deficient mice, C57BL/6 were sensitized as described in Methods. The 1379 anti-factor B antibody described in Example 1 was administered either systemically or locally by nebulization, which has been shown to be an effective route for administration of other complement inhibitors. Normal mice, treated after sensitization but during the challenge phase with either systemic or local (nebulized) anti-factor B, showed a significant decrease in AHR (FIGS. 8A and 8B), as well as an inhibition of airway inflammation and eosinophilia in the airways (FIG. 8C). Furthermore, tissue inflammation, peribronchial eosinophil numbers (Table 2) as well as the number of goblet cell (Table 2) were reduced in these anti-fB-treated mice. Additionally, levels of IL-4, IL-5 and IL-13 were significantly lower in BAL fluid of mice treated with the fB antibody (data not shown). Similarly, treatment of sensitized and challenged C4−/− mice with anti-factor B decreased their airway responsiveness and airway inflammation (FIG. 10). These data are in accord with studies using complement inhibitors which do not discriminate between the classical and alternative pathways but block the development of a late airway response as well as AHR.

REFERENCES

1. Busse et al., 2001, *N Engl J Med* 344:350-62
2. Lee et al., 2001, *J Allergy Clin Immunol* 107:945-57
3. Henson P., 2000, *Nat Immunol* 1: 190-2
4. Humbles et al., 2000, *Nature* 406:998-1001
5. Krug et al., 2001, *Am J Respir Crit. Care Med* 164:1841-3
6. Drouin et al., 2001, *J Immunol* 166:2025-32
7. Karp et al., 2000, *Nat Immunol* 1:221-6
8. Drouin et al., 2002, *J Immunol* 169:5926-5933
9. Bautsch et al., 2000, *J Immunol* 165:5401-5
10. Walters et al., 2002, *Am J Respir Cell Mol Biol* 27:413-8
11. Kalli et al., 1994, *Springer Semin Immunopathol* 15:417-31
12. Weisman et al., 1990, *Science* 249:146-51
13. Wong and Fearon, 1985, *J Immunol* 134:4048-56
14. Li et al., 1993, *J Immunol* 151:4295-305
15. Kim et al., 1995, *J Exp Med* 181:151-9
16. Quigg et al., 1998, *J Immunol* 160:4553-60
17. Holers et al., 2002, *J Exp Med* 195:211-20
18. Rehrig et al., 2001, *J Immunol* 167:5921-7
19. Rah et al., 2003, *J Allergy Clin Immunol* 111:A916
20. Takeda et al., 1997, *J Exp Med* 186:449-54
21. Tomkinson et al., 2001, *Am J Respir Crit. Care Med* 163:721-30
22. Taube et al., 2002, *J Immunol* 169:6482-9
23. Oshiba et al., 1996, *J Clin Invest* 97:1398-408
24. Oshiba et al., 1997, *J Immunol* 159:4056-63
25. Hamelmann et al., 1999, *Am J Respir Cell Mol Biol* 21:480-9
26. Kohl, 2001, *Mol Immunol* 38:175-87
27. Schwartz et al., 1983, *J Immunol* 130:1891-5
28. Mulligan et al., 1996, *J Clin Invest* 98:503-12
29. Czermak et al., 1999, *Nat Med* 5:788-92
30. Holers, 2000, *Immunopharmacology* 49:125-31
31. Drouin et al., 2001, *J Immunol* 167:4141-5
32. Carroll, 1998, *Annu. Rev. Immunol.* 16:545-68
33. Fischer et al., 1996, *J Immunol* 157:549-56
34. Wittmann et al., 1999, *J Immunol* 162:6763-9
35. Braun et al., 2000, *J Immunol* 164:3009-17
36. Abe et al., 2001, *J Immunol* 167:4651-60
37. Hamelmann et al., 1999, *Am J Respir Crit. Care Med* 160:934-41
38. Hamelmann et al., 1997, *Am J Respir Crit. Care Med* 155:819-25
39. Corry et al., 1996, *J Exp Med* 183:109-17
40. Wills-Karp et al., 1998, *Science* 282:2258-61
41. Grunig et al., 1998, *Science* 282:2261-3
42. Kopf et al., 2002, *Nat Med* 8:373-8
43. Werfel et al., 2000, *J Immunol* 165:6599-605
44. La Flamme et al., 2003, *J Immunol* 170:470-476
45. Takafuji et al., 1996, *Allergy* 51:563-8
46. DiScipio et al., 1999, *J Immunol* 162:1127-36
47. Elsner et al., 1994, *Blood* 83:3324-31
48. Elsner et al., 1994, *Eur J Immunol* 24:518-22

Example 3

The following example describes additional binding data for a panel of anti-factor B antibodies produced by the present inventors. Assays were used to test the binding and/or inhibition of mouse factor B and human factor B for the various antibodies. As can be seen, the mAb 1379 both binds and inhibits mouse and human factor B. In contrast, the mAb designated 624 can bind both mouse and human factor B, but does not inhibit the human alternative pathway. A competition ELISA was used to further evaluate the antibodies. As can be seen, the antibodies 624, 691, and 1231 do not block binding by 1379. These antibodies must therefore bind the protein at a different site, explaining why they bind factor B without inhibiting its function in vitro. However, antibodies 395, 1322 and 1060 are competitive inhibitors of 1379.

TABLE 4

| Clone | Isotype | Binds mouse fB | Binds human fB | Inhibits mouse alternative pathway (zymosan assay) | Inhibits human alternative pathway (rabbit erythrocyte lysis assay) | Competes with 1379 for human fB binding |
|---|---|---|---|---|---|---|
| 1379 | IgG1 κ | +++ | +++ | +++ | +++ | +++ |
| 395 | IgG1 κ | +++ | ++ | ++ | +++ | +++ |
| 1322 | IgG2b κ | +++ | +++ | + | ++ | +++ |
| 624 | IgG1 κ | +++ | +++ | + | − | − |
| 691 | IgG1 κ | +++ | +++ | + | − | − |
| 1060 | IgG2b κ | +++ | +++ | + | ++ | ++ |
| 1231 | IgG1 | +++ | +++ | + | − | − |
| E1128 | | − | +++ | − | 0 | NA |

Example 4

The following example describes the epitope mapping for mAb1379 on the human factor B surface.

Initial experiments to map the epitope for the mAb1379 antibody indicated that the epitope or antibody binding site on factor B was not linear. The antibody avidly bound the full length protein when it was adhered to an ELISA plate. Peptides that were 10 amino acids in length were constructed to span the region of the protein where binding is known to occur (SCR2-3). When these peptides were adhered to an ELISA plate, the antibody did not recognize them, indicating that none of these linear sequences was recognized as the epitope.

The predicted conserved binding surface or epitope of the human factor B that is recognized by mAb1379 was modeled. Briefly, the tertiary structure of human factor B was built based on the resolved three-dimensional structure of CR2-SCR1-2 (Protein Data Bank (PDB) id 1GHQ). The final model was refined to the minimal energy state, with the constrains fixed on the four absolutely conserved Cys residues of each SCR. The sequence identity of factor B SCR2-3 with CR2SCR1-2 is 30% (highest), with factor H SCR15-16 25%, with CD46 20%. FIG. 11 shows the model of the factor B structure with the amino acid positions corresponding to the mAb1379 epitope (relative to SEQ ID NO:2) indicated. The residues that are believed to form the conformational epitope for the mAb1379 antibody are: Ala137, Tyr139, Ser141, Glu182, Ser185, Thr189, Glu190, and Ser192, although the epitope may contain only a few, substantially all, or more residues than is depicted in FIG. 11.

This model can now be used to predict the effects of the previously discussed factor B mutants from Hourcade (Hourcade, 1995, *J. Biol. Chem.*) that were initially used to characterize the epitope for the mAb1379 antibody (see Example 1). Shown below are four mutants from this panel that are contain residues belonging to the mAb1379 epitope model as shown in FIG. 11. As shown below, the B17 and B23 mutants, which were shown in Example 1 to reduce the binding of mAb1379 have particularly substitutions (indicated in bold and italics) that are predicted to face inward and therefore may be disturbing the structure of the epitope or conserved binding surface for mAb1379. Mutant B16/17, although containing residues that are within the modeled epitope for mAb1379, is not predicted to have mutations that would disturb the structure of the epitope, which can explain why this mutant bound to the antibody in the initial mapping experiments. Similarly, although mutant B23/24 also contains residues that are within the modeled epitope for mAb1379, this mutant also bound to the antibody in the initial mapping experiments, the residues forming the antibody contact sites are likely not disturbed by the mutations. This experiment also illustrates that the antibody of the invention may bind to factor B proteins, or portions thereof, having conservative mutations or mutations that do not substantially disrupt this epitope.

```
B17:      Y139-C140-S141
Subs:      H         P

B23:      E182-G183-G184-S185
Subs:      G    N         V

B16/17:   G136-A137-G138
Subs:      N    S    S

B23/24:   S187-G188-T189-E190-P191-S192
Subs:      D         E    T    A    V
```

FIG. 12 is a schematic drawing showing a modeled complex of mAB1379 (one Fab fragment) binding to factor B, with the antigen binding sides of the Fab having been modeled to cover the entire mapped epitope region as defined above in FIG. 11.

Example 5

The following example demonstrates that inhibition of the alternative complement pathway, and specifically, inhibition of factor B, inhibits and protects animals from injury in renal ischemia-reperfusion.

Experiments have been conducted to test the efficacy of the mAb 1379 at ameliorating injury in the model of ischemic acute renal failure. In this model, ischemic acute renal failure is induced by anesthetizing the mice and clamping the renal pedicles for 24 minutes. Mice were injected intraperitoneally with 1 mg of the mAb an hour prior to the induction of injury. This protocol causes a reversible form of ischemic acute renal failure, with the peak injury typically occurring 24 hours after the clamps are removed from the renal pedicles and blood flow is restored to the kidney. The renal injury is then assessed by measuring the accumulation of nitrogenous wastes such as SUN and serum creatinine and assessment of the morphologic injury of the kidneys by a renal pathologist. The inventors have demonstrated that the alternative pathway of complement is activated soon after reperfusion of the kidneys, and that this activation contributes to the resultant renal injury.

Examination of the kidneys by immunofluorescence and Western blot analysis confirmed that the 1379 antibody described herein effectively prevented complement activation after I/R. As shown in FIG. 13, mice that were pre-treated with 1379 demonstrated milder increases in serum urea nitrogen (SUN) after 24 hours of reperfusion when compared to wild-type controls (78±15 mg/dL vs. 119±15 mg/dL, P<0.05, n=11 for each group). Histologic injury was also milder in mice that were treated with 1379. When graded by a pathologist in a blinded fashion, the 1379 treated mice demonstrated significantly less tubular damage than control mice (3.3±0.5 vs. 4.9±0.1, p<0.01, n=10 for each group). Thus, 1379 effectively prevents complement activation in the mouse kidney after I/R, and pre-treatment with 1379 ameliorates the functional and histologic injury after I/R.

In another experiment, renal tubular epithelial cells in culture were subjected to two hours of chemical anoxia by incubating them with antimycin. The cells were then exposed to fresh mouse serum (as a source of complement), and lactate dehydrogenase (LDH) was measured as a marker of cell death, and expressed in arbitrary units utilizing a commercial assay (Promega, Madison, Wis.). Cells that were exposed to antimycin and serum released significantly greater LDH then cells exposed to serum alone (100,140±3307 for antimycin+serum vs. 69,255±9754, p<0.05; data not shown). When the serum was incubated with the mAb 1379 prior to incubation with cells, however, the LDH release fell to 76,471±7720 (p<0.01 vs. cells treated with antimycin+serum; data not shown). The mAb 1379 thus protects hypoxic renal tubular epithelial cells that are exposed to components of the alternative pathway either in vivo or in vitro.

Each of the references cited herein is incorporated by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

The invention claimed is:

1. A fusion protein comprising:
   a) an antibody or antigen-binding fragment thereof that selectively binds to factor B, wherein the antibody or antigen-binding fragment thereof prevents formation of a C3bBb complex, and wherein the antibody or antigen binding fragment thereof selectively binds to factor B at the same epitope as the anti-factor B monoclonal antibody 1379 (produced by ATCC Deposit No. PTA-6230); and
   b) a targeting moiety comprising a CR2 protein comprising at least the short consensus repeat 1 (SCR1) and short consensus repeat 2 (SCR2) domains, C3, C3d, C3dg, iC3b, C3b, or an antibody that selectively binds to the CR2 protein, C3, C3d, C3dg, iC3b, or C3b.

2. The fusion protein of claim 1, wherein the antibody or antigen-binding fragment thereof selectively binds to factor B from multiple mammalian species.

3. The fusion protein of claim 2, wherein the antibody or antigen-binding fragment thereof selectively binds to factor B from human and an animal selected from the group consisting of non-human primates, mouse, rat, pig, horse, and rabbit.

4. The fusion protein of claim 1, wherein the antigen-binding fragment is an Fab.

5. The fusion protein of claim 1, wherein the antibody or antigen-binding fragment thereof is a humanized antibody or antigen-binding fragment thereof against factor B.

6. The fusion protein of claim 1, wherein the targeting moiety comprises CR2.

7. A method of specifically inhibiting activation of the alternative complement pathway in an animal, comprising administering to the animal a fusion protein according to claim 1.

8. The method of claim 7, wherein the animal is a mammal.

9. The method of claim 8, wherein the animal is a human.

10. A method of reducing or preventing airway hyperresponsiveness (AHR) or airway inflammation in an animal, comprising administering a fusion protein according to claim 1 to an animal that has, or is at risk of developing, airway hyperresponsiveness associated with inflammation or airway inflammation.

11. The method of claim 10, wherein the animal is a mammal.

12. The method of claim 11, wherein the animal is a human.

13. The method of claim 12, wherein the animal has rhinitis.

14. The method of claim 12, wherein the animal has sinusitis.

15. The fusion protein of claim 1, wherein the antibody that selectively binds to factor B is of a non-complement activating isotype or subclass.

16. The fusion protein of claim 1, wherein the antibody that selectively binds to factor B is a monoclonal antibody.

17. The fusion protein of claim 1, wherein the antibody that selectively binds to factor B is a bispecific antibody.

18. The fusion protein of claim 1, wherein the antibody that selectively binds to factor B is a monovalent antibody.

19. The fusion protein of claim 1, wherein the antibody that selectively binds to factor B is the monoclonal antibody 1379 (produced by ATCC deposit No. PTA-6230).

20. The fusion protein of claim 1, wherein the antibody that selectively binds to factor B is a chimeric antibody.

21. The fusion protein of claim 1, wherein the targeting moiety comprises the CR2 protein comprising at least the SCR1 and SCR2 domains.

22. The fusion protein of claim 1, wherein the targeting moiety comprises C3.

23. The fusion protein of claim 1, wherein the targeting moiety comprises C3d.

24. The fusion protein of claim 1, wherein the targeting moiety comprises C3dg.

25. The fusion protein of claim 1, wherein the targeting moiety comprises iC3b.

26. The fusion protein of claim 1, wherein the targeting moiety comprises C3b.

27. The fusion protein of claim 1, wherein the targeting moiety comprises an antibody that selectively binds to the CR2 protein, C3, C3d, C3dg, iC3b, or C3b.

* * * * *

UNITED STATES PATENT AND TRADEMARK OFFICE
CERTIFICATE OF CORRECTION

| | | |
|---|---|---|
| PATENT NO. | : 8,652,475 B2 | Page 1 of 1 |
| APPLICATION NO. | : 11/888997 | |
| DATED | : February 18, 2014 | |
| INVENTOR(S) | : Holers et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 928 days.

Signed and Sealed this
Twenty-first Day of July, 2015

Michelle K. Lee
*Director of the United States Patent and Trademark Office*

SEQUENCE LISTING

<160> NUMBER OF SEQ ID NOS: 6

<210> SEQ ID NO 1
<211> LENGTH: 764
<212> TYPE: PRT
<213> ORGANISM: Homo sapiens

<400> SEQUENCE: 1

```
Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
            85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
            115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220
```

-continued

```
Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
            245                 250                 255

Gln Lys Arg Lys Ile Val Leu Asp Pro Ser Gly Ser Met Asn Ile Tyr
        260                 265                 270

Leu Val Leu Asp Gly Ser Asp Ser Ile Gly Ala Ser Asn Phe Thr Gly
    275                 280                 285

Ala Lys Lys Cys Leu Val Asn Leu Ile Glu Lys Val Ala Ser Tyr Gly
290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
    370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
        435                 440                 445

Glu Gln His Val Phe Lys Val Lys Asp Met Glu Asn Leu Glu Asp Val
    450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
    530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
    610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655
```

```
Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
        675                 680                 685

Tyr Ala Asp Pro Asn Thr Cys Arg Gly Asp Ser Gly Gly Pro Leu Ile
    690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu
        755                 760

<210> SEQ ID NO 2
<211> LENGTH: 739
<212> TYPE: PRT
<213> ORGANISM: Homo sapiens

<400> SEQUENCE: 2

Thr Pro Trp Ser Leu Ala Arg Pro Gln Gly Ser Cys Ser Leu Glu Gly
1               5                   10                  15

Val Glu Ile Lys Gly Gly Ser Phe Arg Leu Leu Gln Glu Gly Gln Ala
            20                  25                  30

Leu Glu Tyr Val Cys Pro Ser Gly Phe Tyr Pro Tyr Pro Val Gln Thr
        35                  40                  45

Arg Thr Cys Arg Ser Thr Gly Ser Trp Ser Thr Leu Lys Thr Gln Asp
    50                  55                  60

Gln Lys Thr Val Arg Lys Ala Glu Cys Arg Ala Ile His Cys Pro Arg
65                  70                  75                  80

Pro His Asp Phe Glu Asn Gly Glu Tyr Trp Pro Arg Ser Pro Tyr Tyr
                85                  90                  95

Asn Val Ser Asp Glu Ile Ser Phe His Cys Tyr Asp Gly Tyr Thr Leu
            100                 105                 110

Arg Gly Ser Ala Asn Arg Thr Cys Gln Val Asn Gly Arg Trp Ser Gly
        115                 120                 125

Gln Thr Ala Ile Cys Asp Asn Gly Ala Gly Tyr Cys Ser Asn Pro Gly
    130                 135                 140

Ile Pro Ile Gly Thr Arg Lys Val Gly Ser Gln Tyr Arg Leu Glu Asp
145                 150                 155                 160

Ser Val Thr Tyr His Cys Ser Arg Gly Leu Thr Leu Arg Gly Ser Gln
                165                 170                 175

Arg Arg Thr Cys Gln Glu Gly Gly Ser Trp Ser Gly Thr Glu Pro Ser
            180                 185                 190

Cys Gln Asp Ser Phe Met Tyr Asp Thr Pro Gln Glu Val Ala Glu Ala
        195                 200                 205

Phe Leu Ser Ser Leu Thr Glu Thr Ile Glu Gly Val Asp Ala Glu Asp
    210                 215                 220

Gly His Gly Pro Gly Glu Gln Gln Lys Arg Lys Ile Val Leu Asp Pro
225                 230                 235                 240

Ser Gly Ser Met Asn Ile Tyr Leu Val Leu Asp Gly Ser Asp Ser Ile
                245                 250                 255

Gly Ala Ser Asn Phe Thr Gly Ala Lys Lys Cys Leu Val Asn Leu Ile
            260                 265                 270
```

```
Glu Lys Val Ala Ser Tyr Gly Val Lys Pro Arg Tyr Gly Leu Val Thr
            275                 280                 285

Tyr Ala Thr Tyr Pro Lys Ile Trp Val Lys Val Ser Glu Ala Asp Ser
        290                 295                 300

Ser Asn Ala Asp Trp Val Thr Lys Gln Leu Asn Glu Ile Asn Tyr Glu
305                 310                 315                 320

Asp His Lys Leu Lys Ser Gly Thr Asn Thr Lys Lys Ala Leu Gln Ala
                325                 330                 335

Val Tyr Ser Met Met Ser Trp Pro Asp Asp Val Pro Pro Glu Gly Trp
            340                 345                 350

Asn Arg Thr Arg His Val Ile Ile Leu Met Thr Asp Gly Leu His Asn
        355                 360                 365

Met Gly Gly Asp Pro Ile Thr Val Ile Asp Glu Ile Arg Asp Leu Leu
    370                 375                 380

Tyr Ile Gly Lys Asp Arg Lys Asn Pro Arg Glu Asp Tyr Leu Asp Val
385                 390                 395                 400

Tyr Val Phe Gly Val Gly Pro Leu Val Asn Gln Val Asn Ile Asn Ala
                405                 410                 415

Leu Ala Ser Lys Lys Asp Asn Glu Gln His Val Phe Lys Val Lys Asp
            420                 425                 430

Met Glu Asn Leu Glu Asp Val Phe Tyr Gln Met Ile Asp Glu Ser Gln
        435                 440                 445

Ser Leu Ser Leu Cys Gly Met Val Trp Glu His Arg Lys Gly Thr Asp
    450                 455                 460

Tyr His Lys Gln Pro Trp Gln Ala Lys Ile Ser Val Ile Arg Pro Ser
465                 470                 475                 480

Lys Gly His Glu Ser Cys Met Gly Ala Val Val Ser Glu Tyr Phe Val
                485                 490                 495

Leu Thr Ala Ala His Cys Phe Thr Val Asp Asp Lys Glu His Ser Ile
            500                 505                 510

Lys Val Ser Val Gly Gly Glu Lys Arg Asp Leu Glu Ile Glu Val Val
        515                 520                 525

Leu Phe His Pro Asn Tyr Asn Ile Asn Gly Lys Lys Glu Ala Gly Ile
    530                 535                 540

Pro Glu Phe Tyr Asp Tyr Asp Val Ala Leu Ile Lys Leu Lys Asn Lys
545                 550                 555                 560

Leu Lys Tyr Gly Gln Thr Ile Arg Pro Ile Cys Leu Pro Cys Thr Glu
                565                 570                 575

Gly Thr Thr Arg Ala Leu Arg Leu Pro Pro Thr Thr Thr Cys Gln Gln
            580                 585                 590

Gln Lys Glu Glu Leu Leu Pro Ala Gln Asp Ile Lys Ala Leu Phe Val
        595                 600                 605

Ser Glu Glu Glu Lys Lys Leu Thr Arg Lys Glu Val Tyr Ile Lys Asn
    610                 615                 620

Gly Asp Lys Lys Gly Ser Cys Glu Arg Asp Ala Gln Tyr Ala Pro Gly
625                 630                 635                 640

Tyr Asp Lys Val Lys Asp Ile Ser Glu Val Val Thr Pro Arg Phe Leu
                645                 650                 655

Cys Thr Gly Gly Val Ser Pro Tyr Ala Asp Pro Asn Thr Cys Arg Gly
            660                 665                 670

Asp Ser Gly Gly Pro Leu Ile Val His Lys Arg Ser Arg Phe Ile Gln
        675                 680                 685

Val Gly Val Ile Ser Trp Gly Val Val Asp Val Cys Lys Asn Gln Lys
```

```
                        690             695             700
Arg Gln Lys Gln Val Pro Ala His Ala Arg Asp Phe His Ile Asn Leu
705                 710                 715                 720

Phe Gln Val Leu Pro Trp Leu Lys Glu Lys Leu Gln Asp Glu Asp Leu
                725                 730                 735

Gly Phe Leu

<210> SEQ ID NO 3
<211> LENGTH: 70
<212> TYPE: PRT
<213> ORGANISM: Homo sapiens

<400> SEQUENCE: 3

Ala Arg Pro Gln Gly Ser Cys Ser Leu Glu Gly Val Glu Ile Lys Gly
1               5                   10                  15

Gly Ser Phe Arg Leu Leu Gln Glu Gly Gln Ala Leu Glu Tyr Val Cys
                20                  25                  30

Pro Ser Gly Phe Tyr Pro Tyr Pro Val Gln Thr Arg Thr Cys Arg Ser
            35                  40                  45

Thr Gly Ser Trp Ser Thr Leu Lys Thr Gln Asp Gln Lys Thr Val Arg
        50                  55                  60

Lys Ala Glu Cys Arg Ala
65                  70

<210> SEQ ID NO 4
<211> LENGTH: 60
<212> TYPE: PRT
<213> ORGANISM: Homo sapiens

<400> SEQUENCE: 4

Ile His Cys Pro Arg Pro His Asp Phe Glu Asn Gly Glu Tyr Trp Pro
1               5                   10                  15

Arg Ser Pro Tyr Tyr Asn Val Ser Asp Glu Ile Ser Phe His Cys Tyr
                20                  25                  30

Asp Gly Tyr Thr Leu Arg Gly Ser Ala Asn Arg Thr Cys Gln Val Asn
            35                  40                  45

Gly Arg Trp Ser Gly Gln Thr Ala Ile Cys Asp Asn
        50                  55                  60

<210> SEQ ID NO 5
<211> LENGTH: 48
<212> TYPE: PRT
<213> ORGANISM: Homo sapiens

<400> SEQUENCE: 5

Gly Tyr Cys Ser Asn Pro Gly Ile Pro Ile Gly Thr Arg Lys Val Gly
1               5                   10                  15

Ser Gln Tyr Arg Leu Glu Asp Ser Val Thr Tyr His Cys Ser Arg Gly
                20                  25                  30

Leu Thr Leu Arg Gly Ser Gln Arg Arg Thr Cys Gln Glu Gly Gly Ser
            35                  40                  45

<210> SEQ ID NO 6
<211> LENGTH: 761
<212> TYPE: PRT
<213> ORGANISM: Mus musculus

<400> SEQUENCE: 6

Met Glu Ser Pro Gln Leu Cys Leu Val Leu Leu Val Leu Gly Phe Ser
1               5                   10                  15
```

```
Ser Gly Gly Val Ser Ala Thr Pro Val Leu Glu Ala Arg Pro Gln Val
            20                  25                  30

Ser Cys Ser Leu Glu Gly Val Glu Ile Lys Gly Gly Ser Phe Gln Leu
            35                  40                  45

Leu Gln Gly Gly Gln Ala Leu Glu Tyr Leu Cys Pro Ser Gly Phe Tyr
        50                  55                  60

Pro Tyr Pro Val Gln Thr Arg Thr Cys Arg Ser Thr Gly Ser Trp Ser
65                  70                  75                  80

Asp Leu Gln Thr Arg Asp Gln Lys Ile Val Gln Lys Ala Glu Cys Arg
                85                  90                  95

Ala Ile Arg Cys Pro Arg Pro Gln Asp Phe Glu Asn Gly Glu Phe Trp
            100                 105                 110

Pro Arg Ser Pro Phe Tyr Asn Leu Ser Asp Gln Ile Ser Phe Gln Cys
            115                 120                 125

Tyr Asp Gly Tyr Val Leu Arg Gly Ser Ala Asn Arg Thr Cys Gln Glu
        130                 135                 140

Asn Gly Arg Trp Asp Gly Gln Thr Ala Ile Cys Asp Asp Gly Ala Gly
145                 150                 155                 160

Tyr Cys Pro Asn Pro Gly Ile Pro Ile Gly Thr Arg Lys Val Gly Ser
                165                 170                 175

Gln Tyr Arg Leu Glu Asp Ile Val Thr Tyr His Cys Ser Arg Gly Leu
            180                 185                 190

Val Leu Arg Gly Ser Gln Lys Arg Lys Cys Gln Glu Gly Gly Ser Trp
            195                 200                 205

Ser Gly Thr Glu Pro Ser Cys Gln Asp Ser Phe Met Tyr Asp Ser Pro
210                 215                 220

Gln Glu Val Ala Glu Ala Phe Leu Ser Ser Leu Thr Glu Thr Ile Glu
225                 230                 235                 240

Gly Ala Asp Ala Glu Asp Gly His Ser Pro Gly Glu Gln Gln Lys Arg
                245                 250                 255

Lys Ile Val Leu Asp Pro Ser Gly Ser Met Asn Ile Tyr Leu Val Leu
            260                 265                 270

Asp Gly Ser Asp Ser Ile Gly Ser Ser Asn Phe Thr Gly Ala Lys Arg
            275                 280                 285

Cys Leu Thr Asn Leu Ile Glu Lys Val Ala Ser Tyr Gly Val Arg Pro
290                 295                 300

Arg Tyr Gly Leu Leu Thr Tyr Ala Thr Val Pro Lys Val Leu Val Arg
305                 310                 315                 320

Val Ser Asp Glu Arg Ser Ser Asp Ala Asp Trp Val Thr Glu Lys Leu
            325                 330                 335

Asn Gln Ile Ser Tyr Glu Asp His Lys Leu Lys Ser Gly Thr Asn Thr
            340                 345                 350

Lys Arg Ala Leu Gln Ala Val Tyr Ser Met Met Ser Trp Ala Gly Asp
            355                 360                 365

Ala Pro Pro Glu Gly Trp Asn Arg Thr Arg His Val Ile Ile Ile Met
        370                 375                 380

Thr Asp Gly Leu His Asn Met Gly Gly Asn Pro Val Thr Val Ile Gln
385                 390                 395                 400

Asp Ile Arg Ala Leu Leu Asp Ile Gly Arg Asp Pro Lys Asn Pro Arg
            405                 410                 415

Glu Asp Tyr Leu Asp Val Tyr Val Phe Gly Val Gly Pro Leu Val Asp
            420                 425                 430

Ser Val Asn Ile Asn Ala Leu Ala Ser Lys Lys Asp Asn Glu His His
```

-continued

```
            435                 440                 445
Val Phe Lys Val Lys Asp Met Glu Asp Leu Glu Asn Val Phe Tyr Gln
            450                 455                 460

Met Ile Asp Glu Thr Lys Ser Leu Ser Leu Cys Gly Met Val Trp Glu
465                 470                 475                 480

His Lys Lys Gly Asn Asp Tyr His Lys Gln Pro Trp Gln Ala Lys Ile
                    485                 490                 495

Ser Val Thr Arg Pro Leu Lys Gly His Glu Thr Cys Met Gly Ala Val
                500                 505                 510

Val Ser Glu Tyr Phe Val Leu Thr Ala Ala His Cys Phe Met Val Asp
                515                 520                 525

Asp Gln Lys His Ser Ile Lys Val Ser Val Gly Gly Gln Arg Arg Asp
            530                 535                 540

Leu Glu Ile Glu Glu Val Leu Phe His Pro Lys Tyr Asn Ile Asn Gly
545                 550                 555                 560

Lys Lys Ala Glu Gly Ile Pro Glu Phe Tyr Asp Tyr Asp Val Ala Leu
                565                 570                 575

Val Lys Leu Lys Asn Lys Leu Lys Tyr Gly Gln Thr Leu Arg Pro Ile
                580                 585                 590

Cys Leu Pro Cys Thr Glu Gly Thr Thr Arg Ala Leu Arg Leu Pro Gln
            595                 600                 605

Thr Ala Thr Cys Lys Gln His Lys Glu Gln Leu Leu Pro Val Lys Asp
            610                 615                 620

Val Lys Ala Leu Phe Val Ser Glu Gln Gly Lys Ser Leu Thr Arg Lys
625                 630                 635                 640

Glu Val Tyr Ile Lys Asn Gly Asp Lys Lys Ala Ser Cys Glu Arg Asp
                    645                 650                 655

Ala Thr Lys Ala Gln Gly Tyr Glu Lys Val Lys Asp Ala Ser Glu Val
                660                 665                 670

Val Thr Pro Arg Phe Leu Cys Thr Gly Gly Val Asp Pro Tyr Ala Asp
                675                 680                 685

Pro Asn Thr Cys Lys Gly Asp Ser Gly Gly Pro Leu Ile Val His Lys
            690                 695                 700

Arg Ser Arg Phe Ile Gln Val Gly Val Ile Ser Trp Gly Val Val Asp
705                 710                 715                 720

Val Cys Arg Asp Gln Arg Arg Gln Gln Leu Val Pro Ser Tyr Ala Arg
                    725                 730                 735

Asp Phe His Ile Asn Leu Phe Gln Val Leu Pro Trp Leu Lys Asp Lys
                    740                 745                 750

Leu Lys Asp Glu Asp Leu Gly Phe Leu
            755                 760
```